US011103575B2

(12) United States Patent
Du et al.

(10) Patent No.: US 11,103,575 B2
(45) Date of Patent: Aug. 31, 2021

(54) IMMUNOGENIC COMPOSITION FOR MERS CORONAVIRUS INFECTION

(71) Applicant: New York Blood Center, Inc., New York, NY (US)

(72) Inventors: Lanying Du, Rego Park, NY (US); Fang Li, Roseville, MN (US); Shibo Jiang, Flushing, NY (US); Yusen Zhou, Beijing (CN)

(73) Assignee: The New York Blood Center, Inc., New York, NY (US)

( * ) Notice: Subject to any disclaimer, the term of this patent is extended or adjusted under 35 U.S.C. 154(b) by 180 days.

(21) Appl. No.: 16/462,125

(22) PCT Filed: Nov. 17, 2017

(86) PCT No.: PCT/US2017/062354
§ 371 (c)(1),
(2) Date: May 17, 2019

(87) PCT Pub. No.: WO2018/094241
PCT Pub. Date: May 24, 2018

(65) Prior Publication Data
US 2019/0328865 A1    Oct. 31, 2019

Related U.S. Application Data

(63) Continuation-in-part of application No. 14/375,083, filed on Jul. 28, 2014, now Pat. No. 9,889,194.

(60) Provisional application No. 62/424,309, filed on Nov. 18, 2016.

(51) Int. Cl.
| A61P 31/14 | (2006.01) |
| C07K 14/005 | (2006.01) |
| A61K 39/215 | (2006.01) |
| C12N 7/00 | (2006.01) |
| A61K 39/00 | (2006.01) |

(52) U.S. Cl.
CPC ............ *A61K 39/215* (2013.01); *A61P 31/14* (2018.01); *C07K 14/005* (2013.01); *C12N 7/00* (2013.01); *A61K 2039/545* (2013.01); *A61K 2039/55516* (2013.01); *A61K 2039/575* (2013.01); *A61K 2039/627* (2013.01); *C07K 2319/30* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| 8,936,789 B2 | 1/2015 | Jiang et al. |
| 2006/0257852 A1 | 11/2006 | Rappuoli et al. |
| 2011/0086058 A1 | 4/2011 | Jiang et al. |
| 2015/0017207 A1 | 1/2015 | Gale et al. |
| 2016/0206729 A1 | 7/2016 | Smith et al. |
| 2016/0296617 A1 | 10/2016 | Zhou et al. |

FOREIGN PATENT DOCUMENTS

| CN | 103554235 | 2/2014 |
| WO | 2005-018538 A2 | 3/2005 |
| WO | 2014121132 | 8/2014 |
| WO | 2014134439 | 9/2014 |
| WO | 2014045254 | 2/2015 |
| WO | 2015042373 | 3/2015 |
| WO | 2015057942 | 4/2015 |
| WO | 2015057966 | 4/2015 |
| WO | 2015081155 | 6/2015 |
| WO | 2015143335 | 9/2015 |
| WO | 2016138160 | 9/2016 |

OTHER PUBLICATIONS

Diamond and Pierson, Cell Host Microbe, May 2020, 27(5):699-703. (Year: 2020).*
Li et al., J. Biomed. Sci., 2020, 27:104, 23 pages. (Year: 2020).*
Du et al., "A truncated receptor-binding domain of MERS-CoV spike protein potently inhibits MERS-CoV infection and induces strong neutralizing antibody responses: implication for developing therapeutics and vaccines", Plos One, vol. 8, No. 12, Article No. e81587, pp. 1-9, Dec. 2013.
He et al., "Identification of immunodominant sites on the spike protein of severe acute respiratory syndrome (SARS) coronavirus: implication for developing SARS diagnostics and vaccines", The Journal of Immunology, vol. 173, No. 6, pp. 4050-4057, Sep. 15, 2004.
Zaki et al., "Isolation of a novel coronavirus from a man with pneumonia in Saudi Arabia", The new England Journal of Medicine, vol. 367, No. 19, pp. 1814-1820, Nov. 8, 2012.
Perlman S. "The Middle East Respiratory Syndrome—How worried should we be?" mBio 4:e00531-13, 2013.
Perlman et al. "Human coronavirus EMC is not the same as Severe Acute Respiratory Syndrome coronavirus," mBio 4:e00002-13, 2013.
Van Boheemen et al. "Genomic characterization of a newly discovered coronavirus associated with Acute Respiratory Distress Syndrome in humans," mBio 3:e00473-12, 2012.
Jiang S et al. "A predicted receptor-binding and critical neutralizing domain in S protein of the novel human coronavirus HcoV-EMC" J Infect 66:464-466, 2012.
Du L et al. "The spike protein of SARS-CoV—a target for vaccine and therapeutic development" Nature Rev Microbiol 7:226-236, 2009.

(Continued)

*Primary Examiner* — Stacy B Chen
(74) *Attorney, Agent, or Firm* — K&L Gates LLP; Louis C. Cullman; Michelle Glasky Bergman

(57) ABSTRACT

Described herein are immunogenic compositions for preventing infection with Middle East respiratory syndrome coronavirus (MERS-CoV) wherein the immunogenic compositions comprise at least a portion of the MERS-CoV S protein and an immunopotentiator.

20 Claims, 25 Drawing Sheets

Specification includes a Sequence Listing.

(56) References Cited

OTHER PUBLICATIONS

Yan et al. "Strategies for designing peptide immunogens to elicit [alpha]-helical conformation-specific antibodies reactive with native proteins" ACS Symposium Series 1095:93-136, 2012.
Du L et al. "Identification of a receptor-binding domain in the S protein of the novel human coronavirus Middle East Respiratory Syndrome coronavirus as an essential target for vaccine development" J Virol 87:9939-9942, 2013.
Chen Y et al. "Crystal structure of the receptor-binding domain from newly emerged Middle East Respiratory Syndrome coronavirus" J Virol 87:10777-10783, 2013.
Gierer S et al. "The spike protein of the emerging betacoronavirus EMC uses a novel coronavirus receptor for entry, can be activated by TMPRSS2, and is targeted by neutralizing antibodies" J Viral 87:5502-5511, 2013.
UNIPROT:K0BRG7 Database accession, (2012).
Wang N et al. "Structure of MERS-CoV spike receptor-binding domain complexed with human receptor DPP4" Cell Res-Xibao Yanjui 23:986-993, 2013.
Raj et al. "Dipeptidyl peptidase 4 is a functional receptor for the emerging human coronavirus—EMC" Nature 495:251-254, 2013.
Lu G et al. "Molecular basis of binding between novel human coronavirus MERS-CoV and its receptor CD26" Nature 500:227-231, 2013.
Zhou et al. "The receptor binding domain of MERS-CoV: the dawn of vaccine and treatment development" J for Med Assoc 113:143-147, 2013.
Supplementary European Search Report dated Sep. 26, 2016 for European Patent Application No. EP 14757347.1 filed on Feb. 28, 2014.
Qiu et al. Microbiology and Immunology 56:554-561, 2012.
Chen et al. Journal of Virology 87(19):10777-10783, 2013.
Edmund et al. Arch. Immunol. Ther. Exp. 57:311-323, 2009.
Du L et al. "Introduction of neutralizing immunogenicity index to the rational design of MERS coronavirus subunit vaccines," Nat Commun 7:13473, 2016.
Kim et al. "Variations in spike glycoprotein gene of MERS-CoV, South Korea, 2015" Emerging Infectious Dis. 22:100-1044, 2016.
Kim et al. "Spread of mutant Middle East Respiratory Syndrome Coronavirus with reduced affinity to human CD26 luring the South Korean Outbreak," mBio 7(2):e00019-16, pp. 1-8, 2016.
International Search Report and Written Opinion for PCT/US2017/062354, (2018).
U.S. Appl. No. 14/375,083, filed Jul. 28, 2014, Immunogenic Compositions for MERS Coronavirus Infection.

* cited by examiner

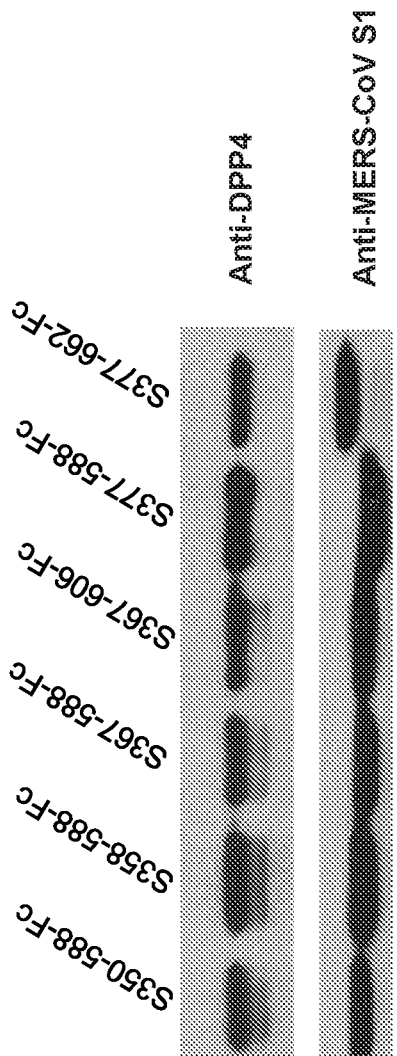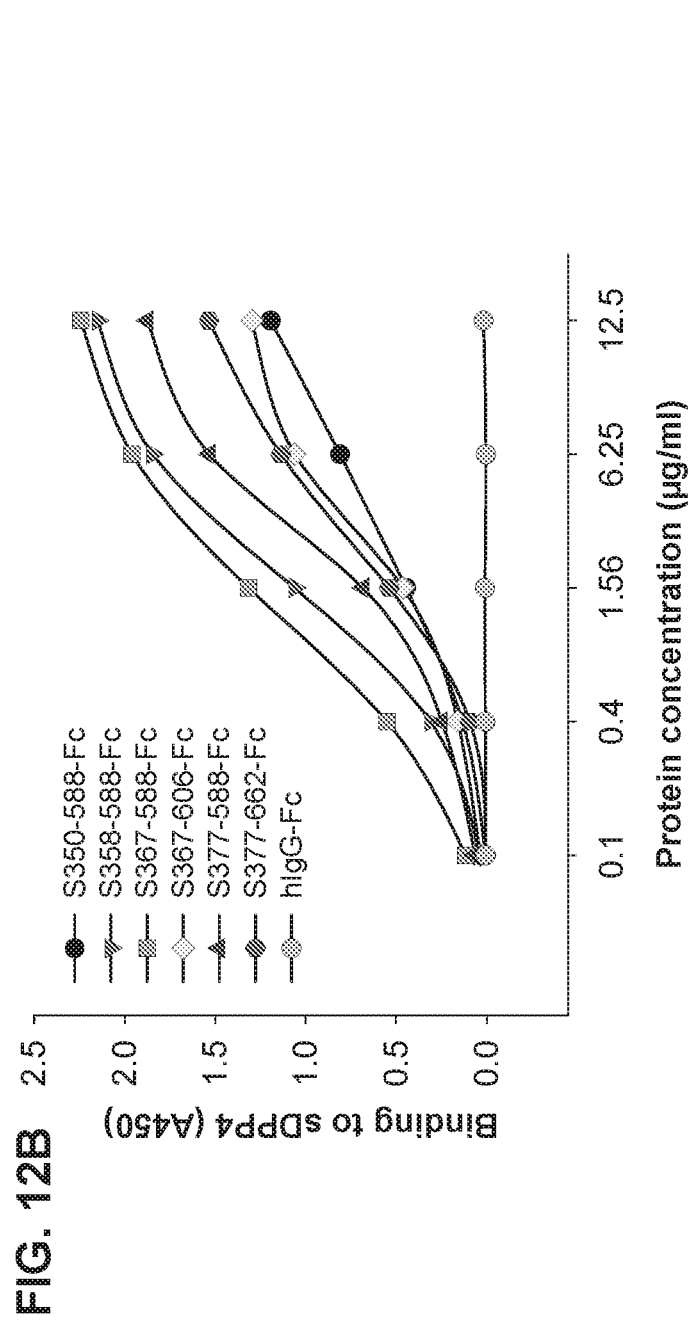
FIG. 12A
FIG. 12B

FIG. 21B
Neutralizing immunogenicity index (NII)
= (NT$_{50\text{-}wt}$ − NT$_{50\text{-}probe}$) / NT$_{50\text{-}wt}$

FIG. 21C

200

SEQUENCE LISTING

<160> NUMBER OF SEQ ID NOS: 26

<210> SEQ ID NO 1
<211> LENGTH: 1353
<212> TYPE: PRT
<213> ORGANISM: MERS coronavirus

<400> SEQUENCE: 1

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
                20                  25                  30

Val Asp Ile Gln Gln Thr Phe Phe Asp Lys Thr Trp Pro Arg Pro Ile
            35                  40                  45

Asp Val Ser Lys Ala Asp Gly Ile Ile Tyr Pro Gln Gly Arg Thr Tyr
        50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
```

```
                275                 280                 285
Thr Ile Lys Tyr Tyr Ser Ile Ile Pro His Ser Ile Arg Ser Ile Gln
290                 295                 300
Ser Asp Arg Lys Ala Trp Ala Ala Phe Tyr Val Tyr Lys Leu Gln Pro
305                 310                 315                 320
Leu Thr Phe Leu Leu Asp Phe Ser Val Asp Gly Tyr Ile Arg Arg Ala
                325                 330                 335
Ile Asp Cys Gly Phe Asn Asp Leu Ser Gln Leu His Cys Ser Tyr Glu
                340                 345                 350
Ser Phe Asp Val Glu Ser Gly Val Tyr Ser Val Ser Ser Phe Glu Ala
                355                 360                 365
Lys Pro Ser Gly Ser Val Val Glu Gln Ala Glu Gly Val Glu Cys Asp
                370                 375                 380
Phe Ser Pro Leu Leu Ser Gly Thr Pro Pro Gln Val Tyr Asn Phe Lys
385                 390                 395                 400
Arg Leu Val Phe Thr Asn Cys Asn Tyr Asn Leu Thr Lys Leu Leu Ser
                405                 410                 415
Leu Phe Ser Val Asn Asp Phe Thr Cys Ser Gln Ile Ser Pro Ala Ala
                420                 425                 430
Ile Ala Ser Asn Cys Tyr Ser Ser Leu Ile Leu Asp Tyr Phe Ser Tyr
                435                 440                 445
Pro Leu Ser Met Lys Ser Asp Leu Ser Val Ser Ser Ala Gly Pro Ile
                450                 455                 460
Ser Gln Phe Asn Tyr Lys Gln Ser Phe Ser Asn Pro Thr Cys Leu Ile
465                 470                 475                 480
Leu Ala Thr Val Pro His Asn Leu Thr Thr Ile Thr Lys Pro Leu Lys
                485                 490                 495
Tyr Ser Tyr Ile Asn Lys Cys Ser Arg Leu Leu Ser Asp Asp Arg Thr
                500                 505                 510
Glu Val Pro Gln Leu Val Asn Ala Asn Gln Tyr Ser Pro Cys Val Ser
                515                 520                 525
Ile Val Pro Ser Thr Val Trp Glu Asp Gly Asp Tyr Tyr Arg Lys Gln
                530                 535                 540
Leu Ser Pro Leu Glu Gly Gly Gly Trp Leu Val Ala Ser Gly Ser Thr
545                 550                 555                 560
Val Ala Met Thr Glu Gln Leu Gln Met Gly Phe Gly Ile Thr Val Gln
                565                 570                 575
Tyr Gly Thr Asp Thr Asn Ser Val Cys Pro Lys Leu Glu Phe Ala Asn
                580                 585                 590
Asp Thr Lys Ile Ala Ser Gln Leu Gly Asn Cys Val Glu Tyr Ser Leu
                595                 600                 605
Tyr Gly Val Ser Gly Arg Gly Val Phe Gln Asn Cys Thr Ala Val Gly
                610                 615                 620
Val Arg Gln Gln Arg Phe Val Tyr Asp Ala Tyr Gln Asn Leu Val Gly
625                 630                 635                 640
Tyr Tyr Ser Asp Asp Gly Asn Tyr Tyr Cys Leu Arg Ala Cys Val Ser
                645                 650                 655
Val Pro Val Ser Val Ile Tyr Asp Lys Glu Thr Lys Thr His Ala Thr
                660                 665                 670
Leu Phe Gly Ser Val Ala Cys Glu His Ile Ser Ser Thr Met Ser Gln
                675                 680                 685
Tyr Ser Arg Ser Thr Arg Ser Met Leu Lys Arg Arg Asp Ser Thr Tyr
                690                 695                 700
```

```
Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
        740                 745                 750

Val Pro Gly Glu Met Arg Leu Ala Ser Ile Ala Phe Asn His Pro Ile
    755                 760                 765

Gln Val Asp Gln Leu Asn Ser Ser Tyr Phe Lys Leu Ser Ile Pro Thr
770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
            805                 810                 815

Cys Glu Gln Leu Leu Arg Glu Tyr Gly Gln Phe Cys Ser Lys Ile Asn
        820                 825                 830

Gln Ala Leu His Gly Ala Asn Leu Arg Gln Asp Asp Ser Val Arg Asn
    835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
        900                 905                 910

Met Gln Gln Gly Pro Ala Ser Ala Arg Asp Leu Ile Cys Ala Gln Tyr
    915                 920                 925

Val Ala Gly Tyr Lys Val Leu Pro Pro Leu Met Asp Val Asn Met Glu
930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
        980                 985                 990

Asn Gln Lys Leu Ile Ala Asn Lys Phe Asn Gln Ala Leu Gly Ala Met
    995                 1000                1005

Gln Thr Gly Phe Thr Thr Thr Asn Glu Ala Phe Gln Lys Val Gln
    1010            1015                1020

Asp Ala Val Asn Asn Asn Ala Gln Ala Leu Ser Lys Leu Ala Ser
    1025            1030                1035

Glu Leu Ser Asn Thr Phe Gly Ala Ile Ser Ala Ser Ile Gly Asp
    1040            1045                1050

Ile Ile Gln Arg Leu Asp Val Leu Glu Gln Asp Ala Gln Ile Asp
    1055            1060                1065

Arg Leu Ile Asn Gly Arg Leu Thr Thr Leu Asn Ala Phe Val Ala
    1070            1075                1080

Gln Gln Leu Val Arg Ser Glu Ser Ala Ala Leu Ser Ala Gln Leu
    1085            1090                1095

Ala Lys Asp Lys Val Asn Glu Cys Val Lys Ala Gln Ser Lys Arg
    1100            1105                1110
```

Ser Gly Phe Cys Gly Gln Gly Thr His Ile Val Ser Phe Val Val
     1115                1120                1125

Asn Ala Pro Asn Gly Leu Tyr Phe Met His Val Gly Tyr Tyr Pro
     1130                1135                1140

Ser Asn His Ile Glu Val Val Ser Ala Tyr Gly Leu Cys Asp Ala
     1145                1150                1155

Ala Asn Pro Thr Asn Cys Ile Ala Pro Val Asn Gly Tyr Phe Ile
     1160                1165                1170

Lys Thr Asn Asn Thr Arg Ile Val Asp Glu Trp Ser Tyr Thr Gly
     1175                1180                1185

Ser Ser Phe Tyr Ala Pro Glu Pro Ile Thr Ser Leu Asn Thr Lys
     1190                1195                1200

Tyr Val Ala Pro Gln Val Thr Tyr Gln Asn Ile Ser Thr Asn Leu
     1205                1210                1215

Pro Pro Pro Leu Leu Gly Asn Ser Thr Gly Ile Asp Phe Gln Asp
     1220                1225                1230

Glu Leu Asp Glu Phe Phe Lys Asn Val Ser Thr Ser Ile Pro Asn
     1235                1240                1245

Phe Gly Ser Leu Thr Gln Ile Asn Thr Thr Leu Leu Asp Leu Thr
     1250                1255                1260

Tyr Glu Met Leu Ser Leu Gln Gln Val Val Lys Ala Leu Asn Glu
     1265                1270                1275

Ser Tyr Ile Asp Leu Lys Glu Leu Gly Asn Tyr Thr Tyr Tyr Asn
     1280                1285                1290

Lys Trp Pro Trp Tyr Ile Trp Leu Gly Phe Ile Ala Gly Leu Val
     1295                1300                1305

Ala Leu Ala Leu Cys Val Phe Phe Ile Leu Cys Cys Thr Gly Cys
     1310                1315                1320

Gly Thr Asn Cys Met Gly Lys Leu Lys Cys Asn Arg Cys Cys Asp
     1325                1330                1335

Arg Tyr Glu Glu Tyr Asp Leu Glu Pro His Lys Val His Val His
     1340                1345                1350

<210> SEQ ID NO 2
<211> LENGTH: 286
<212> TYPE: PRT
<213> ORGANISM: MERS coronavirus

<400> SEQUENCE: 2

Gln Ala Glu Gly Val Glu Cys Asp Phe Ser Pro Leu Leu Ser Gly Thr
1               5                   10                  15

Pro Pro Gln Val Tyr Asn Phe Lys Arg Leu Val Phe Thr Asn Cys Asn
                20                  25                  30

Tyr Asn Leu Thr Lys Leu Leu Ser Leu Phe Ser Val Asn Asp Phe Thr
            35                  40                  45

Cys Ser Gln Ile Ser Pro Ala Ala Ile Ala Ser Asn Cys Tyr Ser Ser
        50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
        115                 120                 125

```
Arg Leu Leu Ser Asp Asp Arg Thr Glu Val Pro Gln Leu Val Asn Ala
    130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
                180                 185                 190

Met Gly Phe Gly Ile Thr Val Gln Tyr Gly Thr Asp Thr Asn Ser Val
            195                 200                 205

Cys Pro Lys Leu Glu Phe Ala Asn Asp Thr Lys Ile Ala Ser Gln Leu
    210                 215                 220

Gly Asn Cys Val Glu Tyr Ser Leu Tyr Gly Val Ser Gly Arg Gly Val
225                 230                 235                 240

Phe Gln Asn Cys Thr Ala Val Gly Val Arg Gln Gln Arg Phe Val Tyr
                245                 250                 255

Asp Ala Tyr Gln Asn Leu Val Gly Tyr Tyr Ser Asp Asp Gly Asn Tyr
                260                 265                 270

Tyr Cys Leu Arg Ala Cys Val Ser Val Pro Val Ser Val Ile
            275                 280                 285

<210> SEQ ID NO 3
<211> LENGTH: 212
<212> TYPE: PRT
<213> ORGANISM: MERS coronavirus

<400> SEQUENCE: 3

Gln Ala Glu Gly Val Glu Cys Asp Phe Ser Pro Leu Leu Ser Gly Thr
1               5                   10                  15

Pro Pro Gln Val Tyr Asn Phe Lys Arg Leu Val Phe Thr Asn Cys Asn
                20                  25                  30

Tyr Asn Leu Thr Lys Leu Leu Ser Leu Phe Ser Val Asn Asp Phe Thr
            35                  40                  45

Cys Ser Gln Ile Ser Pro Ala Ala Ile Ala Ser Asn Cys Tyr Ser Ser
50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
        115                 120                 125

Arg Leu Leu Ser Asp Asp Arg Thr Glu Val Pro Gln Leu Val Asn Ala
    130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
                180                 185                 190

Met Gly Phe Gly Ile Thr Val Gln Tyr Gly Thr Asp Thr Asn Ser Val
            195                 200                 205

Cys Pro Lys Leu
```

<210> SEQ ID NO 4
<211> LENGTH: 239
<212> TYPE: PRT
<213> ORGANISM: MERS coronavirus

<400> SEQUENCE: 4

Ser Tyr Glu Ser Phe Asp Val Glu Ser Gly Val Tyr Ser Val Ser Ser
1               5                   10                  15

Phe Glu Ala Lys Pro Ser Gly Ser Val Val Glu Gln Ala Glu Gly Val
            20                  25                  30

Glu Cys Asp Phe Ser Pro Leu Leu Ser Gly Thr Pro Pro Gln Val Tyr
        35                  40                  45

Asn Phe Lys Arg Leu Val Phe Thr Asn Cys Asn Tyr Asn Leu Thr Lys
    50                  55                  60

Leu Leu Ser Leu Phe Ser Val Asn Asp Phe Thr Cys Ser Gln Ile Ser
65                  70                  75                  80

Pro Ala Ala Ile Ala Ser Asn Cys Tyr Ser Ser Leu Ile Leu Asp Tyr
                85                  90                  95

Phe Ser Tyr Pro Leu Ser Met Lys Ser Asp Leu Ser Val Ser Ser Ala
            100                 105                 110

Gly Pro Ile Ser Gln Phe Asn Tyr Lys Gln Ser Phe Ser Asn Pro Thr
        115                 120                 125

Cys Leu Ile Leu Ala Thr Val Pro His Asn Leu Thr Thr Ile Thr Lys
    130                 135                 140

Pro Leu Lys Tyr Ser Tyr Ile Asn Lys Cys Ser Arg Leu Leu Ser Asp
145                 150                 155                 160

Asp Arg Thr Glu Val Pro Gln Leu Val Asn Ala Asn Gln Tyr Ser Pro
                165                 170                 175

Cys Val Ser Ile Val Pro Ser Thr Val Trp Glu Asp Gly Asp Tyr Tyr
            180                 185                 190

Arg Lys Gln Leu Ser Pro Leu Glu Gly Gly Gly Trp Leu Val Ala Ser
        195                 200                 205

Gly Ser Thr Val Ala Met Thr Glu Gln Leu Gln Met Gly Phe Gly Ile
    210                 215                 220

Thr Val Gln Tyr Gly Thr Asp Thr Asn Ser Val Cys Pro Lys Leu
225                 230                 235

<210> SEQ ID NO 5
<211> LENGTH: 231
<212> TYPE: PRT
<213> ORGANISM: MERS coronavirus

<400> SEQUENCE: 5

Ser Gly Val Tyr Ser Val Ser Ser Phe Glu Ala Lys Pro Ser Gly Ser
1               5                   10                  15

Val Val Glu Gln Ala Glu Gly Val Glu Cys Asp Phe Ser Pro Leu Leu
            20                  25                  30

Ser Gly Thr Pro Pro Gln Val Tyr Asn Phe Lys Arg Leu Val Phe Thr
        35                  40                  45

Asn Cys Asn Tyr Asn Leu Thr Lys Leu Leu Ser Leu Phe Ser Val Asn
    50                  55                  60

Asp Phe Thr Cys Ser Gln Ile Ser Pro Ala Ala Ile Ala Ser Asn Cys
65                  70                  75                  80

Tyr Ser Ser Leu Ile Leu Asp Tyr Phe Ser Tyr Pro Leu Ser Met Lys

```
                         85                  90                  95
Ser Asp Leu Ser Val Ser Ser Ala Gly Pro Ile Ser Gln Phe Asn Tyr
            100                 105                 110

Lys Gln Ser Phe Ser Asn Pro Thr Cys Leu Ile Leu Ala Thr Val Pro
            115                 120                 125

His Asn Leu Thr Thr Ile Thr Lys Pro Leu Lys Tyr Ser Tyr Ile Asn
            130                 135                 140

Lys Cys Ser Arg Leu Leu Ser Asp Asp Arg Thr Glu Val Pro Gln Leu
145                 150                 155                 160

Val Asn Ala Asn Gln Tyr Ser Pro Cys Val Ser Ile Val Pro Ser Thr
                165                 170                 175

Val Trp Glu Asp Gly Asp Tyr Tyr Arg Lys Gln Leu Ser Pro Leu Glu
            180                 185                 190

Gly Gly Gly Trp Leu Val Ala Ser Gly Ser Thr Val Ala Met Thr Glu
            195                 200                 205

Gln Leu Gln Met Gly Phe Gly Ile Thr Val Gln Tyr Gly Thr Asp Thr
            210                 215                 220

Asn Ser Val Cys Pro Lys Leu
225                 230

<210> SEQ ID NO 6
<211> LENGTH: 222
<212> TYPE: PRT
<213> ORGANISM: MERS coronavirus

<400> SEQUENCE: 6

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
            115                 120                 125

Leu Lys Tyr Ser Tyr Ile Asn Lys Cys Ser Arg Leu Leu Ser Asp Asp
            130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
            195                 200                 205

Val Gln Tyr Gly Thr Asp Thr Asn Ser Val Cys Pro Lys Leu
            210                 215                 220
```

<210> SEQ ID NO 7
<211> LENGTH: 240
<212> TYPE: PRT
<213> ORGANISM: MERS coronavirus

<400> SEQUENCE: 7

Glu Ala Lys Pro Ser Gly Ser Val Val Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Leu Leu Ser Asp Asp
    130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn Cys Val Glu Tyr
225                 230                 235                 240

<210> SEQ ID NO 8
<211> LENGTH: 468
<212> TYPE: PRT
<213> ORGANISM: artificial sequence
<220> FEATURE:
<223> OTHER INFORMATION: S350-588-Fc peptide

<400> SEQUENCE: 8

Ser Tyr Glu Ser Phe Asp Val Glu Ser Gly Val Tyr Ser Val Ser Ser
1               5                   10                  15

Phe Glu Ala Lys Pro Ser Gly Ser Val Val Gln Ala Glu Gly Val
            20                  25                  30

Glu Cys Asp Phe Ser Pro Leu Leu Ser Gly Thr Pro Pro Gln Val Tyr
        35                  40                  45

Asn Phe Lys Arg Leu Val Phe Thr Asn Cys Asn Tyr Asn Leu Thr Lys
    50                  55                  60

Leu Leu Ser Leu Phe Ser Val Asn Asp Phe Thr Cys Ser Gln Ile Ser
65                  70                  75                  80

Pro Ala Ala Ile Ala Ser Asn Cys Tyr Ser Ser Leu Ile Leu Asp Tyr

```
                  85                  90                  95
Phe Ser Tyr Pro Leu Ser Met Lys Ser Asp Leu Ser Val Ser Ser Ala
                100                 105                 110

Gly Pro Ile Ser Gln Phe Asn Tyr Lys Gln Ser Phe Ser Asn Pro Thr
            115                 120                 125

Cys Leu Ile Leu Ala Thr Val Pro His Asn Leu Thr Thr Ile Thr Lys
        130                 135                 140

Pro Leu Lys Tyr Ser Tyr Ile Asn Lys Cys Ser Arg Leu Leu Ser Asp
145                 150                 155                 160

Asp Arg Thr Glu Val Pro Gln Leu Val Asn Ala Asn Gln Tyr Ser Pro
                165                 170                 175

Cys Val Ser Ile Val Pro Ser Thr Val Trp Glu Asp Gly Asp Tyr Tyr
            180                 185                 190

Arg Lys Gln Leu Ser Pro Leu Glu Gly Gly Gly Trp Leu Val Ala Ser
                195                 200                 205

Gly Ser Thr Val Ala Met Thr Glu Gln Leu Gln Met Gly Phe Gly Ile
            210                 215                 220

Thr Val Gln Tyr Gly Thr Asp Thr Asn Ser Val Cys Pro Lys Leu Arg
225                 230                 235                 240

Ser Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 9
<211> LENGTH: 460
<212> TYPE: PRT
<213> ORGANISM: artificial sequence
```

<220> FEATURE:
<223> OTHER INFORMATION: S358-588-Fc peptide

<400> SEQUENCE: 9

```
Ser Gly Val Tyr Ser Val Ser Phe Glu Ala Lys Pro Ser Gly Ser
1               5                   10                  15

Val Val Glu Gln Ala Glu Gly Val Glu Cys Asp Phe Ser Pro Leu Leu
                20                  25                  30

Ser Gly Thr Pro Pro Gln Val Tyr Asn Phe Lys Arg Leu Val Phe Thr
        35                  40                  45

Asn Cys Asn Tyr Asn Leu Thr Lys Leu Leu Ser Leu Phe Ser Val Asn
    50                  55                  60

Asp Phe Thr Cys Ser Gln Ile Ser Pro Ala Ala Ile Ala Ser Asn Cys
65                  70                  75                  80

Tyr Ser Ser Leu Ile Leu Asp Tyr Phe Ser Tyr Pro Leu Ser Met Lys
                85                  90                  95

Ser Asp Leu Ser Val Ser Ser Ala Gly Pro Ile Ser Gln Phe Asn Tyr
            100                 105                 110

Lys Gln Ser Phe Ser Asn Pro Thr Cys Leu Ile Leu Ala Thr Val Pro
        115                 120                 125

His Asn Leu Thr Thr Ile Thr Lys Pro Leu Lys Tyr Ser Tyr Ile Asn
    130                 135                 140

Lys Cys Ser Arg Leu Leu Ser Asp Asp Arg Thr Glu Val Pro Gln Leu
145                 150                 155                 160

Val Asn Ala Asn Gln Tyr Ser Pro Cys Val Ser Ile Val Pro Ser Thr
                165                 170                 175

Val Trp Glu Asp Gly Asp Tyr Tyr Arg Lys Gln Leu Ser Pro Leu Glu
            180                 185                 190

Gly Gly Gly Trp Leu Val Ala Ser Gly Ser Thr Val Ala Met Thr Glu
        195                 200                 205

Gln Leu Gln Met Gly Phe Gly Ile Thr Val Gln Tyr Gly Thr Asp Thr
    210                 215                 220

Asn Ser Val Cys Pro Lys Leu Arg Ser Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Ser Asn Gly Gln Pro
385                 390                 395                 400
```

Glu Asn Asn Tyr Lys Thr Thr Pro Pro Val Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460

<210> SEQ ID NO 10
<211> LENGTH: 451
<212> TYPE: PRT
<213> ORGANISM: artificial sequence
<220> FEATURE:
<223> OTHER INFORMATION: S367-588-Fc peptide

<400> SEQUENCE: 10

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
    50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Leu Leu Ser Asp Asp
    130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Arg Ser
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 11
<211> LENGTH: 469
<212> TYPE: PRT
<213> ORGANISM: artificial sequence
<220> FEATURE:
<223> OTHER INFORMATION: S367-606-Fc peptide

<400> SEQUENCE: 11

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
            35                  40                  45

Leu Ser Leu Phe Ser Val Asn Asp Phe Thr Cys Ser Gln Ile Ser Pro
        50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
            85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
            115                 120                 125

Leu Lys Tyr Ser Tyr Ile Asn Lys Cys Ser Arg Leu Leu Ser Asp Asp
            130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
            165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
            195                 200                 205
```

-continued

Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn Cys Val Glu Tyr
225                 230                 235                 240

Arg Ser Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 12
<211> LENGTH: 441
<212> TYPE: PRT
<213> ORGANISM: artificial sequence
<220> FEATURE:
<223> OTHER INFORMATION: S377-588-Fc peptide

<400> SEQUENCE: 12

Gln Ala Glu Gly Val Glu Cys Asp Phe Ser Pro Leu Leu Ser Gly Thr
1               5                   10                  15

Pro Pro Gln Val Tyr Asn Phe Lys Arg Leu Val Phe Thr Asn Cys Asn
            20                  25                  30

Tyr Asn Leu Thr Lys Leu Leu Ser Leu Phe Ser Val Asn Asp Phe Thr
        35                  40                  45

Cys Ser Gln Ile Ser Pro Ala Ala Ile Ala Ser Asn Cys Tyr Ser Ser
    50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

```
Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
        115                 120                 125

Arg Leu Leu Ser Asp Asp Arg Thr Glu Val Pro Gln Leu Val Asn Ala
    130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
            180                 185                 190

Met Gly Phe Gly Ile Thr Val Gln Tyr Gly Thr Asp Thr Asn Ser Val
        195                 200                 205

Cys Pro Lys Leu Arg Ser Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 13
<211> LENGTH: 515
<212> TYPE: PRT
<213> ORGANISM: artificial sequence
<220> FEATURE:
<223> OTHER INFORMATION: S377-662-Fc peptide

<400> SEQUENCE: 13

Gln Ala Glu Gly Val Glu Cys Asp Phe Ser Pro Leu Leu Ser Gly Thr
1               5                   10                  15
```

Pro Pro Gln Val Tyr Asn Phe Lys Arg Leu Val Phe Thr Asn Cys Asn
            20                  25                  30

Tyr Asn Leu Thr Lys Leu Leu Ser Leu Phe Ser Val Asn Asp Phe Thr
            35                  40                  45

Cys Ser Gln Ile Ser Pro Ala Ala Ile Ala Ser Asn Cys Tyr Ser Ser
        50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
            115                 120                 125

Arg Leu Leu Ser Asp Asp Arg Thr Glu Val Pro Gln Leu Val Asn Ala
130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
            180                 185                 190

Met Gly Phe Gly Ile Thr Val Gln Tyr Gly Thr Asp Thr Asn Ser Val
        195                 200                 205

Cys Pro Lys Leu Glu Phe Ala Asn Asp Thr Lys Ile Ala Ser Gln Leu
    210                 215                 220

Gly Asn Cys Val Glu Tyr Ser Leu Tyr Gly Val Ser Gly Arg Gly Val
225                 230                 235                 240

Phe Gln Asn Cys Thr Ala Val Gly Val Arg Gln Gln Arg Phe Val Tyr
                245                 250                 255

Asp Ala Tyr Gln Asn Leu Val Gly Tyr Tyr Ser Asp Asp Gly Asn Tyr
            260                 265                 270

Tyr Cys Leu Arg Ala Cys Val Ser Val Pro Val Ser Val Ile Arg Ser
        275                 280                 285

Asp Lys Thr His Thr Cys Pro Pro Cys Pro Ala Pro Glu Leu Leu Gly
    290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
            340                 345                 350

His Asn Ala Lys Thr Lys Pro Arg Glu Glu Gln Tyr Asn Ser Thr Tyr
        355                 360                 365

Arg Val Val Ser Val Leu Thr Val Leu His Gln Asp Trp Leu Asn Gly
    370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
                405                 410                 415

Tyr Thr Leu Pro Pro Ser Arg Glu Glu Met Thr Lys Asn Gln Val Ser
            420                 425                 430

```
Leu Thr Cys Leu Val Lys Gly Phe Tyr Pro Ser Asp Ile Ala Val Glu
        435                 440                 445

Trp Glu Ser Asn Gly Gln Pro Glu Asn Asn Tyr Lys Thr Thr Pro Pro
    450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys
        515

<210> SEQ ID NO 14
<211> LENGTH: 27
<212> TYPE: PRT
<213> ORGANISM: Bacteriophage T4

<400> SEQUENCE: 14

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 15
<211> LENGTH: 229
<212> TYPE: PRT
<213> ORGANISM: homo sapiens

<400> SEQUENCE: 15

Arg Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205
```

Val Met His Glu Ala Leu His Asn His Tyr Thr Gln Lys Ser Leu Ser
    210                 215                 220

Leu Ser Pro Gly Lys
225

<210> SEQ ID NO 16
<211> LENGTH: 234
<212> TYPE: PRT
<213> ORGANISM: mus musculus

<400> SEQUENCE: 16

Arg Ser Pro Arg Gly Pro Thr Ile Lys Pro Cys Pro Pro Cys Lys Cys
1               5                   10                  15

Pro Ala Pro Asn Leu Leu Gly Gly Pro Ser Val Phe Ile Phe Pro Pro
                20                  25                  30

Lys Ile Lys Asp Val Leu Met Ile Ser Leu Ser Pro Ile Val Thr Cys
            35                  40                  45

Val Val Val Asp Val Ser Glu Asp Asp Pro Asp Val Gln Ile Ser Trp
50                  55                  60

Phe Val Asn Asn Val Glu Val His Thr Ala Gln Thr Gln Thr His Arg
65                  70                  75                  80

Glu Asp Tyr Asn Ser Thr Leu Arg Val Val Ser Ala Leu Pro Ile Gln
                85                  90                  95

His Gln Asp Trp Met Ser Gly Lys Glu Phe Lys Cys Lys Val Asn Asn
            100                 105                 110

Lys Asp Leu Pro Ala Pro Ile Glu Arg Thr Ile Ser Lys Pro Lys Gly
        115                 120                 125

Ser Val Arg Ala Pro Gln Val Tyr Val Leu Pro Pro Pro Glu Glu Glu
130                 135                 140

Met Thr Lys Lys Gln Val Thr Leu Thr Cys Met Val Thr Asp Phe Met
145                 150                 155                 160

Pro Glu Asp Ile Tyr Val Glu Trp Thr Asn Asn Gly Lys Thr Glu Leu
                165                 170                 175

Asn Tyr Lys Asn Thr Glu Pro Val Leu Asp Ser Asp Gly Ser Tyr Phe
            180                 185                 190

Met Tyr Ser Lys Leu Arg Val Glu Lys Lys Asn Trp Val Glu Arg Asn
        195                 200                 205

Ser Tyr Ser Cys Ser Val Val His Glu Gly Leu His Asn His His Thr
    210                 215                 220

Thr Lys Ser Phe Ser Arg Thr Pro Gly Lys
225                 230

<210> SEQ ID NO 17
<211> LENGTH: 225
<212> TYPE: PRT
<213> ORGANISM: Oryctolagus cuniculus

<400> SEQUENCE: 17

Arg Ser Ser Lys Pro Thr Cys Pro Pro Pro Glu Leu Leu Gly Gly Pro
1               5                   10                  15

Ser Val Phe Ile Phe Pro Pro Lys Pro Lys Asp Thr Leu Met Ile Ser
                20                  25                  30

Arg Thr Pro Glu Val Thr Cys Val Val Val Asp Val Ser Gln Asp Asp
            35                  40                  45

Pro Glu Val Gln Phe Thr Trp Tyr Ile Asn Asn Glu Gln Val Arg Thr
50                  55                  60

```
Ala Arg Pro Pro Leu Arg Glu Gln Gln Phe Asn Ser Thr Ile Arg Val
 65                  70                  75                  80

Val Ser Thr Leu Pro Ile Ala His Gln Asp Trp Leu Arg Gly Lys Glu
                 85                  90                  95

Phe Lys Cys Lys Val His Asn Lys Ala Leu Pro Ala Pro Ile Glu Lys
            100                 105                 110

Thr Ile Ser Lys Ala Arg Gly Gln Pro Leu Glu Pro Lys Val Tyr Thr
        115                 120                 125

Met Gly Pro Pro Arg Glu Glu Leu Ser Ser Arg Ser Val Ser Leu Thr
130                 135                 140

Cys Met Ile Asn Gly Phe Tyr Pro Ser Asp Ile Ser Val Glu Trp Glu
145                 150                 155                 160

Lys Asn Gly Lys Ala Glu Asp Asn Tyr Lys Thr Thr Pro Ala Val Leu
                165                 170                 175

Asp Ser Asp Gly Ser Tyr Phe Leu Tyr Ser Lys Leu Ser Val Pro Thr
            180                 185                 190

Ser Glu Trp Gln Arg Gly Asp Val Phe Thr Cys Ser Val Met His Glu
        195                 200                 205

Ala Leu His Asn His Tyr Thr Gln Lys Ser Ile Ser Arg Ser Pro Gly
    210                 215                 220

Lys
225

<210> SEQ ID NO 18
<211> LENGTH: 302
<212> TYPE: PRT
<213> ORGANISM: homo sapiens

<400> SEQUENCE: 18

His Leu Ile Val Thr Pro Ser Gly Cys Gly Glu Gln Asn Met Ile Gly
  1               5                  10                  15

Met Thr Pro Thr Val Ile Ala Val His Tyr Leu Asp Glu Thr Glu Gln
                 20                  25                  30

Trp Glu Lys Phe Gly Leu Glu Lys Arg Gln Gly Ala Leu Glu Leu Ile
             35                  40                  45

Lys Lys Gly Tyr Thr Gln Gln Leu Ala Phe Arg Gln Pro Ser Ser Ala
 50                  55                  60

Phe Ala Ala Phe Val Lys Arg Ala Pro Ser Thr Trp Leu Thr Ala Tyr
 65                  70                  75                  80

Val Val Lys Val Phe Ser Leu Ala Val Asn Leu Ile Ala Ile Asp Ser
                 85                  90                  95

Gln Val Leu Cys Gly Ala Val Lys Trp Leu Ile Leu Glu Lys Gln Lys
            100                 105                 110

Pro Asp Gly Val Phe Gln Glu Asp Ala Pro Val Ile His Gln Glu Met
        115                 120                 125

Ile Gly Gly Leu Arg Asn Asn Asn Glu Lys Asp Met Ala Leu Thr Ala
130                 135                 140

Phe Val Leu Ile Ser Leu Gln Glu Ala Lys Asp Ile Cys Glu Glu Gln
145                 150                 155                 160

Val Asn Ser Leu Pro Gly Ser Ile Thr Lys Ala Gly Asp Phe Leu Glu
                165                 170                 175

Ala Asn Tyr Met Asn Leu Gln Arg Ser Tyr Thr Val Ala Ile Ala Gly
            180                 185                 190

Tyr Ala Leu Ala Gln Met Gly Arg Leu Lys Gly Pro Leu Leu Asn Lys
        195                 200                 205
```

```
Phe Leu Thr Thr Ala Lys Asp Lys Asn Arg Trp Glu Asp Pro Gly Lys
    210                 215                 220

Gln Leu Tyr Asn Val Glu Ala Thr Ser Tyr Ala Leu Leu Ala Leu Leu
225                 230                 235                 240

Gln Leu Lys Asp Phe Asp Phe Val Pro Pro Val Val Arg Trp Leu Asn
                245                 250                 255

Glu Gln Arg Tyr Tyr Gly Gly Gly Tyr Gly Ser Thr Gln Ala Thr Phe
                260                 265                 270

Met Val Phe Gln Ala Leu Ala Gln Tyr Gln Lys Asp Ala Pro Asp His
        275                 280                 285

Gln Glu Leu Asn Leu Asp Val Ser Leu Gln Leu Pro Ser Arg
    290                 295                 300

<210> SEQ ID NO 19
<211> LENGTH: 104
<212> TYPE: PRT
<213> ORGANISM: vibrio cholerae

<400> SEQUENCE: 19

Met Thr Pro Gln Asn Ile Thr Asp Leu Cys Ala Glu Tyr His Asn Thr
1               5                   10                  15

Gln Ile His Thr Leu Asn Asp Lys Ile Phe Ser Tyr Thr Glu Ser Leu
            20                  25                  30

Ala Gly Lys Arg Glu Met Ala Ile Ile Thr Phe Lys Asn Gly Ala Thr
        35                  40                  45

Phe Gln Val Glu Val Pro Gly Ser Gln His Ile Asp Ser Gln Lys Lys
    50                  55                  60

Ala Ile Glu Arg Met Lys Asp Thr Leu Arg Ile Ala Tyr Leu Thr Glu
65                  70                  75                  80

Ala Lys Val Glu Lys Leu Cys Val Trp Asn Asn Lys Thr Pro Arg Ala
                85                  90                  95

Ile Ala Ala Ile Ser Met Ala Asn
            100

<210> SEQ ID NO 20
<211> LENGTH: 29
<212> TYPE: PRT
<213> ORGANISM: Bacteriophage T4

<400> SEQUENCE: 20

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25

<210> SEQ ID NO 21
<211> LENGTH: 32
<212> TYPE: PRT
<213> ORGANISM: Saccharomyces cerevisiae

<400> SEQUENCE: 21

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30

<210> SEQ ID NO 22
<211> LENGTH: 28
```

```
<212> TYPE: PRT
<213> ORGANISM: artificial sequence
<220> FEATURE:
<223> OTHER INFORMATION: IQ trimerization sequence

<400> SEQUENCE: 22

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys
            20                  25

<210> SEQ ID NO 23
<211> LENGTH: 24
<212> TYPE: PRT
<213> ORGANISM: artificial sequence
<220> FEATURE:
<223> OTHER INFORMATION: IZ trimerization sequence

<400> SEQUENCE: 23

Ile Lys Lys Glu Ile Glu Ala Ile Lys Lys Glu Gln Glu Ala Ile Lys
1               5                   10                  15

Lys Lys Ile Glu Ala Ile Glu Lys
            20

<210> SEQ ID NO 24
<211> LENGTH: 5
<212> TYPE: PRT
<213> ORGANISM: artificial sequence
<220> FEATURE:
<223> OTHER INFORMATION: Linker sequence

<400> SEQUENCE: 24

Gly Gly Gly Gly Ser
1               5

<210> SEQ ID NO 25
<211> LENGTH: 212
<212> TYPE: PRT
<213> ORGANISM: Artificial Sequence
<220> FEATURE:
<223> OTHER INFORMATION: aa377-588 of MERS-CoV S protein with T579N
      mutation

<400> SEQUENCE: 25

Gln Ala Glu Gly Val Glu Cys Asp Phe Ser Pro Leu Leu Ser Gly Thr
1               5                   10                  15

Pro Pro Gln Val Tyr Asn Phe Lys Arg Leu Val Phe Thr Asn Cys Asn
            20                  25                  30

Tyr Asn Leu Thr Lys Leu Leu Ser Leu Phe Ser Val Asn Asp Phe Thr
        35                  40                  45

Cys Ser Gln Ile Ser Pro Ala Ala Ile Ala Ser Asn Cys Tyr Ser Ser
    50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

Phe Ser Asn Pro Thr Cys Leu Ile Leu Ala Thr Val Pro His Asn Leu
            100                 105                 110

Thr Thr Ile Thr Lys Pro Leu Lys Tyr Ser Tyr Ile Asn Lys Cys Ser
        115                 120                 125

Arg Leu Leu Ser Asp Asp Arg Thr Glu Val Pro Gln Leu Val Asn Ala
    130                 135                 140
```

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
            180                 185                 190

Met Gly Phe Gly Ile Thr Val Gln Tyr Gly Asn Asp Thr Asn Ser Val
        195                 200                 205

Cys Pro Lys Leu
        210

<210> SEQ ID NO 26
<211> LENGTH: 441
<212> TYPE: PRT
<213> ORGANISM: Artificial Sequence
<220> FEATURE:
<223> OTHER INFORMATION: S377-588-Fc with T579N mutation

<400> SEQUENCE: 26

Gln Ala Glu Gly Val Glu Cys Asp Phe Ser Pro Leu Leu Ser Gly Thr
1               5                   10                  15

Pro Pro Gln Val Tyr Asn Phe Lys Arg Leu Val Phe Thr Asn Cys Asn
                20                  25                  30

Tyr Asn Leu Thr Lys Leu Leu Ser Leu Phe Ser Val Asn Asp Phe Thr
            35                  40                  45

Cys Ser Gln Ile Ser Pro Ala Ala Ile Ala Ser Asn Cys Tyr Ser Ser
        50                  55                  60

Leu Ile Leu Asp Tyr Phe Ser Tyr Pro Leu Ser Met Lys Ser Asp Leu
65                  70                  75                  80

Ser Val Ser Ser Ala Gly Pro Ile Ser Gln Phe Asn Tyr Lys Gln Ser
                85                  90                  95

Phe Ser Asn Pro Thr Cys Leu Ile Leu Ala Thr Val Pro His Asn Leu
                100                 105                 110

Thr Thr Ile Thr Lys Pro Leu Lys Tyr Ser Tyr Ile Asn Lys Cys Ser
            115                 120                 125

Arg Leu Leu Ser Asp Asp Arg Thr Glu Val Pro Gln Leu Val Asn Ala
130                 135                 140

Asn Gln Tyr Ser Pro Cys Val Ser Ile Val Pro Ser Thr Val Trp Glu
145                 150                 155                 160

Asp Gly Asp Tyr Tyr Arg Lys Gln Leu Ser Pro Leu Glu Gly Gly Gly
                165                 170                 175

Trp Leu Val Ala Ser Gly Ser Thr Val Ala Met Thr Glu Gln Leu Gln
            180                 185                 190

Met Gly Phe Gly Ile Thr Val Gln Tyr Gly Asn Asp Thr Asn Ser Val
        195                 200                 205

Cys Pro Lys Leu Arg Ser Asp Lys Thr His Thr Cys Pro Pro Cys Pro
        210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

-continued

```
Gln Tyr Asn Ser Thr Tyr Arg Val Val Ser Val Leu Thr Val Leu His
    290                 295                 300
Gln Asp Trp Leu Asn Gly Lys Glu Tyr Lys Cys Lys Val Ser Asn Lys
305                 310                 315                 320
Ala Leu Pro Ala Pro Ile Glu Lys Thr Ile Ser Lys Ala Lys Gly Gln
                325                 330                 335
Pro Arg Glu Pro Gln Val Tyr Thr Leu Pro Pro Ser Arg Glu Glu Met
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
    370                 375                 380
Tyr Lys Thr Thr Pro Pro Val Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys
        435                 440
```

IMMUNOGENIC COMPOSITION FOR MERS CORONAVIRUS INFECTION

CROSS-REFERENCE TO RELATED APPLICATIONS

The present application is a 35 U.S.C. 371 national phase entry of PCT/US2017/062354, filed Nov. 17, 2017, which claims the benefit under 35 U.S.C. § 119(e) to U.S. provisional patent application 62/424,309 filed Nov. 18, 2016. The present application is also a continuation-in-part of U.S. patent application Ser. No. 14/375,083 filed Jul. 28, 2014, now U.S. Pat. No. 9,889,194. The entire contents of each of these applications are incorporated by reference herein.

GOVERNMENT SUPPORT CLAUSE

This invention was made with government support under Grant Numbers AI089728, AI110700, AI060699, AI098775, AI124260, AI109094, AI113206 awarded by the National Institutes of Health. The Government has certain rights in the invention.

FIELD OF THE INVENTION

The present disclosure relates to the field of immunogenic compositions for the prevention and treatment of infection with human MERS coronavirus.

BACKGROUND

Coronaviruses infect and cause disease in a wide variety of species, including bats, birds, cats, dogs, pigs, mice, horses, whales, and humans. Bats act as a natural reservoir for coronaviruses. Most infections caused by human coronaviruses are relatively mild. However, the outbreak of severe acute respiratory syndrome (SARS) caused by SARC-CoV in 2002-2003, and fatal infection in 2012 caused by a recently identified coronavirus, Middle East respiratory syndrome coronavirus (MERS-CoV, also known as hCoV-EMC or NCoV) demonstrated that coronaviruses are also able to cause severe, sometimes fatal disease in humans.

The recently identified coronavirus MERS-CoV has over 40% mortality rate among the infected individuals. This virus also demonstrates person-to-person transmission, posing a continuous threat to public health worldwide. Thus, development of vaccines and antiviral agents against this new virus are urgently needed.

SUMMARY

Disclosed herein are immunogenic compositions for the prevention or treatment of infection with a new coronavirus MERS-CoV (also known as hCoV-EMC or NCoV). The disclosed immunogenic compositions are proteins comprising: 1) at least a portion of the MERS-CoV genome, and 2) an immunopotentiator sequence. The sequences are contiguous and expressed as a single protein in a mammalian expression system, or the MERS-CoV portion and the immunopotentiator are chemically linked and stabilized. Optionally, a stabilization sequence and/or a linker sequence are disposed between the MERS-CoV sequence and the immunopotentiator.

Also disclosed herein are immunogenic compositions comprising a protein, the protein comprising a MERS-CoV S protein sequence comprising amino acids 377-588 of the MERS-Co-V S protein with a T579N mutation; and an immunopotentiator.

In one embodiment, the immunopotentiator sequence is an Fc fragment of human IgG (Fc), a C3d protein, an *Onchocerca volvulus* ASP-1, a cholera toxin, a muramyl peptide, or a cytokine. In another embodiment, the immunopotentiator is Fc.

In another embodiment, the protein further comprises a stabilization sequence disposed between the MERS-CoV S protein sequence and the immunopotentiator sequence. In another embodiment, the stabilization sequence is a foldon (Fd) or GCN4.

In yet another embodiment, the protein further comprises a linker sequence disposed between the MERS-CoV S protein sequence and the immunopotentiator sequence, and the linker is (GGGGS)$_n$, wherein n is an integer between 0 and 8. In another embodiment, n is 1.

In another embodiment, the protein is produced in a mammalian expression system.

In another embodiment, the protein comprises the sequence of S377-588-Fc T579N (SEQ ID NO:26).

In another embodiment, the immunogenic composition further comprises an adjuvant.

Also provided is a method of inducing a protective immune response against MERS-CoV comprising administering the immunogenic composition to a subject in need thereof; wherein the immunogenic composition induces a protective immune response against challenge with MERS-CoV in the host.

In another embodiment, the immunogenic composition further comprises an adjuvant.

In one embodiment, the administering step comprises a prime immunization and at least one boost immunization. In another embodiment, the boost immunizations are administered at least twice. In another embodiment, n the boost immunizations are administered weekly, every other week, monthly, or every other month. In yet another embodiment, the boost immunizations are administered weekly, every 2 weeks, every 3 weeks, every 4 weeks, every 5 weeks, every 6 weeks, every 7 weeks, every 8 weeks, every 9 weeks, every 10 weeks, every 11 weeks, or every 12 weeks.

BRIEF DESCRIPTION OF THE DRAWINGS

FIG. 1 depicts the schematic representation of spike (S) protein of Middle East respiratory syndrome coronavirus (MERS-CoV) and the recombinant S377-662-Fc (human IgG Fc) protein. The MERS-CoV S protein includes the following functional domains in the S1 and S2: signal peptide (SP), receptor-binding domain (RBD), receptor-binding motif (RBM), fusion peptide (FP), heptad repeat 1 (HR1), heptad repeat 2 (HR2), transmembrane domain (TM), and cytoplasm domain (CP).

FIG. 3 depicts the binding of a series of severe acute respiratory syndrome (SARS) S protein-specific mAbs (1 µg/ml) to MERS-CoV S377-662-Fc protein and SARS-CoV S-RBD protein. The HA-7 mAb specific for the hemagglutinin (HA1) of H5N1 virus was used as an unrelated mAb control. The data are presented as mean A450±standard deviation (SD) of duplicate wells.

FIG. 4A and FIG. 4B depict the antibody responses and neutralization induced by MERS-CoV S377-662-Fc protein. FIG. 4A depicts binding to MERS-CoV S377-662 and SARS-CoV S-RBD proteins by antibodies in mouse sera collected 10 days post-$2^{nd}$ immunization. The data are presented as mean A450±SD of five mice per group at various dilution points. FIG. 4B depicts neutralization of the MERS-CoV virus by the same antisera as in FIG. 4A. Neutralizing antibody titers were expressed as the reciprocal of the highest dilution of sera that completely inhibited virus-induced cytopathic effect (CPE) in at least 50% of the wells ($NT_{50}$), and are presented as mean±SD from five mice per group.

FIG. 6A depicts binding of IgG to a MERS-CoV S1 protein containing residues 18-725 of MERS-CoV 51 with a His6 tag (S1-His). Sera from 10 days post-last immunization were used for the detection, and the data are presented as mean A450±SD of five mice per group at various dilution points. FIG. 6B depicts the long-term IgG antibody responses using sera collected at 0, 1, 2, 3, 4, 6 months after the first immunization and 10 days post-last immunization. The data are presented as mean (IgG endpoint titers)±SD of five mice per group.

FIG. 10A and FIG. 10B depict a schematic representation of the S1 subunit of MERS-CoV (FIG. 10A) and recombinant proteins containing various fragments of the RBD domain of MERS-CoV S protein (FIG. 10B). Recombinant proteins S350-588-Fc, S358-588-Fc, S367-588-Fc, S367-606-Fc, and S377-588-Fc were constructed by inserting the corresponding RBD fragments into Fc of human IgG, and compared with S377-662-Fc.

FIG. 12A and FIG. 12B depict the binding of the purified MERS-CoV RBD-Fc proteins to cellular receptor dipeptidyl peptidase 4 (DPP4) in Huh-7 cells by co-immunoprecipitation followed by Western blot (FIG. 12A) and soluble DPP4 (sDPP4) by ELISA (FIG. 12B). Proteins were mixed with Huh-7 cell lysates in the presence of protein A sepharose beads, and detected by Western blot using anti-DPP4 antibodies (1 µg/ml) or antisera from mice immunized with MERS-CoV S1-His (1:1,000), respectively.

FIG. 15 depicts the neutralizing antibody titer of antisera from mice immunized s.c. with MERS-CoV RBD-Fc proteins against MERS-CoV infection in Vero E6 cells. Sera from 10 days post-$3^{rd}$ immunization were used for the assay. Neutralizing antibody titers were expressed as the $NT_{50}$, and are presented as mean±SD from five mice per group.

FIG. 16A depicts S377-588-Fc protein (black line, right) bound to Huh-7 cells (gray shade), while the control human IgG Fc protein (black line, left) did not exhibit binding activity. FIG. 16B depicts the inhibition of S377-588-Fc binding to Huh-7 cells (gray shade) by sera from mice immunized with S377-588-Fc (white line), but not by sera from the PBS control group (black line).

(FIG. 19A) Crystal structure of MERS-CoV RBD (PDB access code: 4L3N). The core structure is colored in cyan, and the receptor-binding motif (RBM) in red. Four residues are shown where an N-linked glycan probe was introduced. (FIG. 19B) Structure of MERS-CoV RBD complexed with human DPP4 (PDB access code: 4KR0), showing the role of the four epitopes in the binding of the RBD to DPP4. (FIG. 19C) AlphaScreen assay was performed to detect the binding between recombinant MERS-CoV RBDs and recombinant human DPP4. PBS buffer was used as a negative control. Binding affinity was characterized as AlphaScreen counts. Error bars indicate SEM. *: P<0.001. (FIG. 19D) Fluorescence-activated cell sorting (FACS) was carried out to detect the binding between recombinant MERS-CoV RBDs and cell-surface-expressed human DPP4. Human IgG protein was used as a negative control. Binding affinity was characterized as median fluorescence intensity (MFI). *: P<0.001.

(FIG. 20A-D) ELISA was carried out to detect the binding between recombinant MERS-CoV RBD fragments and neutralizing mAbs. The binding affinity was characterized as the ELISA signal at 450 nm. Each of the mAbs was serially diluted before being used in ELISA. ***: P<0.001. (FIG. 20E) Structure of MERS-CoV RBD, showing the identified binding site of the neutralizing mAbs on the RBD.

FIG. 21A-C. Measurement of neutralizing immunogenicity of RBD epitopes. (FIG. 21A) Measurement of neutralizing antibody titers of mouse sera induced by wild type (WT) or glycosylation mutant RBD. The neutralizing antibody titer of RBD-induced mouse sera was characterized by its capability to inhibit MERS-CoV-induced cytopathic effect (CPE) in cell culture. To this end, serially diluted mouse sera were added to MERS-CoV-infected cells, and the neutralizing antibody titer of the sera was expressed as the reciprocal of the highest dilution of sera that completely inhibited MERS-CoV-induced CPE in at least 50% of the wells ($NT_{50}$). PBS buffer was used as a negative control. *: P<0.05. (FIG. 21B) Calculation of NII for each epitope. $NT_{50\text{-}wt}$: $NT_{50}$ for wild type RBD; $NT_{50\text{-}probe}$:$NT_{50}$ for RBD containing a glycan probe on one of the epitopes. (FIG. 21C) Mapping the calculated NIIs on the three-dimensional structure of MERS-CoV RBD.

DETAILED DESCRIPTION

Development of an effective and safe vaccine against a newly recognized coronavirus MERS-CoV (also known as hCoV-EMC or NCoV) is urgently needed for the prevention of current spread and future outbreaks. The present disclosure describes the development of a MERS-CoV immunogenic composition based on the spike (S) protein of MERS-CoV. This immunogenic composition induced strong immune responses and potent neutralizing antibodies in immunized animals.

As used herein the term "immunogen" refers to any substrate that elicits an immune response in a host. As used herein an "immunogenic composition" refers to an expressed protein or a recombinant vector, with or without an adjuvant, which expresses and/or secretes an immunogen in vivo and wherein the immunogen elicits an immune response in the host. The immunogenic compositions disclosed herein may or may not be immunoprotective or therapeutic. When the immunogenic compositions may prevent, ameliorate, palliate, or eliminate disease from the host then the immunogenic composition may also optionally be referred to as a vaccine. However, the term immunogenic composition is not intended to be limited to vaccines.

MERS-CoV is closely related to severe acute respiratory syndrome (SARS) coronavirus (SARS-CoV). Clinically similar to SARS, MERS-CoV infection leads to severe respiratory illness with renal failure. As the sixth coronavirus known to infect humans and the first human coronavirus in lineage C of betacoronavirus (the same lineage as Bat-CoV-HKU-4 and -HKU-5), MERS-CoV is closely related to SARS-CoV genetically (lineage B). Therefore, MERS-CoV has recently raised serious concerns of a potential pandemic and, as such, it poses a continuous threat to public health worldwide. Human dipeptidyl peptidase 4 (DPP4) has been identified as the MERS-CoV's receptor.

Like other coronaviruses, the MERS-CoV virion utilizes a large surface S glycoprotein for interaction with, and entry into, the target cell. The S glycoprotein consists of a globular S1 domain at the N-terminal region, followed by membrane-proximal S2 domain, a transmembrane domain, and an intracellular domain.

Figure 9B:
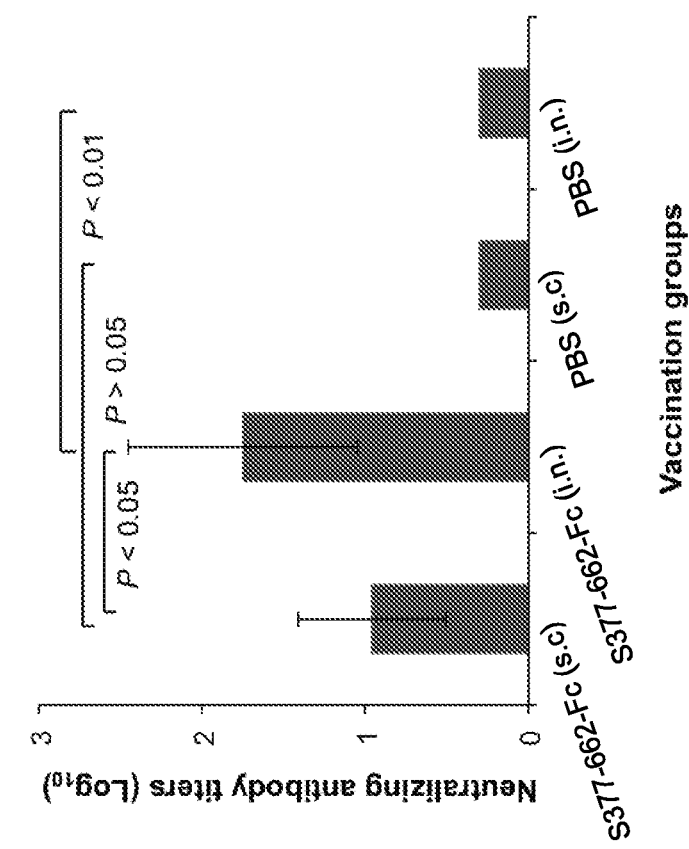
FIG. 9A and FIG. 9B depict the neutralizing antibody titer against MERS-CoV infection from samples of mice immunized (s.c. and i.n.) with MERS-CoV S377-662-Fc protein. Sera (FIG. 9A) and lung wash (1:1,000 dilution in PBS during collection) (FIG. 9B) were collected at 10 days post-last immunization and analyzed for neutralization of MERS-CoV infection in Vero E6 cells. Neutralizing antibody titers were expressed as the $NT_{50}$, and are presented as GMT±SD from five mice per group. $P<0.05$ indicates significant difference.
Figure 9A:
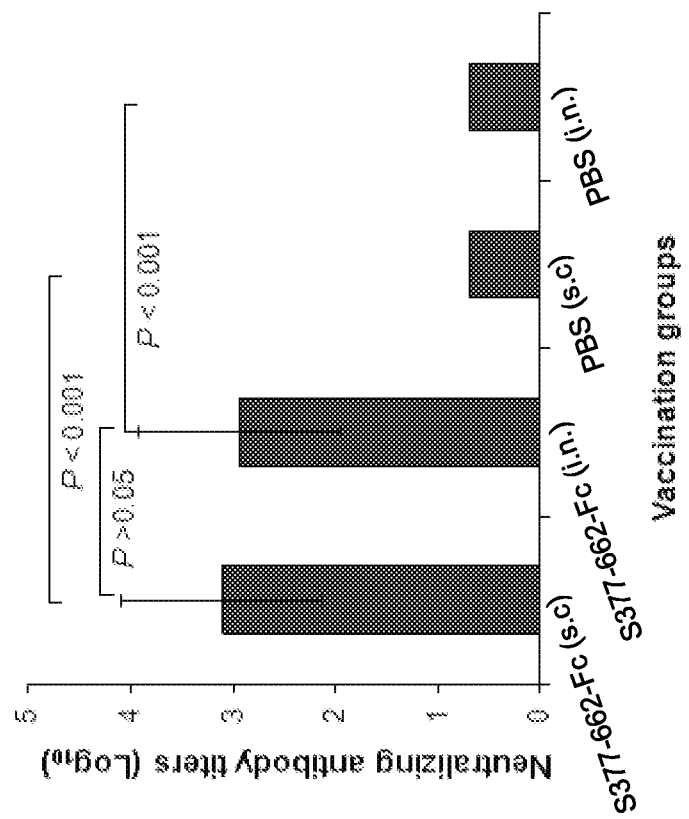
Figure 15:
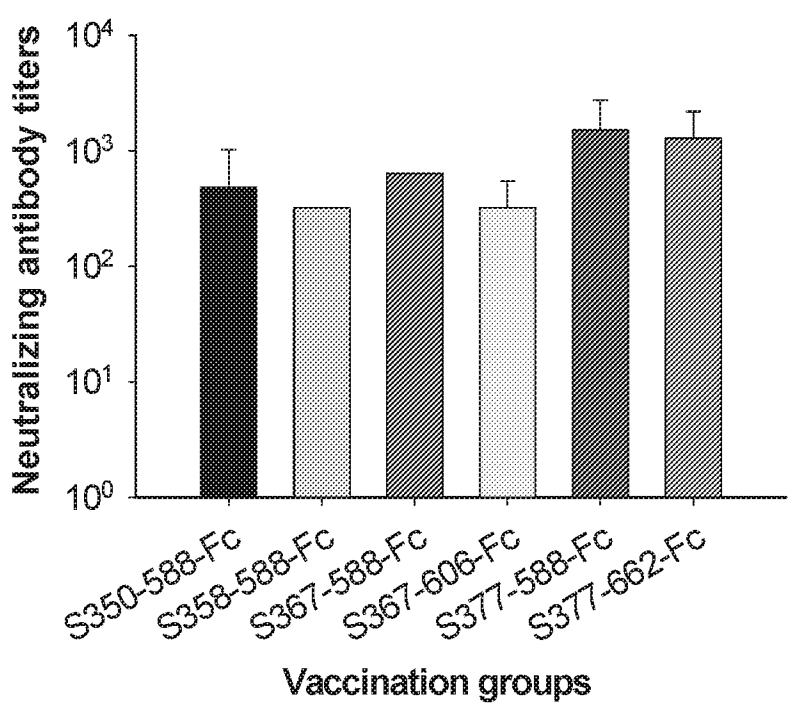
Figure 16:
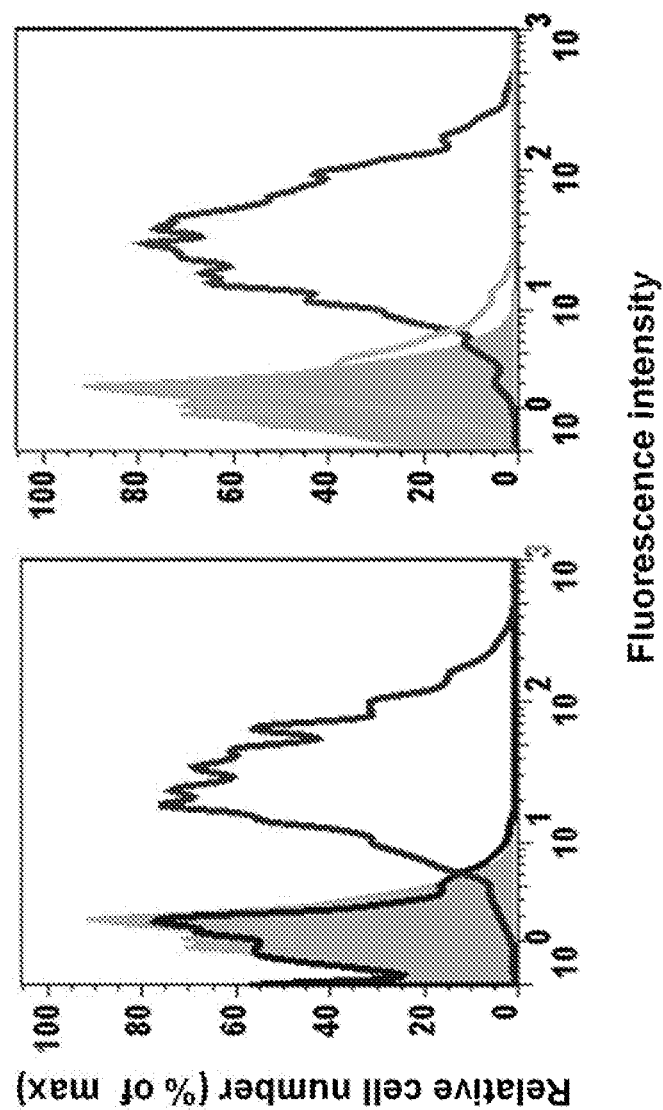
FIG. 16A and FIG. 16B depict the flow cytometry detection of inhibition of MERS-CoV RBD-Fc protein (S377-588-Fc) binding to Huh-7 cells expressing DPP4 receptor by antisera from mice immunized with S377-588-Fc protein.
Figure 17:
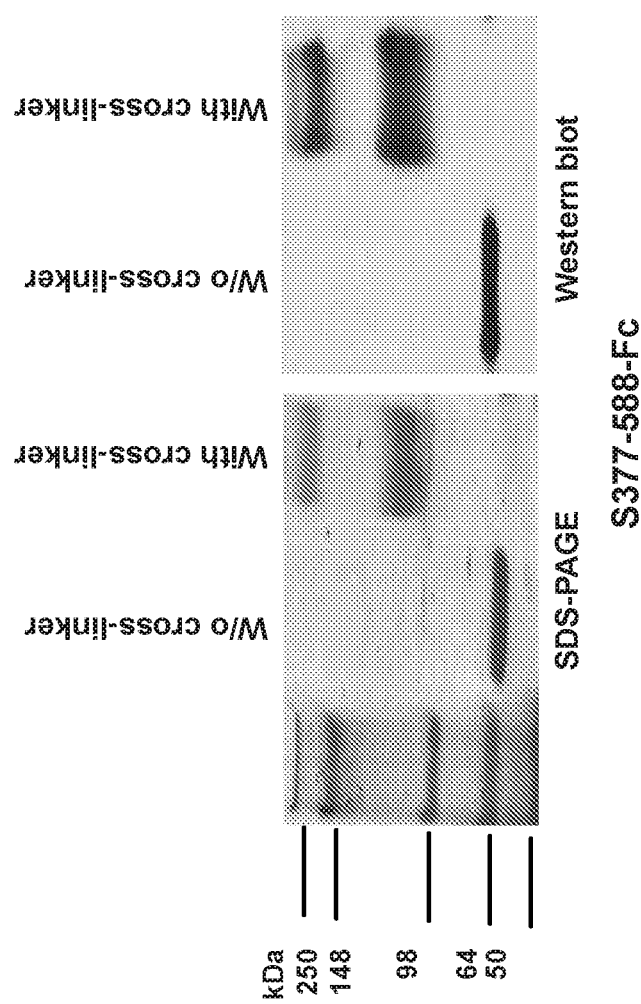
FIG. 17 depicts the conformational structure of MERS-CoV S377-588-Fc protein by cross-linker analysis. The protein was cross-linked with glutaraldehyde or left uncross-linked (w/o cross-linker), followed by Western blot detection using antisera (1:1,000) from mice immunized with MERS-CoV S1-His. The protein molecular weight marker (kDa) is indicated on the left.
Figure 18:
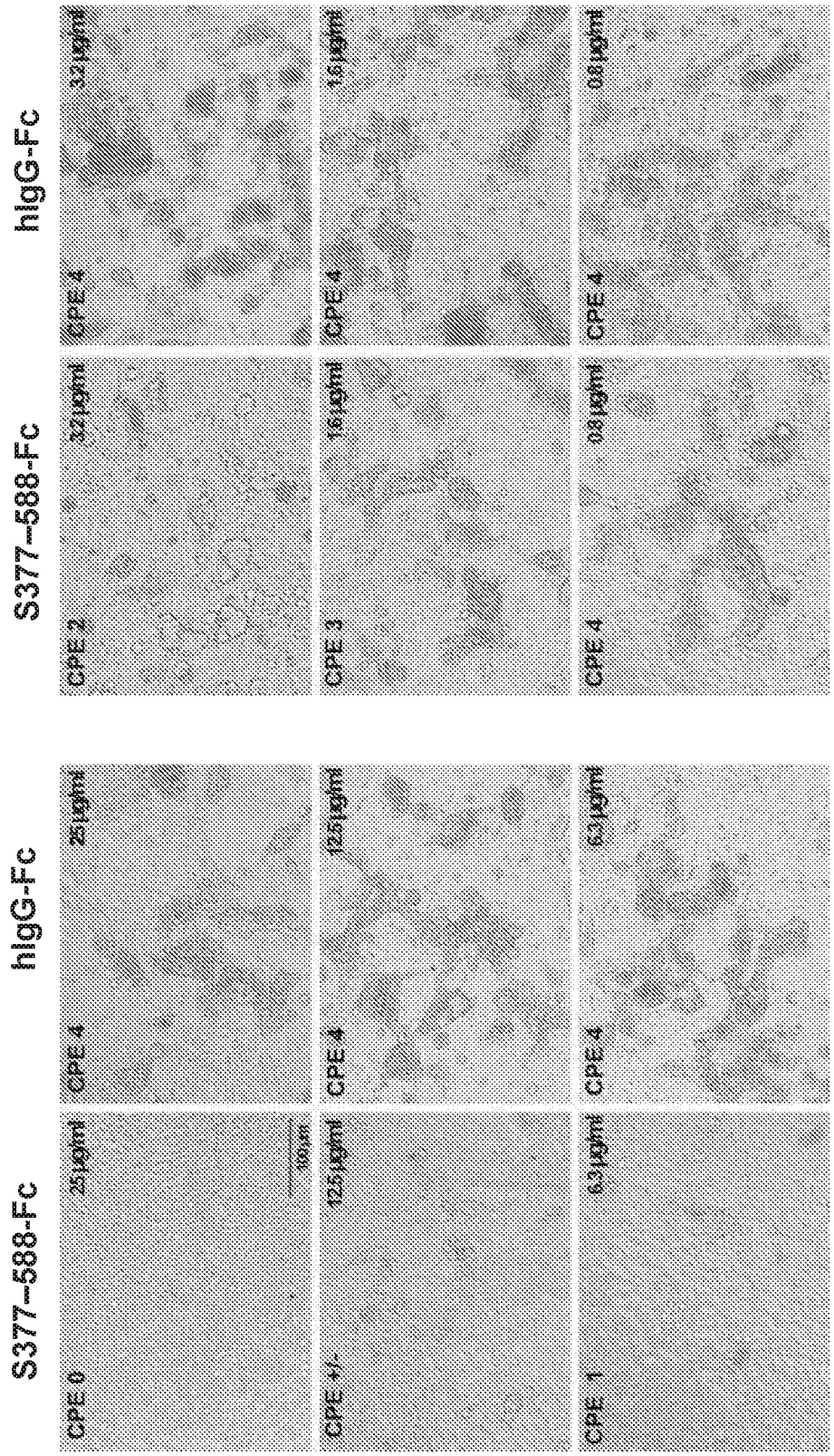
FIG. 18 depicts the inhibition of MERS-CoV infection in Calu-3 cells by MERS-CoV S377-588-Fc protein. Human IgG Fc (hIgG-Fc) was used as the control. The CPE ranged from 0 (none), ±(<5%), 1 (5-10%), 2 (10-25%), 3 (25-50%), and 4 (>50%).

The receptor-binding domain (RBD) of SARS-CoV S protein contains a critical neutralizing domain (CND), which induces potent neutralizing antibodies and protection against SARS-CoV infection in animal models. By comparing and analyzing the S protein sequences of MERS-CoV and SARS-CoV, it was found that the S1 subunit encompassing residues 377-662 of MERS-CoV S protein exhibited a core structure very similar to that of SARS-CoV S protein, suggesting that this region of MERS-CoV S protein also serves as a neutralizing domain. Indeed, a recombinant protein containing residues 377-662 of MERS-CoV S fused to Fc (fragment, crystallizable) domain of human IgG (S377-662-Fc, FIG. 1) was expressed in a mammalian cell expression system (FIG. 2) and is able to induce neutralizing antibodies through both subcutaneous (s.c.) and intranasal (i.n.) routes of administration in an established mouse model of MERS-CoV (FIG. 9). Additionally, recombinant RBD protein fragments spanning residues 350-606 of MERS-CoV S protein were fused to the Fc domain of human IgG (e.g., S350-588-Fc, S358-588-Fc, S367-588-Fc, S377-588-Fc, S367-606-Fc), were expressed in the mammalian cell expression system (FIG. 11), and elicited neutralizing antibodies in immunized mice (FIG. 15). Particularly, a truncated RBD region containing residues 377-588 of MERS-CoV S protein fused to Fc of human IgG (S377-588-Fc) induced a potent neutralizing antibody response in immunized mice (FIG. 15). Antisera from mice immunized with this protein effectively blocked the RBD protein binding to MERS-CoV's receptor DPP4 (FIG. 16). Furthermore, the S377-588-Fc protein was able to form dimeric or tetrameric conformational structures (FIG. 17), and effectively inhibited MERS-CoV infection in DPP4-expressing Calu-3 cells (FIG. 18).

In one embodiment, the S protein sequence component of the instant immunogenic composition comprises a MERS-CoV S protein sequence, a MERS-CoV S1 protein sequence, a MERS-CoV S2 protein sequence, an RBD sequence of a MERS-CoV S protein, a fusion sequence of a MERS-CoV S protein, a heptad repeat sequence of a MERS-CoV S protein, a nucleocapsid sequence of a MERS-CoV S protein, a membrane sequence of a MERS-CoV S protein, or a portion of any of these sequences. In one embodiment, the S protein sequence comprises amino acids 377-662 (SEQ ID NO:2), 377-588 (SEQ ID NO:3), 350-588 (SEQ ID NO:4), 358-588 (SEQ ID NO:5), 367-588 (SEQ ID NO:6), or 367-606 (SEQ ID NO:7) of MERS-CoV S protein.

TABLE 1

Amino acid sequences of MERS-CoV regions and immunopotentiators

SEQ ID NO. 1 [MERS-CoV S protein]:
MIHSVFLLMFLLTPTESYVDVGPDSVKSACIEVDIQQTFFDKTWPRPIDVSKADGIIYPQGRTYSNITI
TYQGLFPYQGDHGDMVYSAGHATGTTPQKLFVANYSQDVKQFANGFVVRIGAAANSTGTVIISPS
TSATIRKIYPAFMLGSSVGNFSDGKMGRFFNHTLVLLPDGCGTLLRAFYCILEPRSGNHCPAGNSYT
SFATYHTPATDCSDGNYNRNASLNSFKEYFNLRNCTFMYTYNITEDEILEWFGITQTAQGVHLFSSR
YVDLYGGNMFQFATLPVYDTIKYYSIIPHSIRSIQSDRKAWAAFYVYKLQPLTFLLDFSVDGYIRRAID
CGFNDLSQLHCSYESFDVESGVYSVSSFEAKPSGSVVEQAEGVECDFSPLLSGTPPQVYNFKRLV
FTNCNYNLTKLLSLFSVNDFTCSQISPAAIASNCYSSLILDYFSYPLSMKSDLSVSSAGPISQFNYKQ
SFSNPTCLILATVPHNLTTITKPLKYSYINKCSRLLSDDRTEVPQLVNANQYSPCVSIVPSTVWEDGD
YYRKQLSPLEGGGWLVASGSTVAMTEQLQMGFGITVQYGTDTNSVCPKLEFANDTKIASQLGNCV
EYSLYGVSGRGVFQNCTAVGVRQQRFVYDAYQNLVGYYSDDGNYYCLRACVSVPVSVIYDKETKT
HATLFGSVACEHISSTMSQYSRSTRSMLKRRDSTYGPLQTPVGCVLGLVNSSLFVEDCKLPLGQSL
CALPDTPSTLTPRSVRSVPGEMRLASIAFNHPIQVDQLNSSYFKLSIPTNFSFGVTQEYIQTTIQKVT
VDCKQYVCNGFQKCEQLLREYGQFCSKINQALHGANLRQDDSVRNLFASVKSSQSSPIIPGFGGD
FNLTLLEPVSISTGSRSARSAIEDLLFDKVTIADPGYMQGYDDCMQQGPASARDLICAQYVAGYKVL
PPLMDVNMEAAYTSSLLGSIAGVGWTAGLSSFAAIPFAQSIFYRLNGVGITQQVLSENQKLIANKFN
QALGAMQTGFTTTNEAFQKVQDAVNNNAQALSKLASELSNTFGAISASIGDIIQRLDVLEQDAQIDR
LINGRLTTLNAFVAQQLVRSESAALSAQLAKDKVNECVKAQSKRSGFCGQGTHIVSFVVNAPNGLY
FMHVGYYPSNHIEVVSAYGLCDAANPTNCIAPVNGYFIKTNNTRIVDEWSYTGSSFYAPEPITSLNT
KYVAPQVTYQNISTNLPPPLLGNSTGIDFQDELDEFFKNVSTSIPNFGSLTQINTTLLDLTYEMLSLQ
QVVKALNESYIDLKELGNYTYYNKWPWYIWLGFIAGLVALALCVFFILCCTGCGTNCMGKLKCNRC
CDRYEEYDLEPHKVHVH SEQ ID NO. 2 [aa377-662 of MERS-CoV S protein]:
QAEGVECDFSPLLSGTPPQVYNFKRLVFTNCNYNLTKLLSLFSVNDFTCSQISPAAIASNCYSSLILD
YFSYPLSMKSDLSVSSAGPISQFNYKQSFSNPTCLILATVPHNLTTITKPLKYSYINKCSRLLSDDRTE
VPQLVNANQYSPCVSIVPSTVWEDGDYYRKQLSPLEGGGWLVASGSTVAMTEQLQMGFGITVQY
GTDTNSVCPKLEFANDTKIASQLGNCVEYSLYGVSGRGVFQNCTAVGVRQQRFVYDAYQNLVGYY
SDDGNYYCLRACVSVPVSVI SEQ ID NO. 3 [aa377-588 of MERS-CoV S protein]:
QAEGVECDFSPLLSGTPPQVYNFKRLVFTNCNYNLTKLLSLFSVNDFTCSQISPAAIASNCYSSLILD
YFSYPLSMKSDLSVSSAGPISQFNYKQSFSNPTCLILATVPHNLTTITKPLKYSYINKCSRLLSDDRTE
VPQLVNANQYSPCVSIVPSTVWEDGDYYRKQLSPLEGGGWLVASGSTVAMTEQLQMGFGITVQY
GTDTNSVCPKL SEQ ID NO. 4 [aa350-588 of MERS-CoV S protein]:
SYESFDVESGVYSVSSFEAKPSGSVVEQAEGVECDFSPLLSGTPPQVYNFKRLVFTNCNYNLTKLL
SLFSVNDFTCSQISPAAIASNCYSSLILDYFSYPLSMKSDLSVSSAGPISQFNYKQSFSNPTCLILATV
PHNLTTITKPLKYSYINKCSRLLSDDRTEVPQLVNANQYSPCVSIVPSTVWEDGDYYRKQLSPLEGG
GWLVASGSTVAMTEQLQMGFGITVQYGTDTNSVCPKL SEQ ID NO. 5 [aa358-588 of MERS-CoV S protein]:
SGVYSVSSFEAKPSGSVVEQAEGVECDFSPLLSGTPPQVYNFKRLVFTNCNYNLTKLLSLFSVNDF
TCSQISPAAIASNCYSSLILDYFSYPLSMKSDLSVSSAGPISQFNYKQSFSNPTCLILATVPHNLTTITK
PLKYSYINKCSRLLSDDRTEVPQLVNANQYSPCVSIVPSTVWEDGDYYRKQLSPLEGGGWLVASG
STVAMTEQLQMGFGITVQYGTDTNSVCPKL SEQ ID NO. 6 [aa367-588 of MERS-CoV S protein]:
EAKPSGSVVEQAEGVECDFSPLLSGTPPQVYNFKRLVFTNCNYNLTKLLSLFSVNDFTCSQISPAAI
ASNCYSSLILDYFSYPLSMKSDLSVSSAGPISQFNYKQSFSNPTCLILATVPHNLTTITKPLKYSYINK
CSRLLSDDRTEVPQLVNANQYSPCVSIVPSTVWEDGDYYRKQLSPLEGGGWLVASGSTVAMTEQL
QMGFGITVQYGTDTNSVCPKL SEQ ID NO. 7 [aa367-606 of MERS-CoV S protein]:
EAKPSGSVVEQAEGVECDFSPLLSGTPPQVYNFKRLVFTNCNYNLTKLLSLFSVNDFTCSQISPAAI
ASNCYSSLILDYFSYPLSMKSDLSVSSAGPISQFNYKQSFSNPTCLILATVPHNLTTITKPLKYSYINK
CSRLLSDDRTEVPQLVNANQYSPCVSIVPSTVWEDGDYYRKQLSPLEGGGWLVASGSTVAMTEQL
QMGFGITVQYGTDTNSVCPKLEFANDTKIASQLGNCVEY SEQ ID NO. 8 [S350-588-Fc]:
SYESFDVESGVYSVSSFEAKPSGSVVEQAEGVECDFSPLLSGTPPQVYNFKRLVFTNCNYNLTKLL
SLFSVNDFTCSQISPAAIASNCYSSLILDYFSYPLSMKSDLSVSSAGPISQFNYKQSFSNPTCLILATV
PHNLTTITKPLKYSYINKCSRLLSDDRTEVPQLVNANQYSPCVSIVPSTVWEDGDYYRKQLSPLEGG
GWLVASGSTVAMTEQLQMGFGITVQYGTDTNSVCPKLRSDKTHTCPPCPAPELLGGPSVFLFPPK
PKDTLMISRTPEVTCVVVDVSHEDPEVKFNWYVDGVEVHNAKTKPREEQYNSTYRVVSVLTVLHQ TABLE 1-continued Amino acid sequences of MERS-CoV regions and immunopotentiators DWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLS
LSPGK SEQ ID NO. 9 [S358-588-Fc]:
SGVYSVSSFEAKPSGSVVEQAEGVECDFSPLLSGTPPQVYNFKRLVFTNCNYNLTKLLSLFSVNDF
TCSQISPAAIASNCYSSLILDYFSYPLSMKSDLSVSSAGPISQFNYKQSFSNPTCLILATVPHNLTTITK
PLKYSYINKCSRLLSDDRTEVPQLVNANQYSPCVSIVPSTVWEDGDYYRKQLSPLEGGGWLVASG
STVAMTEQLQMGFGITVQYGTDTNSVCPKLRSDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPGK SEQ ID NO. 10 [S367-588-Fc]:
EAKPSGSVVEQAEGVECDFSPLLSGTPPQVYNFKRLVFTNCNYNLTKLLSLFSVNDFTCSQISPAAI
ASNCYSSLILDYFSYPLSMKSDLSVSSAGPISQFNYKQSFSNPTCLILATVPHNLTTITKPLKYSYINK
CSRLLSDDRTEVPQLVNANQYSPCVSIVPSTVWEDGDYYRKQLSPLEGGGWLVASGSTVAMTEQL
QMGFGITVQYGTDTNSVCPKLRSDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK SEQ ID NO. 11 [S367-606-Fc]:
EAKPSGSVVEQAEGVECDFSPLLSGTPPQVYNFKRLVFTNCNYNLTKLLSLFSVNDFTCSQISPAAI
ASNCYSSLILDYFSYPLSMKSDLSVSSAGPISQFNYKQSFSNPTCLILATVPHNLTTITKPLKYSYINK
CSRLLSDDRTEVPQLVNANQYSPCVSIVPSTVWEDGDYYRKQLSPLEGGGWLVASGSTVAMTEQL
QMGFGITVQYGTDTNSVCPKLEFANDTKIASQLGNCVEYRSDKTHTCPPCPAPELLGGPSVFLFPP
KPKDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSL
SLSPGK SEQ ID NO. 12 [S377-588-Fc]:
QAEGVECDFSPLLSGTPPQVYNFKRLVFTNCNYNLTKLLSLFSVNDFTCSQISPAAIASNCYSSLILD
YFSYPLSMKSDLSVSSAGPISQFNYKQSFSNPTCLILATVPHNLTTITKPLKYSYINKCSRLLSDDRTE
VPQLVNANQYSPCVSIVPSTVWEDGDYYRKQLSPLEGGGWLVASGSTVAMTEQLQMGFGITVQY
GTDTNSVCPKLRSDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK SEQ ID NO. 13 [S377-662-Fc]:
QAEGVECDFSPLLSGTPPQVYNFKRLVFTNCNYNLTKLLSLFSVNDFTCSQISPAAIASNCYSSLILD
YFSYPLSMKSDLSVSSAGPISQFNYKQSFSNPTCLILATVPHNLTTITKPLKYSYINKCSRLLSDDRTE
VPQLVNANQYSPCVSIVPSTVWEDGDYYRKQLSPLEGGGWLVASGSTVAMTEQLQMGFGITVQY
GTDTNSVCPKLEFANDTKIASQLGNCVEYSLYGVSGRGVFQNCTAVGVRQQRFVYDAYQNLVGYY
SDDGNYYCLRACVSVPVSVIRSDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKS
LSLSPGK SEQ ID NO. 14 [Foldon (Fd)]:
GYIPEAPRDGQAYVRKDGEWVLLSTFL SEQ ID NO. 15 [human IgG Fc (hFc)]:
RSDKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSR
WQQGNVFSCSVMHEALHNHYTQKSLSLSPGK SEQ ID NO. 16 [mouse IgG Fc (mFc)]:
RSPRGPTIKPCPPCKCPAPNLLGGPSVFIFPPKIKDVLMISLSPIVTCVVVDVSEDDPDVQISWFVNN
VEVHTAQTQTHREDYNSTLRVVSALPIQHQDWMSGKEFKCKVNNKDLPAPIERTISKPKGSVRAPQ
VYVLPPPEEEMTKKQVTLTCMVTDFMPEDIYVEWTNNGKTELNYKNTEPVLDSDGSYFMYSKLRV
EKKNWVERNSYSCSVVHEGLHNHHTTKSFSRTPGK SEQ ID NO. 17 [rabbit IgG Fc (rFc)]:
RSSKPTCPPPELLGGPSVFIFPPKPKDTLMISRTPEVTCVVVDVSQDDPEVQFTWYINNEQVRTAR
PPLREQQFNSTIRVVSTLPIAHQDWLRGKEFKCKVHNKALPAPIEKTISKARGQPLEPKVYTMGPPR
EELSSRSVSLTCMINGFYPSDISVEWEKNGKAEDNYKTTPAVLDSDGSYFLYSKLSVPTSEWQRGD
VFTCSVMHEALHNHYTQKSISRSPGK SEQ ID NO. 18 [Human C3d (aa residues 1002-1303 in C3)]:
HLIVTPSGCGEQNMIGMTPTVIAVHYLDETEQWEKFGLEKRQGALELIKKGYTQQLAFRQPSSAFA
AFVKRAPSTWLTAYVVKVFSLAVNLIAIDSQVLCGAVKWLILEKQKPDGVFQEDAPVIHQEMIGGLR
NNNEKDMALTAFVLISLQEAKDICEEQVNSLPGSITKAGDFLEANYMNLQRSYTVAIAGYALAQMGR TABLE 1-continued Amino acid sequences of MERS-CoV regions and immunopotentiators LKGPLLNKFLTTAKDKNRWEDPGKQLYNVEATSYALLALLQLKDFDFVPPVVRWLNEQRYYGGGY
GSTQATFMVFQALAQYQKDAPDHQELNLDVSLQLPSR SEQ ID NO. 19 [Cholera toxin b subunit (aa residues 1-124)]:
MTPQNITDLCAEYHNTQIHTLNDKIFSYTESLAGKREMAIITFKNGATFQVEVPGSQHIDSQKKAIER
MKDTLRIAYLTEAKVEKLCVWNNKTPRAIAAISMAN SEQ ID NO. 25 [aa377-588 of MERS-CoV S protein with T579N mutation]:
QAEGVECDFSPLLSGTPPQVYNFKRLVFTNCNYNLTKLLSLFSVNDFTCSQISPAAIASNCYSSLILD
YFSYPLSMKSDLSVSSAGPISQFNYKQSFSNPTCLILATVPHNLTTITKPLKYSYINKCSRLLSDDRTE
VPQLVNANQYSPCVSIVPSTVWEDGDYYRKQLSPLEGGGWLVASGSTVAMTEQLQMGFGITVQY
GNDTNSVCPKL SEQ ID NO. 26 [S377-588-Fc with T579N mutation]:
QAEGVECDFSPLLSGTPPQVYNFKRLVFTNCNYNLTKLLSLFSVNDFTCSQISPAAIASNCYSSLILD
YFSYPLSMKSDLSVSSAGPISQFNYKQSFSNPTCLILATVPHNLTTITKPLKYSYINKCSRLLSDDRTE
VPQLVNANQYSPCVSIVPSTVWEDGDYYRKQLSPLEGGGWLVASGSTVAMTEQLQMGFGITVQY
GNDTNSVCPKLRSDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK Optionally, a trimerization stabilization sequence is disposed between the MERS-CoV sequence and the immunopotentiator. In one embodiment, the stabilization sequence comprises a sequence that stabilizes the RGB protein sequence in a trimer or oligomer configuration. As used herein, the terms stabilization sequence, trimeric motif, and trimerization sequence are interchangeable and equivalent. Suitable stabilization sequences include, but are not limited to, a 27 amino acid region of the C-terminal domain of T4 fibritin (a foldon-like sequence) (GYIPEAPRDGQAY-VRKDGEWVLLSTFL, SEQ ID NO. 14 or GSGYIPEAPRDGQAYVRKDGE WVLLSTFL, SEQ ID NO. 20), a GCN4 (MKQIEDKIEEILSKIYHIENEIARIK-KLIGEV; SEQ ID NO. 21), an IQ (RMKQIEDKIEE-IESKQKKIENEIARIKK; SEQ ID NO. 22), or an IZ (IK-KEIEAIKKEQEAI KKKIEAIEK; SEQ ID NO. 23). Other suitable stabilization methods include, but are not limited to, 2,2-bipyridine-5-carboxylic acid (BPY), disulfide bonds and facile ligation.

In another embodiment, the immunopotentiator comprises a sequence to enhance the immunogenicity of the immunogenic composition. Suitable immunopotentiators include, but are not limited to, an Fc fragment of human IgG, a C3d (a complement fragment that promotes antibody formation binding to antigens enhancing their uptake by dendritic cells and B cells) (SEQ ID NO:18), an Ov ASP-1 (*Onchocerca volvulus* homologue of the activation associated secreted gene family) (see US 20060039921, which is incorporated by reference herein for all it discloses regarding ASP-1 adjuvants), a cholera toxin (SEQ ID NO:19), a muramyl peptide, and a cytokine.

In one embodiment, the immunopotentiator is an immunoglobulin Fc fragment. The immunoglobulin molecule consists of two light (L) chains and two heavy (H) chains held together by disulfide bonds such that the chains form a Y shape. The base of the Y (carboxyl terminus of the heavy chain) plays a role in modulating immune cell activity. This region is called the Fc region, and is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils, and eosinophils.

Figure 1:
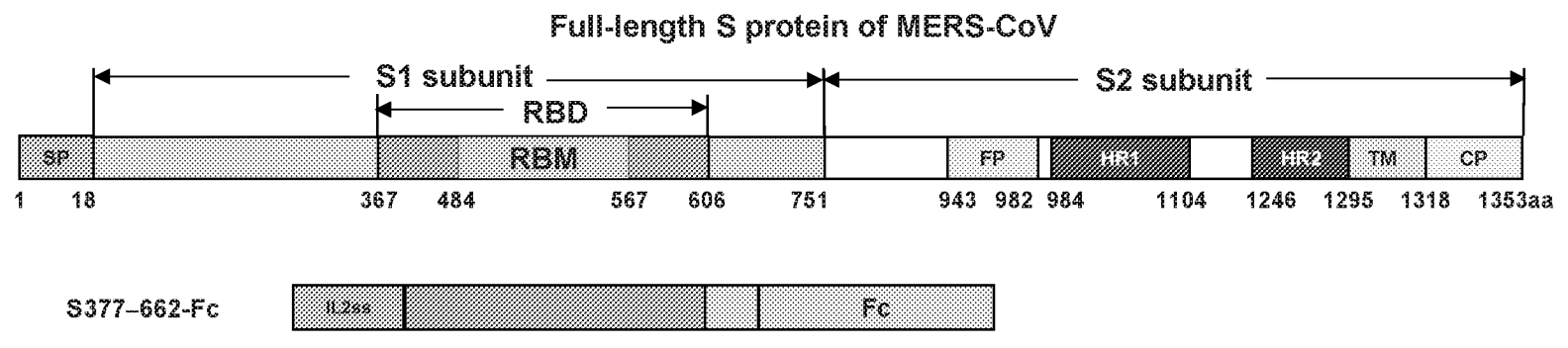

Exemplary subunit MERS-CoV immunogenic compositions are found in FIG. 1. In certain embodiments, the coronavirus and immunopotentiator portions of the fusion protein are linked through a flexible linker comprising $(GGGGS)_n$ (SEQ ID NO:24), wherein n is an integer between 0 and 8. In certain embodiments, n is 0, n is 1, n is 2, n is 3, n is 4, n is 5, n is 6, n is 7, or n is 8.

The disclosed MERS-CoV immunogenic compositions include conservative variants of the proteins. A conservative variant refers to a peptide or protein that has at least one amino acid substituted by another amino acid, or an amino acid analog, that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative substitution can be assessed by a variety of factors, such as, e.g., the physical properties of the amino acid being substituted (Table 1) or how the original amino acid would tolerate a substitution (Table 2). The selections of which amino acid can be substituted for another amino acid in a peptide disclosed herein are known to a person of ordinary skill in the art. A conservative variant can function in substantially the same manner as the exemplary reference peptide, and can be substituted for the exemplary reference peptide in any aspect of the present specification.

TABLE 1

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |

TABLE 1-continued

Amino Acid Properties

| Property | Amino Acids |
| --- | --- |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
| --- | --- | --- | --- |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

An MERS-CoV immunogenic composition can also comprise conservative variants to the disclosed proteins. In aspects of this embodiment, a conservative variant of an MERS-CoV immunogenic composition can be, for example, an amino acid sequence having at least 75%, at least 80%, at least 85%, at least 90%, at least 95%, at least 97%, at least 98%, or at least 99% amino acid sequence identity to the MERS-CoV immunogenic compositions disclosed herein. In other aspects of this embodiment, a conservative variant of an MERS-CoV immunogenic composition can be, for example, an amino acid sequence having at most 75%, at most 80%, at most 85%, at most 90%, at most 95%, at most 97%, at most 98%, or at most 99% amino acid sequence identity to the MERS-CoV immunogenic compositions disclosed herein.

In other embodiments, the MERS-CoV S protein sequence comprises an amino acid sequence having at least 75%, at least 80%, at least 85%, at least 90%, at least 95%, at least 97%, at least 98%, or at least 99% amino acid sequence identity to the MERS-CoV S amino acid sequences of any of SEQ ID NOs. 1-7.

In still other embodiments, the immunopotentiator sequence comprises an amino acid sequence having at least 75%, at least 80%, at least 85%, at least 90%, at least 95%, at least 97%, at least 98%, or at least 99% amino acid sequence identity to the immunopotentiator amino acid sequences of any of SEQ ID NOs. 9-11, 17 or 18.

In other aspects of this embodiment, a conservative variant of an MERS-CoV immunogenic composition, a MERS-CoV S protein amino acid sequence, or an immunopotentiator amino acid sequence can have, for example, 1, 2, 3, 4, 5, 6, 7, 8, 9, 10, 11, 12, 13, 14, 15, or more conservative substitutions, to the amino acid sequence of the MERS-CoV immunogenic compositions, MERS-CoV S protein, or immunopotentiator disclosed herein. In other aspects of this embodiment, a conservative variant of an MERS-CoV immunogenic composition, a MERS-CoV S protein amino acid sequence, or an immunopotentiator amino acid sequence can be, for example, an amino acid sequence having at least 1, at least 2, at least 3, at least 4, at least 5, at least 6, at least 7, at least 8, at least 9, at least 10, at least 11, at least 12, at least 13, at least 14, or at least 15 conservative substitutions to the amino acid sequence of the MERS-CoV immunogenic compositions, MERS-CoV S protein, or immunopotentiator disclosed herein. In yet other aspects of this embodiment, a conservative variant of an MERS-CoV immunogenic composition, a MERS-CoV S protein amino acid sequence, or an immunopotentiator amino acid sequence can be, for example, an amino acid sequence having at most 1, at most 2, at most 3, at most 4, at most 5, at most 6, at most 7, at most 8, at most 9, at most 10, at most 11, at most 12, at most 13, at most 14, or at most 15 conservative substitutions to the amino acid sequence of the MERS-CoV immunogenic compositions, MERS-CoV S protein, or immunopotentiator disclosed herein. In further aspects of this embodiment, a conservative variant of an MERS-CoV immunogenic composition, a MERS-CoV S protein amino acid sequence, or an immunopotentiator amino acid sequence can be, for example, an amino acid sequence having from 1 to 15, 2 to 15, 3 to 15, 4 to 15, 5 to 15, 6 to 15, 7 to 15, 1 to 12, 2 to 12, 3 to 12, 4 to 12, 5 to 12, 6 to 12, 7 to 12, 1 to 10, 2 to 10, 3 to 10, 4 to 10, 5 to 10, 6 to 10, 7 to 10, 1 to 8, 2 to 8, 3 to 8, 4 to 8, 5 to 8, 6 to 8, 1 to 6, 2 to 6, 3 to 6, 4 to 6, 1 to 4, 2 to 4, or 1 to 3 conservative substitutions to the amino acid sequence of the MERS-CoV immunogenic compositions, MERS-CoV S protein, or immunopotentiator disclosed herein.

Expression systems such as the following are suitable for use in expressing the disclosed fusion proteins: mammalian cell expression systems such as, but not limited to, the pcDNA and GS Gene expression systems; insect cell expression systems such as, but not limited to, Bac-to-Bac, baculovirus, and DES expression systems; and *E. coli* expression systems including, but not limited to, pET, pSUMO, and GST expression systems.

Various advantages are associated with expression of proteins in mammalian cell expression systems. The mammalian cell expression system is a relatively mature eukaryotic system for expression of recombinant proteins. It is more likely to achieve a correctly folded soluble protein with proper glycosylation, making the expressed protein maintain its native conformation and keep sufficient bioactivity. This system can either transiently or stably express recombinant antigens, and promote signal synthesis. Recombinant proteins expressed in this way may maintain proper antigenicity and immunogenicity. However, both insect and bacterial expression systems provide inexpensive and efficient expression of proteins, which may be appropriate under certain conditions.

The purification systems used to purify the recombinant proteins are dependent on whether a tag is linked or fused with the coronavirus sequence. If the fusion proteins are fused with IgG Fc, Protein A, or Protein G, affinity chromatography is used for the purification. If the fusion proteins are fused with GST proteins, the GST columns will be used for the purification. If the fusion proteins link with 6×His tag at the N- or C-terminal, the expressed proteins are to be purified using His tag columns. If no tag is linked with the fusion protein, the expressed protein could be purified using fast protein liquid chromatography (FPLC), high performance liquid chromatography (HPLC), or other chromatography.

In certain embodiments, the immunogenic compositions further comprise or are administered with an adjuvant. Adjuvants suitable for use in animals include, but are not limited to, Freund's complete or incomplete adjuvants, Sigma Adjuvant System (SAS), and Ribi adjuvants. Adjuvants suitable for use in humans include, but are not limited to, MF59 (an oil-in-water emulsion adjuvant); Montanide ISA 51 or 720 (a mineral oil-based or metabolizable oil-based adjuvant); aluminum hydroxide, -phosphate, or -oxide; HAVLOGEN® (an acrylic acid polymer-based adjuvant, Intervet Inc., Millsboro, Del.); polyacrylic acids; oil-in-water or water-in-oil emulsion based on, for example a mineral oil, such as BAYOL™ or MARCOL™ (Esso Imperial Oil Limited, Canada), or a vegetable oil such as vitamin E acetate; saponins; and Onchocerca volvulus activation-associated protein-1 (Ov ASP-1) (see US 20060039921, which is incorporated by reference herein for all it discloses regarding Ov ASP-1 adjuvants). However, components with adjuvant activity are widely known and, generally, any adjuvant may be utilized that does not adversely interfere with the efficacy or safety of the vaccine and/or immunogenic composition.

Vaccines and/or immunogenic compositions according to the various embodiments disclosed herein can be prepared and/or marketed in the form of a liquid, frozen suspension, or in a lyophilized form. Typically, vaccines and/or immunogenic compositions prepared according to the present disclosure contain a pharmaceutically acceptable carrier or diluent customarily used for such compositions. Carriers include, but are not limited to, stabilizers, preservatives, and buffers. Suitable stabilizers are, for example SPGA, Tween compositions (such as are available from A.G. Scientific, Inc., San Diego, Calif.), carbohydrates (such as sorbitol, mannitol, starch, sucrose, dextran, glutamate, or glucose), proteins (such as dried milk serum, albumin, or casein), or degradation products thereof. Examples of suitable buffers include alkali metal phosphates. Suitable preservatives include thimerosal, merthiolate, and gentamicin. Diluents include water, aqueous buffer (such as buffered saline), alcohols, and polyols (such as glycerol).

Also disclosed herein are methods for inducing an immune response to a MERS-CoV using the disclosed proteins. Generally, the vaccine and/or immunogenic composition may be administered subcutaneously, intradermally, submucosally, intranasally, or intramuscularly in an effective amount to prevent infection from the MERS-CoV and/or treat an infection from the MERS-CoV. An effective amount to prevent infection is an amount of immunizing protein that will induce immunity in the immunized animals against challenge by a virulent virus such that infection is prevented or the severity is reduced. Immunity is defined herein as the induction of a significant higher level of protection in a subject after immunization compared to an unimmunized group. An effective amount to treat an infection is an amount of immunizing protein that induces an appropriate immune response against MERS-CoV such that severity of the infection is reduced.

Protective immune responses can include humoral immune responses and cellular immune responses. Protection against MERS-CoV is believed to be conferred through serum antibodies (humoral immune response) directed to the surface proteins, with mucosal IgA antibodies and cell-mediated immune responses also playing a role. Cellular immune responses are useful in protection against MERS-CoV virus infection with CD4+ and CD8+ T cell responses being particularly important. CD8+ immunity is of particular importance in killing virally infected cells.

Additionally, the disclosed proteins and/or immunogenic compositions can be administered using immunization schemes known by persons of ordinary skill in the art to induce protective immune responses. These include a single immunization or multiple immunizations in a prime-boost strategy. A boosting immunization can be administered at a time after the initial, prime, immunization that is days, weeks, months, or even years after the prime immunization. In certain embodiments, a boost immunization is administered 2 weeks, 1 month, 2, months, 3 months, 4 months, 5 months, or 6 months or more after the initial prime immunization. Additional multiple boost immunizations can be administered such as weekly, every other week, monthly, every other month, every third month, or more. In other embodiments, the boost immunization is administered every 3 weeks, every 4 weeks, every 5 weeks, every 6 weeks, every 7 weeks, every 8 weeks, every 9 weeks, every 10 weeks, every 11 weeks, or every 12 weeks. In certain embodiments, boosting immunizations can continue until a protective anti-MERS-CoV antibody titer is seen in the subject's serum. In certain embodiments, a subject is given one boost immunization, two boost immunizations, three boost immunizations, or four or more boost immunizations, as needed to obtain a protective antibody titer. In other embodiments, the adjuvant in the initial prime immunization and the adjuvant in the boost immunizations are different.

Further, in various formulations of the proteins and/or immunogenic compositions, suitable excipients, stabilizers, and the like may be added as are known by persons of ordinary skill in the art.

The disclosed proteins, immunogenic compositions, and methods may be used to prevent MERS-CoV virus infection in a subject susceptible thereto such as, but not limited to, a human, a primate, a domesticated animal, an animal in the wild, or a bird.

EXAMPLES

Example 1

Materials and Methods

Construction, Expression, and Purification of Recombinant Proteins.

The construction, expression, and purification of the recombinant protein fused with Fc (S350-588-Fc, S358-588-Fc, S367-588-Fc, S367-606-Fc, S377-588-Fc, and S377-662-Fc) were done as follows. Briefly, genes encoding residues 350-588, 358-588, 367-588, 367-606, 377-588, or 377-662 of MERS-CoV S protein were amplified by PCR using synthesized codon-optimized MERS-CoV S sequences (GenBank: AFS88936.1) as the template. These fragments were then digested by EcoRI and BglII restriction enzymes and inserted into the pFUSE-hIgG1-Fc2 expression vector (hereinafter named Fc). The sequence-confirmed recombinant plasmids were respectively transfected into 293T cells which had been seeded 24 hr before transfection, followed by replacing culture medium with serum-free DMEM 8-10 hr later, and collection of supernatant containing expressed protein 72 hr post-transfection. The recombinant S350-588-Fc, S358-588-Fc, S367-588-Fc, S367-606-Fc, S377-588-Fc, and S377-662-Fc proteins were then purified by Protein A affinity chromatography.

SDS-PAGE and Western Blot.

The purified proteins were analyzed by SDS-PAGE and Western blot. Briefly, the proteins were either boiled at 95° C. for 5 min or not boiled, and separated by 10% Tris-Glycine gel. The proteins were then stained with Coomassie Blue or transferred to nitrocellulose membranes for Western blot analysis. After blocking with 5% non-fat milk in PBST overnight at 4° C., the blots were incubated for 1 hr at room temperature with MERS-CoV S1-specific polyclonal antibodies (1:1,000). After three washes, the blots were then incubated with horseradish peroxidase (HRP)-conjugated goat anti-mouse IgG (1:5,000) for 1 hr at room temperature. Signals were visualized with ECL Western blot substrate reagents and Amersham Hyperfilm.

Mouse Immunization and Sample Collection.

Mice were prime-immunized s.c. with 10 μg/mouse of recombinant S350-588-Fc, S358-588-Fc, S367-588-Fc, S367-606-Fc, S377-588-Fc, or S377-662-Fc protein formulated with Montanide ISA 51 adjuvant, or i.n. with 10 μg/mouse of recombinant S377-662-Fc formulated with poly(I:C) adjuvant. Both groups were boosted with 10 μg/mouse of the same immunogen and adjuvant at 3-week intervals. Sera were collected at 10 days post-last immunization to detect MERS-CoV S1-specific IgG antibodies and neutralizing antibodies.

ELISA.

Collected mouse sera were analyzed for MERS-CoV or SARS-CoV S-specific antibody responses by ELISA. Briefly, 96-well ELISA plates were respectively precoated with recombinant proteins overnight at 4° C. and blocked with 2% non-fat milk for 2 hr at 37° C. Serially diluted mouse sera or monoclonal antibodies (mAbs) were added to the plates and incubated at 37° C. for 1 hr, followed by four washes. Bound antibodies were incubated with HRP-conjugated goat anti-mouse IgG (1:2,000) for 1 hr at 37° C. The reaction was visualized by substrate 3,3',5,5'-tetramethyl-benzidine (TMB) and stopped by 1 N $H_2SO_4$. The absorbance at 450 nm (A450) was measured by ELISA plate reader.

Live Virus-Based Neutralization Assay.

Neutralizing antibody titers of mouse sera against infection by live MERS-CoV or SARS-CoV were further detected as described below. Briefly, serial 2-fold dilutions of mouse sera or mAbs were incubated with 100 $TCID_{50}$ (50% tissue culture infective dose) of MERS-CoV or SARS-CoV for 1 hr at 37° C. prior to addition to a monolayer of fetal rhesus monkey kidney (FRhK4) cells for SARS-CoV and Vero E6 cells for MERS-CoV in triplicate. Virus supernatant was removed and replaced with fresh medium after 1 hr of culture at 37° C. The cytopathic effect (CPE) in each well was observed daily and recorded on day 3 post-infection. The neutralizing titers of mouse antisera that completely prevented CPE in 50% of the wells ($NT_{50}$) were calculated.

Pseudovirus-Based Neutralization Assay.

An MERS-CoV pseudovirus neutralization assay was also established for detection of neutralizing activity induced by MERS-CoV RBD-Fc protein-immunized mouse sera against MERS-CoV infection. Briefly, a plasmid expressing codon-optimized MERS-CoV (hCoV-EMC, GenBank: AFS88936.1) genes was cotransfected with a plasmid encoding Env-defective, luciferase-expressing HIV-1 genome (pNL4-3.luc.RE) into 293T cells to collect pseudovirus in supernatants. Pseudovirus-containing supernatant was incubated with serially diluted mouse sera at 37° C. for 1 hr before adding to the target Huh-7 cells. Fresh medium was added 24 hr later, and the culture was continued for 72 hr. Cells were lysed by cell lysis buffer and transferred to 96-well luminometer plates. Luciferase substrate was added, and relative luciferase activity was determined by Ultra 384 luminometer. The neutralization of MERS-CoV S pseudovirus was presented as $NT_{50}$.

Results

Figure 2:
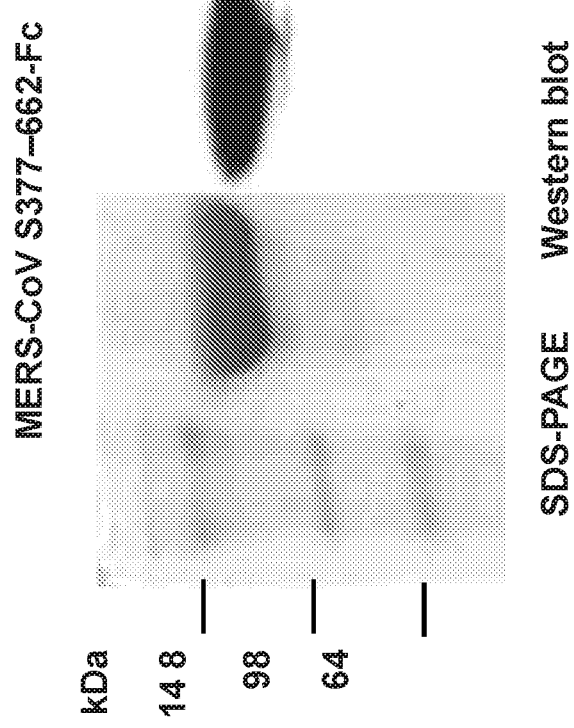
FIG. 2 depicts the SDS-PAGE and Western blot analysis of the expressed protein S377-662-Fc. The protein molecular weight marker (kDa) is indicated on the left. Antisera from mice immunized with S377-662-Fc were used for Western blot analysis.
Figure 3:
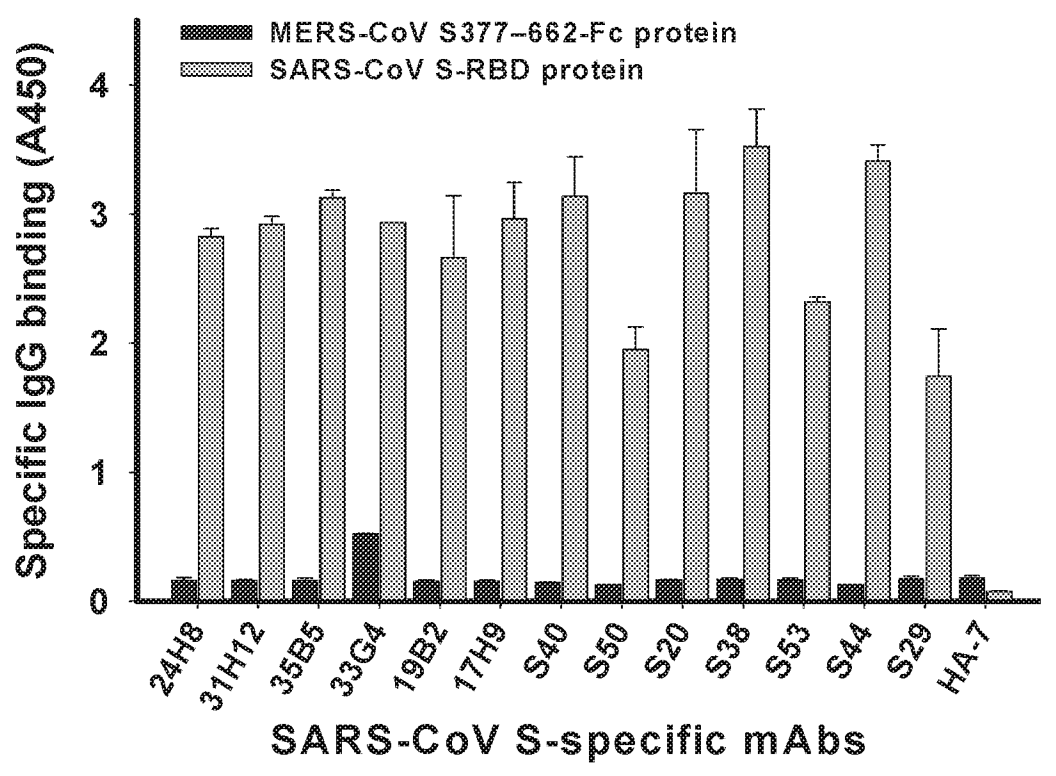

MERS-CoV S protein was expressed and its reactivity was tested with a variety of SARS-CoV S protein-specific monoclonal antibodies (mAbs) including 24H8, 31H12, 35B5, 33G4, 19B2, 17H9, S40, S50, S20, S38, S53, S44, and S29 (He, et al., J. Immunol. 174:4908-15, 2005; He, et al., Vaccine 24:5498-508, 2006, which are incorporated by reference herein for all they disclose regarding SARS-CoV S protein-specific MAbs). An antibody to the HA1 domain of influenza H5N1 virus, HA-7, was used as a control. Purified S377-662-Fc protein was expressed in soluble forms in the culture supernatant of transfected 293T cells, maintaining high expression with good purity (FIG. 2, left). This protein could be recognized by MERS-CoV S1-specific polyclonal antibodies, as detected by Western blot (FIG. 2, right). The expressed S377-662-Fc has a lower OD450 value (most antibodies have an OD450 value less 0.2) when tested by ELISA using 5-specific SARS mAbs, with similar reactivity to the control HA-7 mAb (FIG. 3). These data suggest that S377-662-Fc is highly specific to the S protein of MERS-CoV, and that it maintains lower or no cross-reactivity with the majority of SARS-CoV S-specific mAbs.

Figures 4A, 4B:
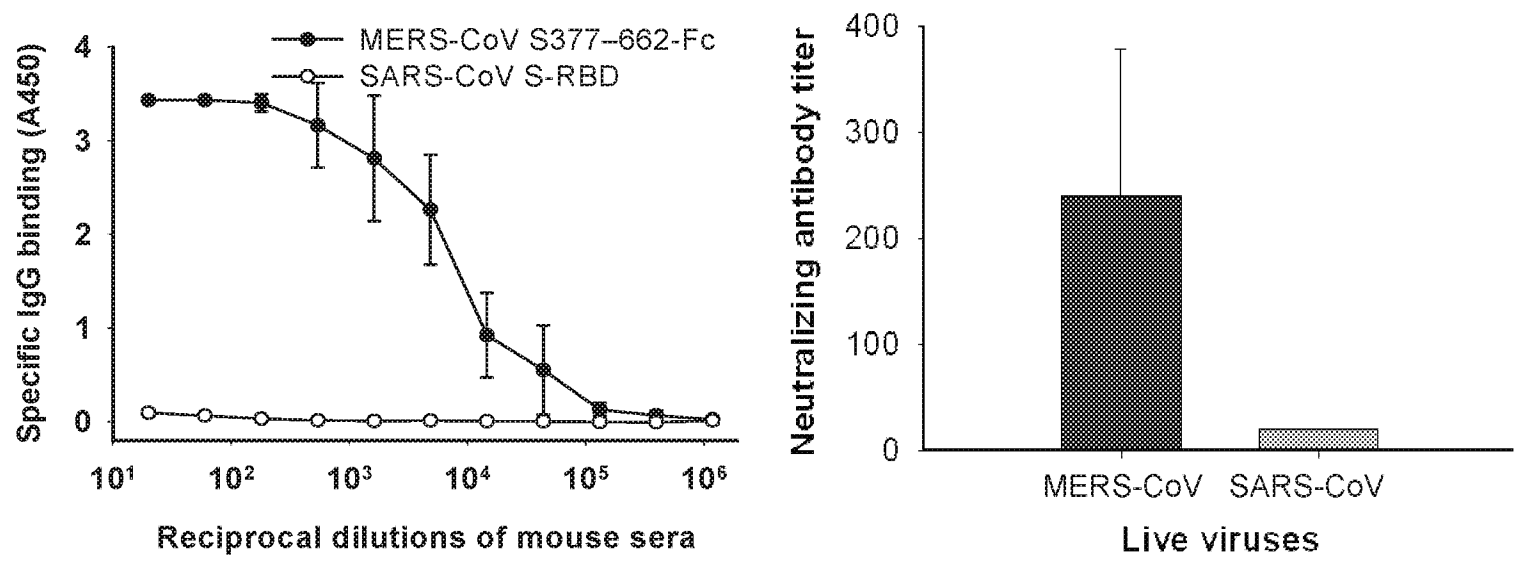

Next, the ability of expressed MERS-CoV S377-662-Fc protein to induce antibody responses, particularly neutralizing antibodies, was tested, and the ability of S377-662-Fc to elicit cross-reactivity and cross-neutralizing activity with SARS-CoV was evaluated. Mice were immunized with MERS-CoV S377-662-Fc, and then mouse sera were collected for the detection. MERS-CoV S377-662-Fc induced IgG antibodies against the S protein of MERS-CoV after the $2^{nd}$ dose of immunogenic composition, which was confirmed by coating of the ELISA plates with an MERS-CoV S-specific protein not fused to Fc (MERS-CoV S377-662) (FIG. 4A). The MERS-CoV S-specific antibodies have low or no reactivity with a recombinant RBD protein of SARS-CoV used in development of a subunit SARS candidate vaccine (FIG. 4A). Nevertheless, the anti-MERS-CoV-S antibodies could neutralize live MERS-CoV infection in cell cultures in vitro, as detected by a MERS-CoV neutralization assay (FIG. 4B). However, the ability of the MERS-CoV S-specific antibodies to neutralize live SARS-CoV infection is very low (<1:40). The above data suggest that MERS-CoV has low to no cross-reactivity and cross-neutralizing activity with SARS-CoV.

Figure 5:
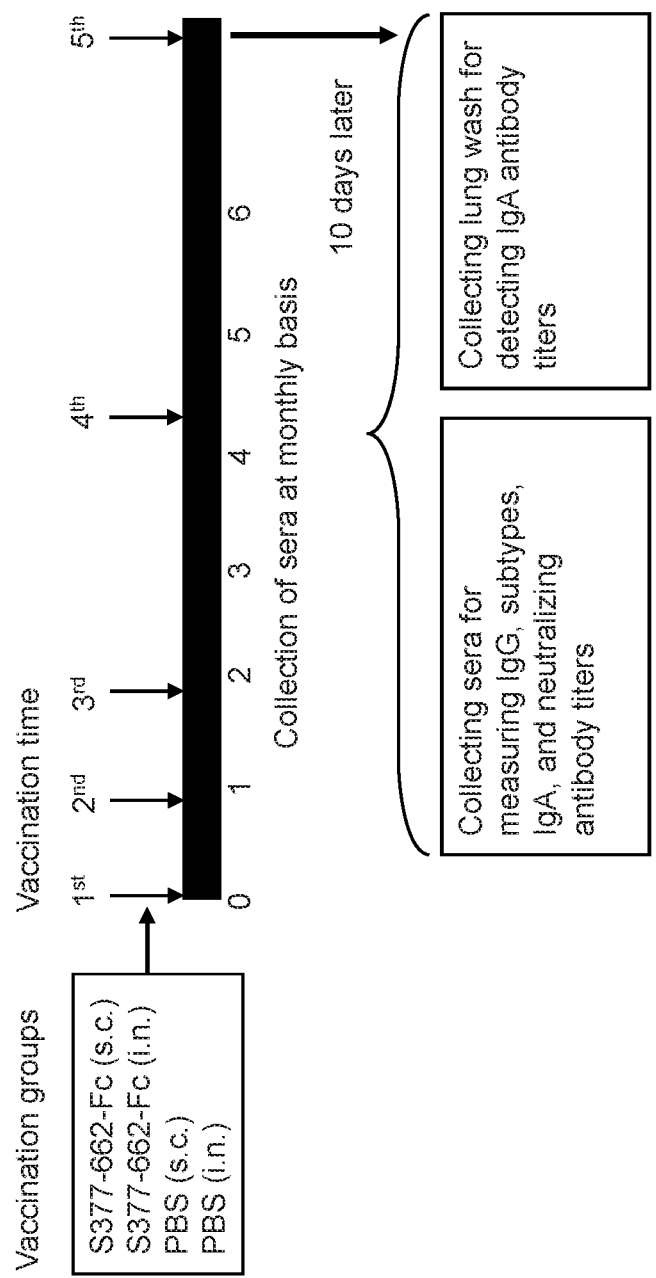
FIG. 5 depicts mouse immunization, sample collection, and immune response detection strategy. Four groups of mice were immunized subcutaneously (s.c.) or intranasally (i.n.) with MERS-CoV S377-662-Fc protein plus Montanide ISA51 (for s.c.) or poly(I:C) (for i.n.) adjuvant, or with PBS plus the corresponding adjuvant as their respective controls. Mouse sera and lung wash were collected as indicated and analyzed for humoral and mucosal immune responses and neutralization against MERS-CoV virus.
Figure 6B:
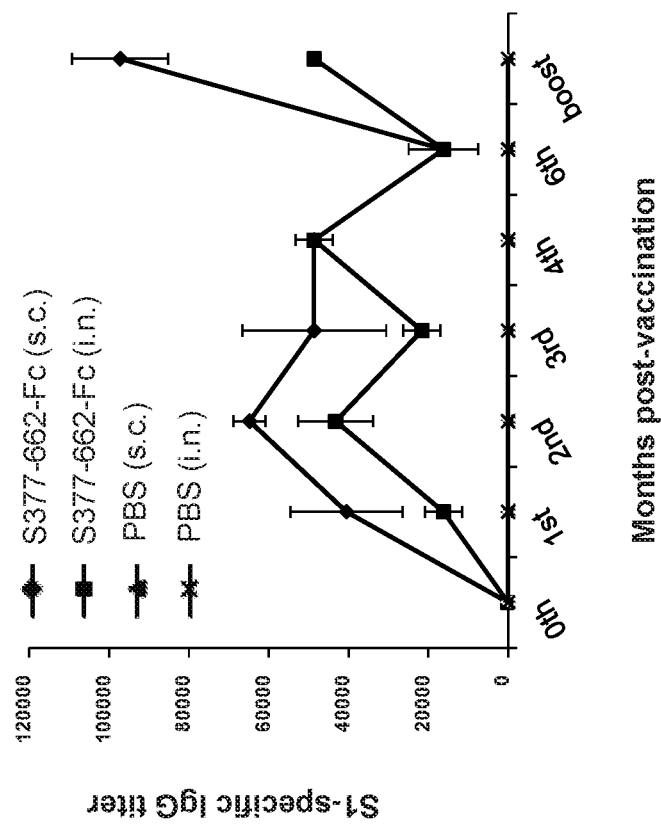
FIG. 6A and FIG. 6B depict the IgG antibody responses in sera of mice immunized (s.c. and i.n.) with MERS-CoV S377-662-Fc protein.
Figure 6A:
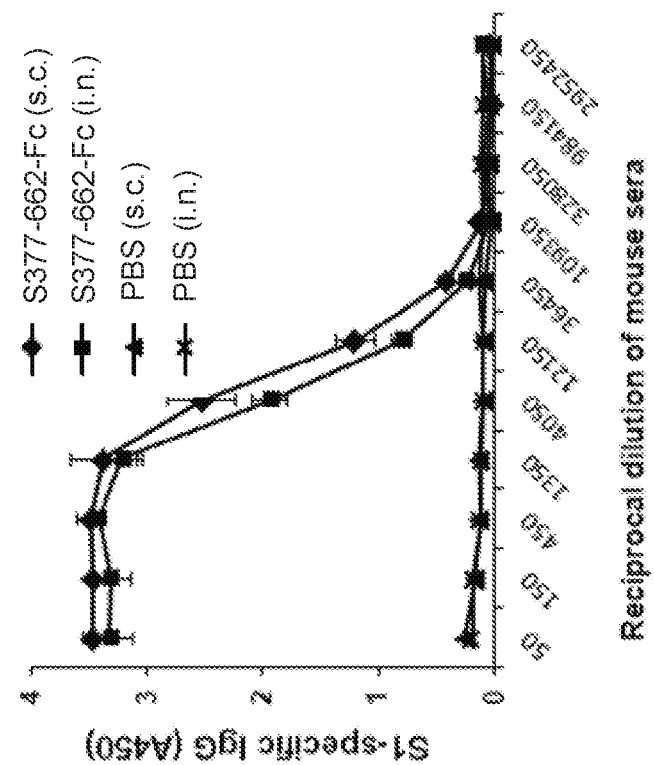
Figure 7B:
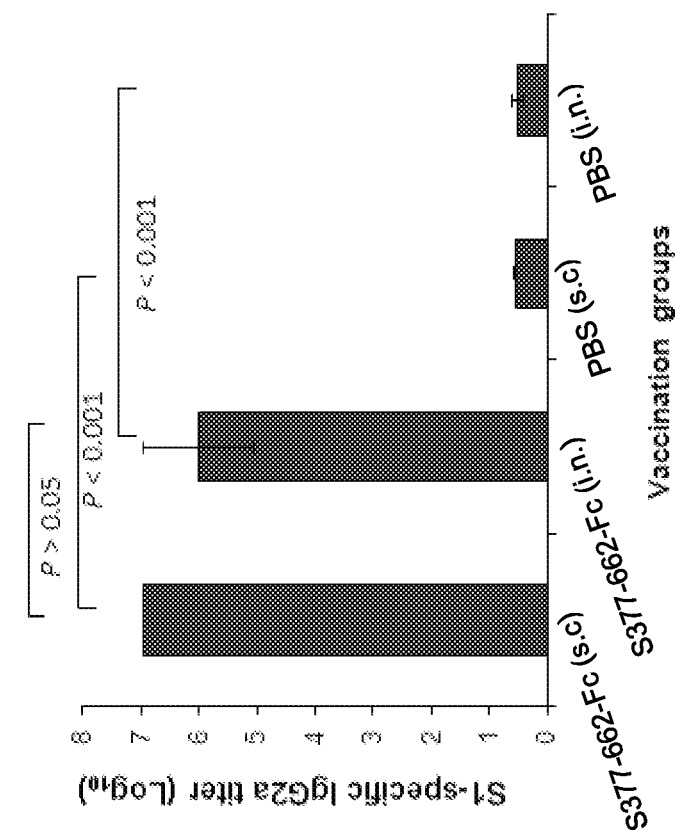
FIG. 7A and FIG. 7B depict the IgG subtypes in sera of mice immunized (s.c. and i.n.) with MERS-CoV S377-662-Fc protein. Binding of IgG1 (FIG. 7A) and IgG2a (FIG. 7B) to MERS-CoV S1-His protein is shown. Sera from 10 days post-last immunization were used for the detection, and the data are presented as geometric mean titer (GMT, endpoint titers)±SD of five mice per group. $P<0.001$ indicates significant difference.
Figure 7A:
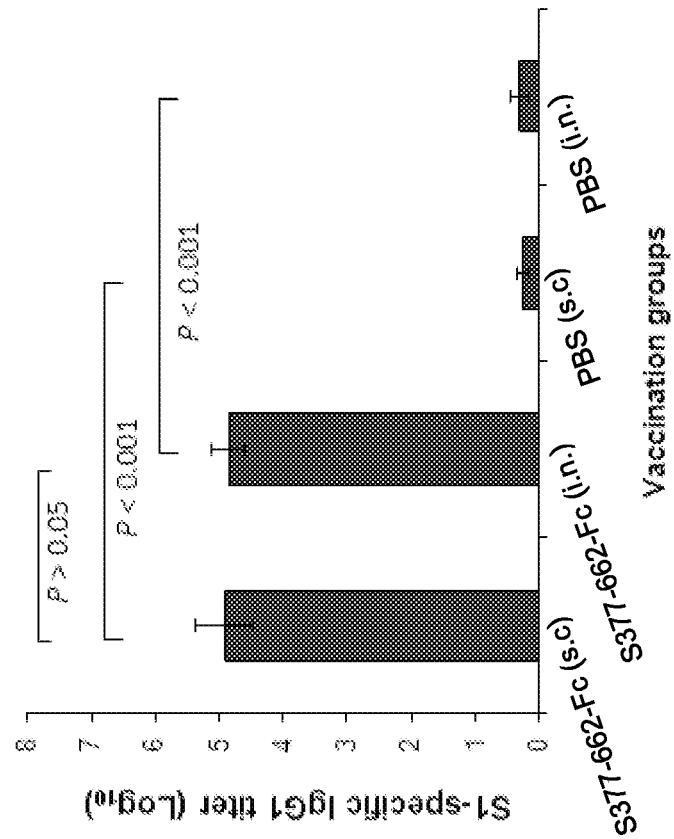
Figure 8B:
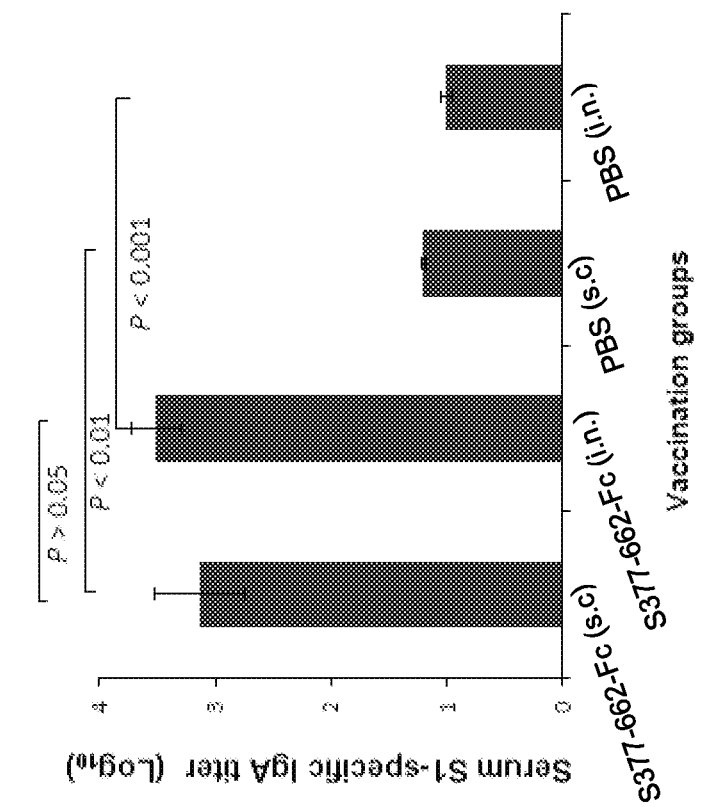
FIG. 8A and FIG. 8B depict the IgA antibody responses in lung wash and sera of mice immunized (s.c. and i.n.) with MERS-CoV S377-662-Fc protein. Binding of IgA in lung wash (1:1,000) (FIG. 8A) or sera (FIG. 8B) to MERS-CoV S1-His protein is shown. Samples from 10 days post-last immunization were used for the detection, and the data are presented as mean A450±SD (lung wash) or mean (GMT endpoint titers)±SD (sera) of five mice per group. $P<0.05$ indicates significant difference.
Figure 8A:
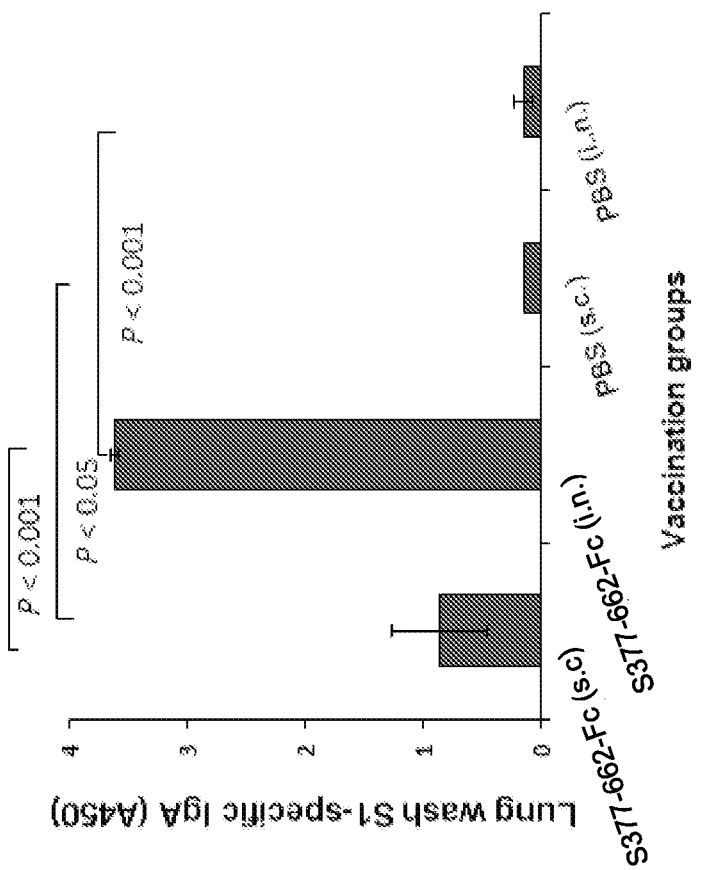

The systemic and mucosal immune responses induced by MERS-CoV RBD-Fc protein were further evaluated by immunizing mice with S377-662-Fc protein via the i.n. and s.c. immunization routes, and then detecting MERS-CoV S-specific IgG and IgA antibodies in immunized mouse sera and lung wash (FIG. 5). Indeed, sera from mice immunized via both administration routes could bind specifically to MERS-CoV S1-His protein, with the i.n. pathway inducing strong systemic humoral IgG antibody response similar to that of s.c. immunization (FIG. 6A). In addition, like the s.c. route, i.n. immunization with S377-662-Fc was able to stimulate long-term humoral immune responses in immunized mice through multiple boost immunizations, capable of maintaining protection for at least 6 months during the detection period (FIG. 6B). Furthermore, MERS-CoV S1-specific IgG1 (Th2-associated) and IgG2a (Th1-associated) antibody responses induced by the i.n. pathway were similar to those by the s.c. immunization (P>0.05), with a relatively higher level of IgG2a (Th1-associated) than IgG1 (Th2-associated) antibody against MERS-CoV S1 protein (FIG. 7), suggesting that MERS-CoV S377-662-Fc induced a slightly biased Th1-associated antibody response. Importantly, the i.n. immunization pathway induced similarly high level of IgA antibody to the s.c. route with equally strong neutralizing antibody responses against MERS-CoV in immunized mouse sera (P>0.05) (FIGS. 8B and 9A), but with a significantly higher level of IgA antibody with neutralizing activity than the s.c. route in mouse lungs (FIGS. 8A and 9B), indicating the ability of MERS-CoV S377-662-Fc protein in the induction of strong local mucosal immune response.

Figures 10A, 10B:
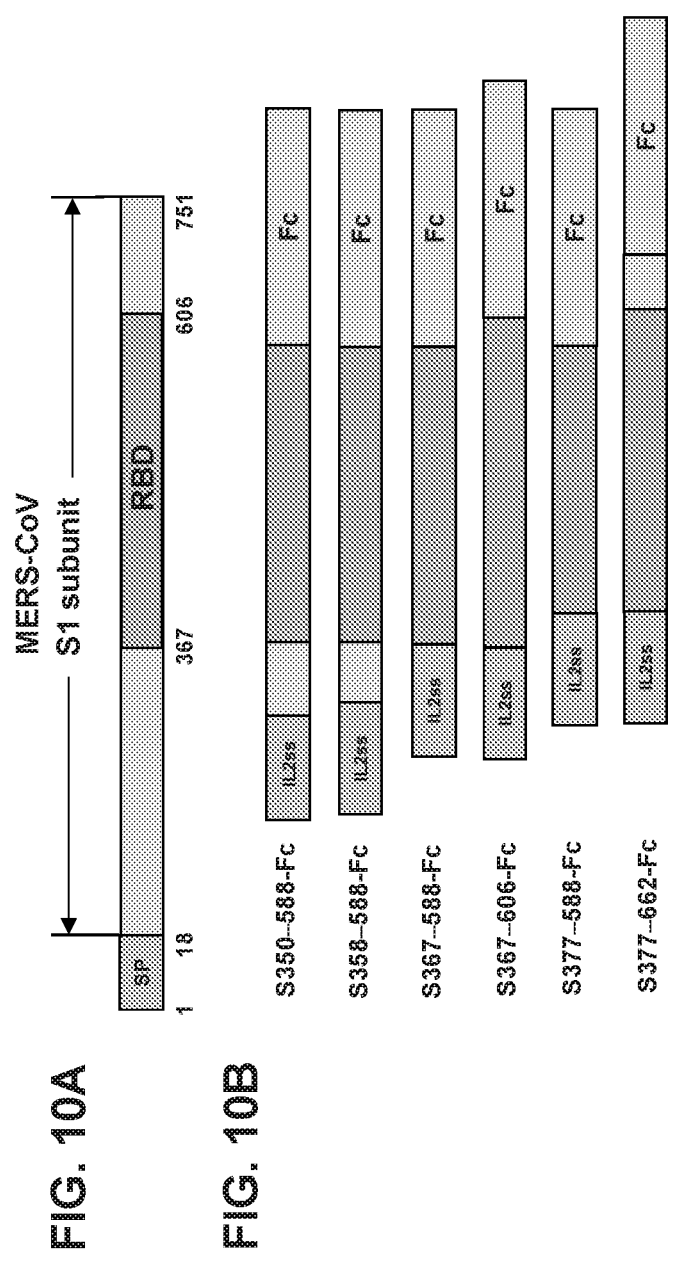
Figures 11A, 11B:
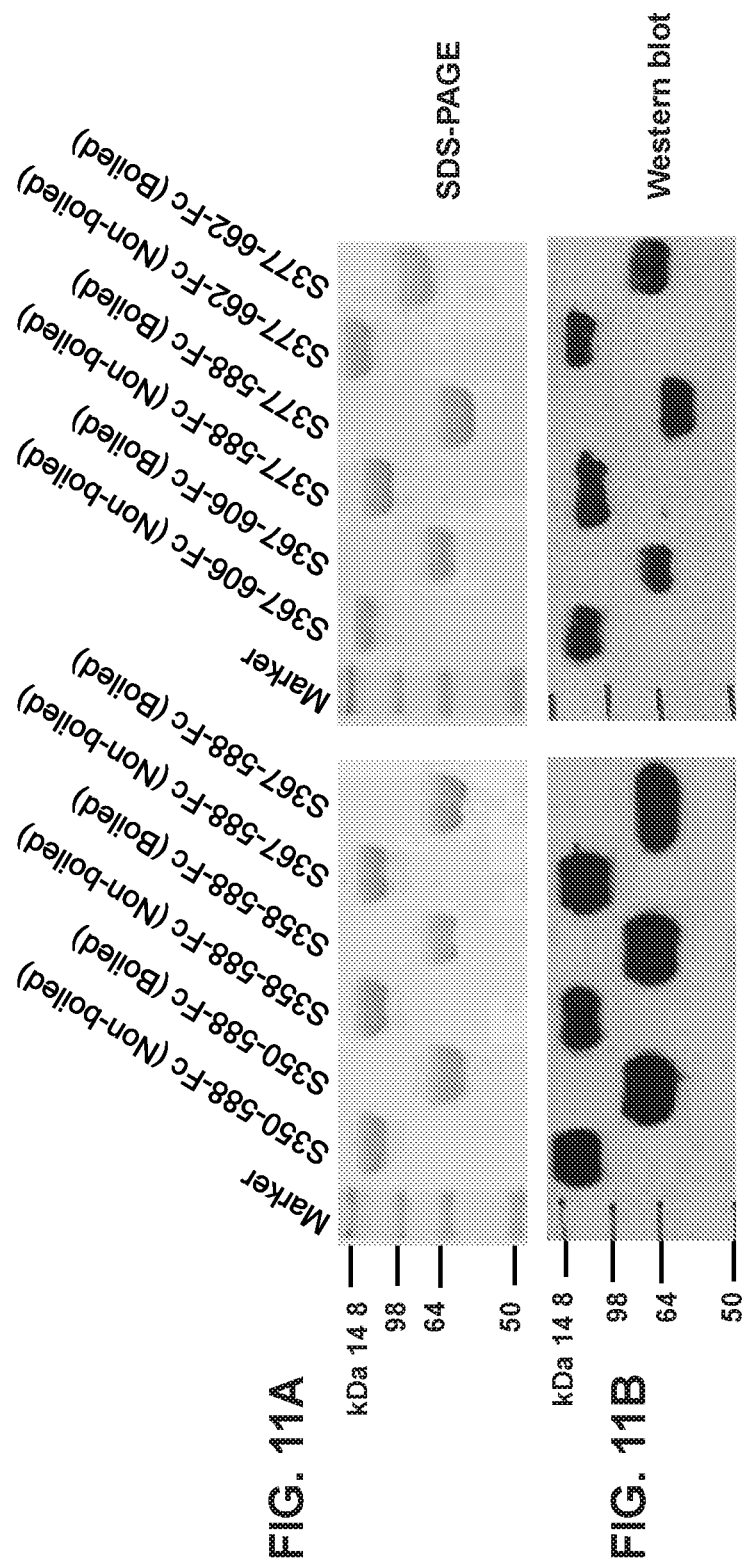
FIG. 11A and FIG. 11B depict the SDS-PAGE (FIG. 11A) and Western blot (FIG. 11B) analysis of the expressed MERS CoV RBD-Fc proteins. The protein molecular weight marker (kDa) is indicated on the left. Antisera from mice immunized with MERS-CoV S1-His were used for Western blot analysis.
Figure 13B:
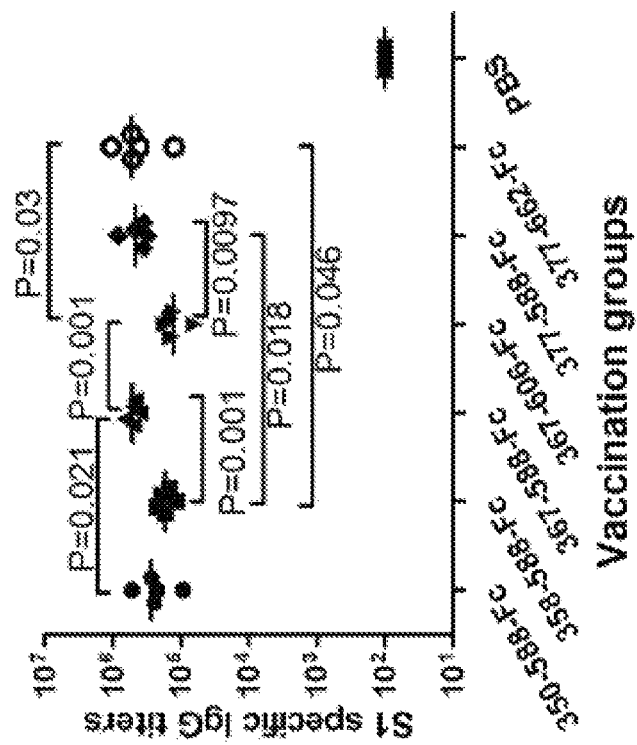
FIG. 13A and FIG. 13B depict IgG antibody responses in sera of mice immunized s.c. with MERS-CoV RBD-Fc proteins. MERS-CoV S1-His protein (S1-His) was used to coat the ELISA plates. Sera from 10 days post-$3^{rd}$ immunization were used for the detection, and the data are presented as mean A450 (FIG. 13A) or mean endpoint titers (FIG. 13B)±SD of five mice per group. Sera of mice injected with PBS were included as the control. P values from different groups were indicated.
Figure 13A:
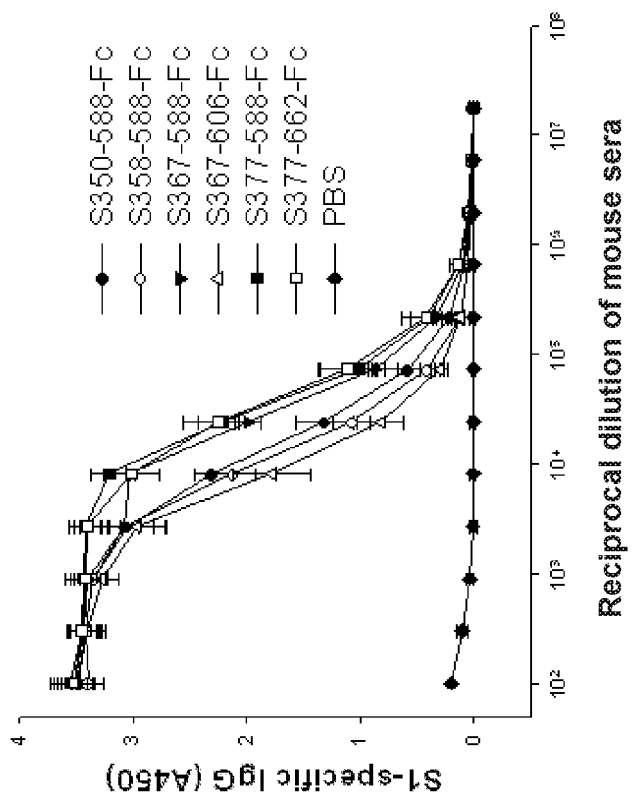
Figure 14:
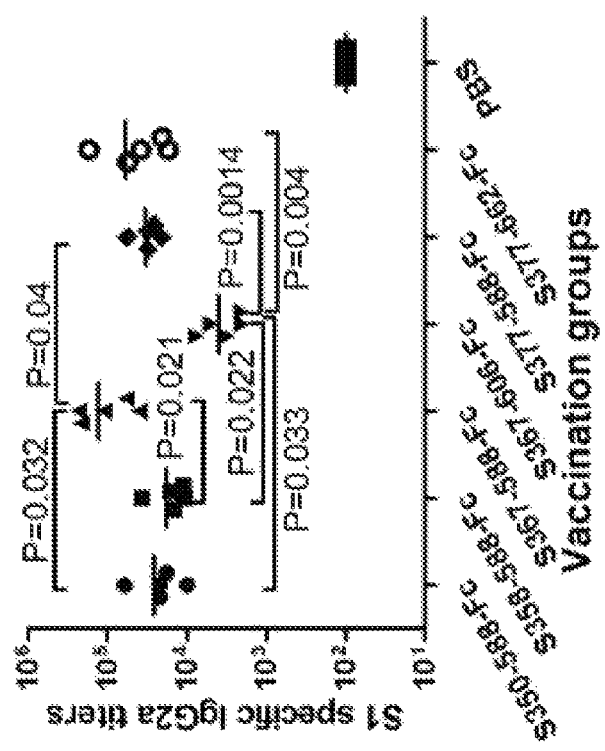
FIG. 14 depicts the IgG subtype antibody responses by ELISA in sera of mice immunized s.c. with MERS-CoV RBD-Fc proteins. MERS-CoV S1-His protein (S1-His) was used to coat the ELISA plates. Sera from 10 days post-$3^{rd}$ immunization were used for the detection, and the data are presented as mean endpoint titers±SD of five mice per group. Sera of mice injected with PBS were included as the control. P values from different groups were indicated.

Structural analysis of MERS-CoV RBD alone or complexed with its receptor DPP4 has identified residues 367-588 or 367-606 of MERS-CoV S1 subunit as the essential RBD (FIG. 10A). To identify the CND in the RBD of MERS-CoV that potentially induces the highest neutralizing antibody response, five additional recombinant proteins were constructed based on the structure-defined RBD of MERS-CoV (FIG. 10B), and these proteins were evaluated for their receptor-binding, antibody responses, and neutralization activity in immunized animals. As shown in FIG. 11A, all five RBD-Fc proteins, namely S350-588-Fc, S358-588-Fc, S367-588-Fc, S377-588-Fc, and S367-606-Fc, were expressed in a mammalian cell expression system at similar expression levels as S377-662-Fc. These proteins are capable of forming suitable conformational structures, having the molecular weight of non-boiled proteins 1-fold higher than that of the boiled proteins, and being recognized by MERS-CoV S1-specific antibodies (FIG. 11B), suggesting the high specificity of these proteins to MERS-CoV. In addition, all proteins bound well to the cellular-associated DPP4 receptor, with two clear bands (corresponding to the size of DPP4 or respective MERS-CoV RBD-Fc monomers) being detected in protein-Huh-7 cell co-immunoprecipitated samples, which reacted strongly with anti-DPP4 and anti-MERS-CoV S1 (FIG. 12A). The ability of these MERS-CoV RBD-Fc proteins in the binding to sDPP4 is notably different, with S367-588-Fc, S358-588-Fc, and S377-588-Fc maintaining higher binding affinity than S377-662-Fc, S367-606-Fc, and S350-588-Fc. As expected, a control protein hIgG-Fc had no binding with sDPP4 (FIG. 12B). The comparison of the humoral immune response in immunized mice indicates that S367-588-Fc, S377-588-Fc, and S377-662-Fc were able to induce higher levels of IgG antibody than S350-588-Fc, S358-588-Fc, and S367-606-Fc (FIGS. 13A and 13B), while S367-588-Fc potentially induced the highest titer of IgG2a subtype specific to the S1 of MERS-CoV (FIG. 14). More importantly, S377-588-Fc elicited the highest neutralizing antibody response among the tested RBD-Fc proteins against MERS-CoV infection (FIG. 15).

The produced MERS pseudovirus was able to efficiently infect a variety of target cells, including DPP4-expressing Huh-7, FRhK-4, MDCK, Vero, Vero E6, HEP-G2, A549, and Caco-2. The infection of MERS pseudovirus in target Huh-7 cells was significantly inhibited by antisera from mice immunized with MERS-CoV RBD-Fc proteins, such as the S377-588-Fc protein.

The S377-588-Fc protein was further characterized and evaluated for the potential as a therapeutic agent against MERS-CoV infection. Antisera from S377-588-Fc immunized mice can effectively block MERS-CoV RBD binding the DPP4 receptor, while control sera from PBS-immunized mice did not show any signs of inhibiting binding of S377-588 to DPP4-expressing Huh-7 cells (FIG. 16). The cross-linker analysis of the conformation of the S377-588-Fc indicates that this protein was able to form dimeric or tetrameric conformational structures (FIG. 17, left), which was confirmed by MERS-CoV S1-specific antibodies (FIG. 17, right). Importantly, the S377-588-Fc protein showed high ability to effectively inhibit MERS-CoV replication in the highly permissive human bronchial epithelial Calu-3 cells that express MERS-CoV's receptor DPP4, with the concentration as low as ~3 µg/ml inhibiting over 50% CPE formation caused by MERS-CoV infection (FIG. 18). These results suggest the use of S377-588-Fc as an important therapeutic agent against infections from MERS-CoV.

In conclusion, disclosed herein are recombinant proteins containing RBD fragments of MERS-CoV S1, a novel critical neutralizing domain of a new human coronavirus, MERS-CoV. These recombinant proteins, based on different fragments of RBD of MERS-CoV S protein linked to human IgG Fc, induced potent neutralizing antibodies against infection by MERS-CoV. Previous studies on S protein-based SARS vaccines have revealed that the mean neutralizing antibody titers as low as 1:284 could protect vaccinated animals against SARS-CoV challenge, suggesting that the expressed recombinant MERS-CoV RBD-Fc proteins have a great potential to be developed as a safe and effective vaccine and therapeutic agent against MERS-CoV infection.

The current study revealed low to no cross-reactivity and cross-neutralizing activity of MERS-CoV with SARS-CoV, suggesting that MERS-CoV has different mechanisms of infection, including using different receptors to infect cells.

Example 2

Viral subunit vaccines often contain immunodominant non-neutralizing epitopes that divert host immune responses. These epitopes should be eliminated in vaccine design, but there is no reliable method for evaluating an epitope's capacity to elicit neutralizing immune responses. Here we introduce a new concept "neutralizing immunogenicity index" (NII) to evaluate an epitope's neutralizing immunogenicity. To determine the NII, we mask the epitope with a glycan probe and then assess the epitope's contribution to the vaccine's overall neutralizing immunogenicity. As proof-of-concept, we measure the NII for different epitopes on an immunogen comprised of the receptor-binding domain from MERS coronavirus (MERS-CoV). Further, we design a variant form of this vaccine by masking an epitope that has a negative NII. This engineered vaccine demonstrate significantly enhanced efficacy in protecting transgenic mice from lethal MERS-CoV challenge.

A major goal of viral subunit vaccine development is to rationally design immunogens that can elicit strong neutralizing immune responses in hosts. The receptor-binding domains (RBDs) of virus surface spike proteins are the prime candidates for subunit vaccine design because they contain epitopes that can trigger strong immune responses. In addition, viral RBDs play essential roles in viral infection cycles by binding to their host receptor for viral attachment. Thus, part of the host immune responses elicited by viral RBDs can target the receptor-binding region and thereby neutralize viral entry into host cells. Rational design of viral subunit vaccines aims to focus the immune responses on neutralizing epitopes through masking or deletion of immunodominant non-neutralizing epitopes.

A critical gap in subunit vaccine design is the lack of an effective way to evaluate an epitope's neutralizing immunogenicity (i.e., its capacity to elicit neutralizing immune responses). There have been extensive efforts to predict epitopes' immunogenicity based on the physical and chemical properties of the epitopes. However, these methods are not designed to predict epitopes' "neutralizing" immunogenicity, which holds the key for subunit vaccine design. Although some experimental methods are available to measure the neutralizing immunogenicity of linear epitopes by taking linear peptides out of the context of proteins, these methods do not work for conformational epitopes, which are prevalent on RBD-based viral vaccines.

RBD-based coronavirus vaccines have been extensively pursued due to the threat that coronaviruses pose to human health. Coronaviruses are enveloped and positive-stranded RNA viruses. In 2002-2003, SARS coronavirus (SARS-CoV) infected over 8000 people with ~10% fatality rate. Since 2012, MERS coronavirus (MERS-CoV) has infected about 1700 people with ~36% fatality rate. The RBDs from SARS-CoV and MERS-CoV both contain a core structure and a receptor-binding motif (RBM). Their core structures are highly similar, but their RBMs are markedly different, leading to different receptor specificity: SARS-CoV recognizes angiotensin-converting enzyme 2 (ACE2), whereas MERS-CoV recognizes dipeptidyl peptidase 4 (DPP4). Both SARS-CoV and MERS-CoV RBDs are capable of eliciting strong neutralizing antibody responses. On one hand, because of the enriched neutralizing epitopes in their RBM and their high-yield expression as recombinant proteins, coronavirus RBDs are promising subunit vaccine candidates. Moreover, because of their relatively simple structures compared to the intact spike proteins, coronavirus RBDs provide an excellent model system for structure-based subunit vaccine design. On the other hand, recently determined cryo-EM structures of coronavirus spike proteins revealed that whereas the RBM of coronavirus RBDs is accessible, large surface areas of the RBD core structure are buried in the full-length spike proteins. Thus, when these previously buried areas on the surface of the RBD core become exposed in recombinant RBD vaccines, they likely contain immunodominant non-neutralizing epitopes that divert host immune responses. Therefore, coronavirus RBDs both hold promises and present challenges for vaccine development. It is critical to evaluate the neutralizing immunogenicity of different epitopes on coronavirus RBDs, such that immunodominant neutralizing and non-neutralizing epitopes can be preserved and eliminated, respectively.

Materials and Methods

Animals.

6-8 week female BALB/c mice and 4-month female human-DPP4-transgenic mice were used in the study. The animal studies were carried out in strict accordance with the recommendations in the Guide for the Care and Use of Laboratory Animals of the National Institutes of Health. The animal protocols were approved by the Committee on the Ethics of Animal Experiments of the New York Blood Center (Permit Number: 194.17) and Beijing Institute of Microbiology and Epidemiology (Permit Number: PMB15-0012).

Cell Lines.

HEK293T (human embryonic kidney) and Vero E6 (monkey kidney) cells were obtained from American Type Culture Collection. Huh-7 (human hepatoma) cells were kindly provided by Dr. Charles M. Rice at Rockefeller University. These cell lines were cultured in Dulbecco's modified Eagle medium (DMEM) supplemented with 10% fetal bovine serum (FBS), 2 mM L-glutamine, 100 units/mL penicillin, and 100 µg/mL streptomycin. Sf9 insect cells were purchased from Life Technologies Inc., and cultured in Sf-900 III SFM medium supplemented with 100 units/mL penicillin and 100 µg/mL streptomycin.

Expression and Purification of Recombinant Proteins.

The expression and purification of recombinant MERS-CoV RBD was carried out as previously described (Ma C, et al., Vaccine 32:6170-6176, 2014). Briefly, wild type (WT) RBD (residues 377-588; GenBank accession number: AFS88936.1) containing a C-terminal human IgG1 Fc tag was expressed in HEK293T cells, secreted into the cell culture supernatant, and purified by protein A affinity chromatography. Mutant RBD fragments containing engineered glycan probes were constructed via site-directed mutagenesis, and expressed and purified in the same way as the wild type RBD.

The expression and purification of recombinant human DPP4 was carried out as previously described (Yang Y, et al., Proc Natl Acad Sci USA 111:12516-12521, 2014). Briefly, human DPP4 ectodomain (residues 39-766; GenBank accession no. NP_001926.2) containing an N-terminal human CD5 signal peptide and a C-terminal His6 tag was expressed in insect sf9 cells using the Bac-to-Bac expression system, secreted to cell culture medium, and purified sequentially on HiTrap nickel chelating HP column and Superdex 200 gel filtration column.

SDS Gel Electrophoresis.

5 µg wild type or mutant MERS-CoV RBDs were subjected to SDS gel electrophoresis under denatured condition. Protein bands were stained using Coomassie Brilliant Blue R, and image captured using myECL Imager (Life Technologies Inc.).

Mass Spectrometry.

Wild type or mutant MERS-CoV RBDs at 100 µM concentration in 20 mM Tris-Cl, pH 7.4, 200 mM NaCl was ultrafiltrated with deionized water five times using an Amicon Ultra Centrifugal filter with a 10 kDa molecular weight cutoff. The desalted protein samples were subjected to MALDI-TOF Mass Spectrometry. Mass Spectrometry was performed in linear mode for molecular weight screening.

AlphaScreen Protein-Protein Binding Assay.

Binding between recombinant MERS-CoV RBDs and recombinant human DPP4 was measured using an AlphaScreen assay as previously described (Ma et al., 2014). Briefly, 3 nM wild type or mutant MERS-CoV RBD with a C-terminal Fc tag was incubated with 300 nM human DPP4 with a C-terminal His6 tag at room temperature for 1 hr. AlphaScreen protein A acceptor beads and nickel chelate donor beads (PerkinElmer Life Sciences) were added to the mixture at a final concentration of 5 µg/ml each. After incubation at room temperature for 1 hr, the AlphaScreen signal was measured using an EnSpire plate reader (PerkinElmer Life Sciences), reflecting the binding affinity between the two proteins.

FACS.

The binding between recombinant MERS-CoV RBDs and human DPP4 expressed on the Huh-7 cell surface was measured using fluorescence-activated cell sorting (FACS) as previously described (Du L, et al., J Virol 87:9939-9942, 2013). Briefly, Huh-7 cells were incubated with wild type or mutant MERS-CoV RBD (1.25 µg/ml) at room temperature for 30 min, followed by addition of FITC-conjugated anti-human-IgG-Fc polyclonal antibody (1:50 dilution) for 30 min. The amounts of RBD-bound Huh-7 cells were measured using flow cytometry, and the binding affinity between RBD and cell-surface DPP4 was characterized as median fluorescence intensity (MFI).

Animal Immunization and Sample Collection.

Animal immunization and sample collection were carried out as previously described (Ma et al., 2014). Briefly, BALB/c mice were subcutaneously immunized with wild type or mutant MERS-CoV RBD (10 µg/mouse) in the presence of Montanide ISA51 adjuvant. PBS plus Montanide ISA51 was included as a negative control. Immunized mice were boosted twice with the same immunogen and adjuvant at a 3-week interval, and sera were collected 10 days after the last immunization for detection of neutralizing antibodies.

ELISA.

The binding between recombinant MERS-CoV RBD and neutralizing mAbs was measured using ELISA as previously described (Du L, et al., J Virol 88:7045-7053, 2014). Briefly, ELISA plates were pre-coated with the same amount of wild type or mutant RBD (1 µg/ml) overnight at 4° C. After blocking with 2% non-fat milk at 37° C. for 2 hr, serially diluted mAbs were added to the plates and incubated at 37° C. for 1 hr. After washes, the plates were incubated at 37° C. for 1 hr with horseradish-peroxidase-conjugated anti-human-IgG-Fab polyclonal antibody (1:5,000 dilution). Enzymatic reaction was carried out using substrate 3,3',5,5'-tetramethylbenzidine and stopped with 1N $H_2SO_4$. Absorbance at 450 nm (A450) was measured using ELISA Plate Reader.

The competition between neutralizing mAbs and mutant-RBD-induced mouse serum for the binding of wild type MERS-CoV RBD was carried out using ELISA as described above, except that the binding between wild type RBD and the neutralizing mAb (hMS-1 or m336-Fab at 5 µg/ml concentration) was performed in the presence of serially diluted mouse serum (T579N-RBD-induced, wild-type-RBD-induced, or PBS-induced). The RBD-mAb binding was detected by addition of horseradish-peroxidase-conjugated anti-human-IgG-Fab polyclonal antibody (1:5,000 dilution) and subsequent enzymatic reaction.

Live MERS-CoV Neutralization Assay.

A micro-neutralization assay was carried out to test neutralizing antibodies against live MERS-CoV as previously described (Du et al., 2014). Briefly, serially diluted mouse sera were incubated at room temperature for 1 hr with ~100 infectious MERS-CoV virions (EMC-2012 strain), and were then incubated with Vero E6 cells at 37° C. for 72 hr. The neutralizing capability of the mouse sera was measured by determining the presence or absence of virus-induced cytopathic effect (CPE). Neutralizing antibody titers were expressed as the reciprocal of the highest dilution of sera that completely inhibited virus-induced CPE in at least 50% of the wells ($NT_{50}$).

MERS-CoV Challenge Studies.

MERS-CoV challenge studies were carried out using human-DPP4-transgenic mice as previously described (Zhao G, et al., PLoS One 10:e0145561, 2015). Briefly, mice were intramuscularly immunized with wild type or mutant MERS-CoV RBD (5 µg/mouse) in the presence of aluminum adjuvant, and boosted once 4 weeks after the initial immunization. 12 weeks after the second immunization, mice were challenged with MERS-CoV (EMC-2012 strain, $10^4$ $TCID_{50}$), and observed for 21 days for detection of survival rate and weight changes.

Statistical Analyses.

Figure 19A:
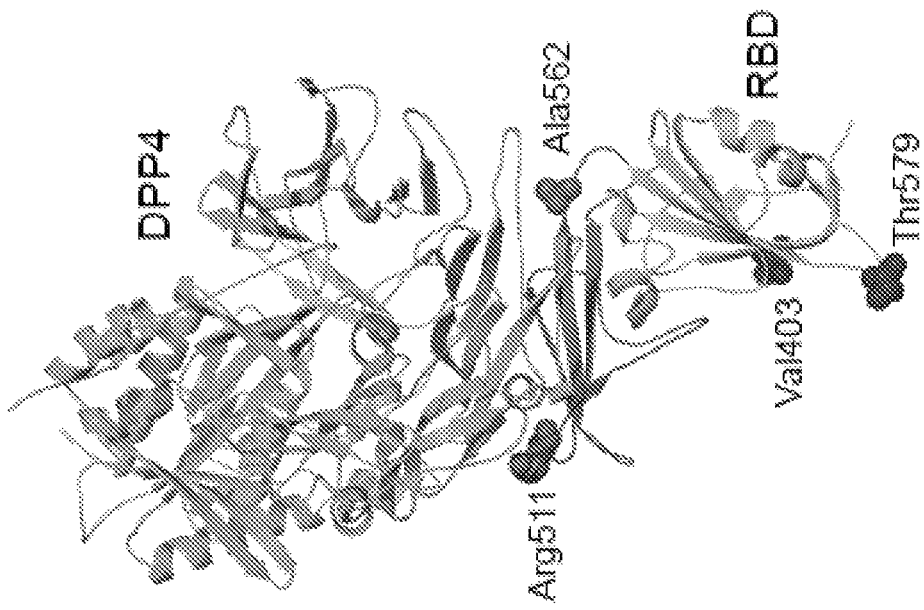
FIG. 19A-D. Introduction of glycan probes to MERS-CoV RBD vaccine.
Figure 19B:
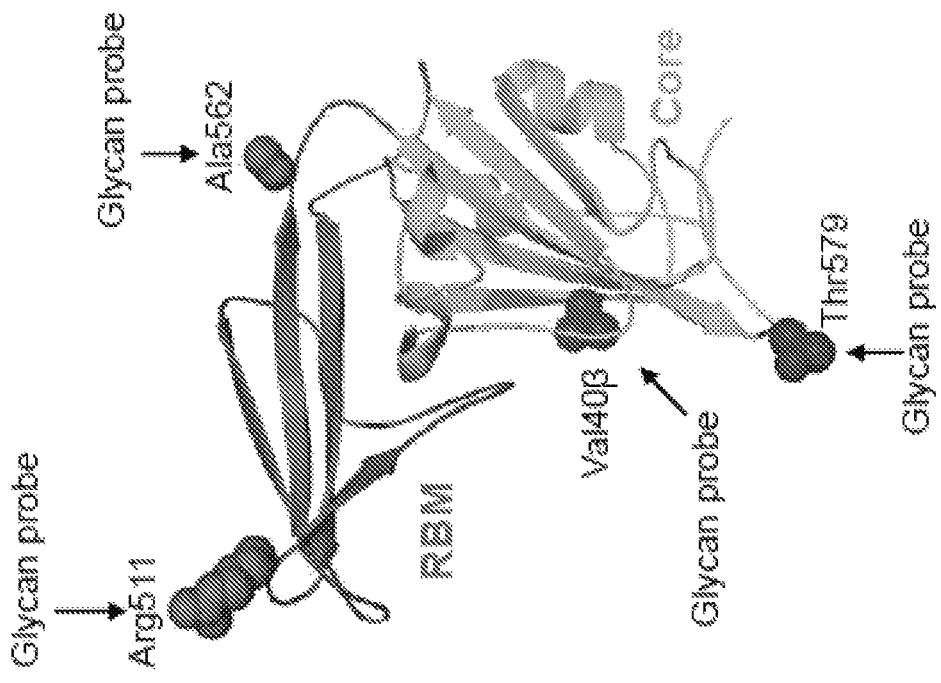
Figure 19C:
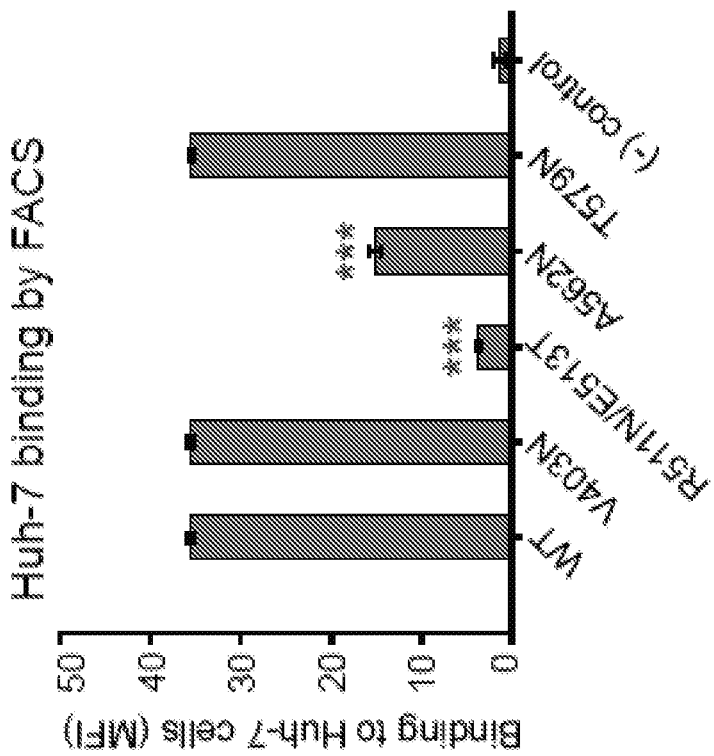
Figure 19D:
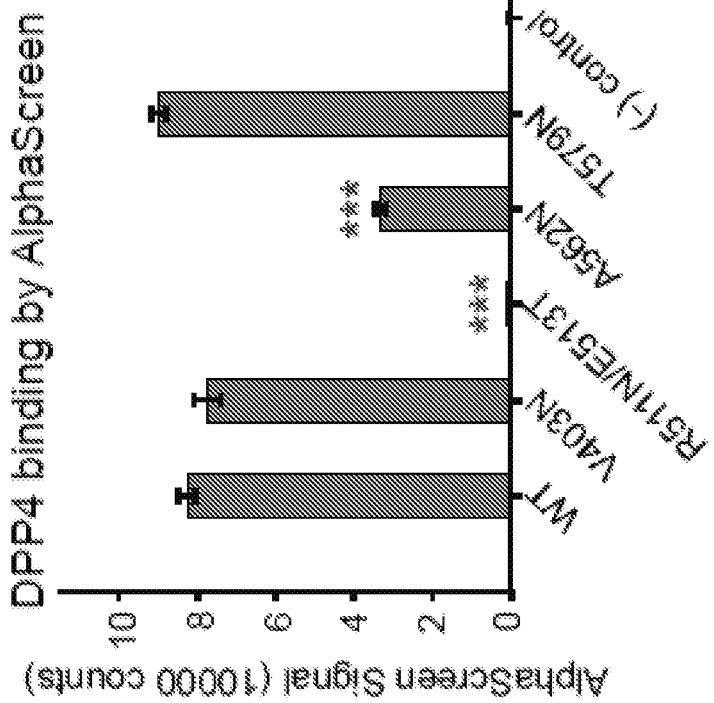

In FIG. 19C-D, comparisons between WT RBD and each of the mutant RBDs in their binding to recombinant DPP4 by AlphaScreen (FIG. 19C) or to cell-surface DPP4 by FACS (FIG. 19D) were done using two-tailed t-test (***: P<0.001; 3 measurements for each RBD in FIGS. 19C and 4 measurements for each RBD in FIG. 19D).

In FIG. 20A-D, nonlinear regression was performed using a log(inhibitor) vs. normalized response-variable slope model. R2 of curve fit is larger than 0.97 for all curves in FIG. 20A-D, except for the curve representing R511/E513 mutant RBD in FIG. 20A where R2 of curve fit is 0.194. Comparisons between WT RBD and each of the four mutant RBDs in their binding affinity to mAbs by ELISA were done using the extra sum-of-squares F test (***: P<0.001; 12 different dilutions of each mAb, 4 measurements at each dilution for each mAb).

In FIG. 21A, comparisons between WT RBD and each of the mutant RBDs in their capacity to induce neutralizing serum in mice were done using two-tailed t-test (*: P<0.05; 4 measurements for each RBD).

In FIG. 22, nonlinear regression was performed using a log(inhibitor) vs. normalized response-variable slope model. R2 of curve fit is larger than 0.98 for all curves in FIG. 22. Comparisons between WT-RBD-induced serum and T579N-RBD-induced serum in their inhibition of RBD/mAb binding by ELISA were done using the extra sum-of-squares F test (***: P<0.001; 4 different dilutions of each serum, 4 measurements at each dilution for each serum).

All statistical analyses were performed using GraphPad Prism 6 software.

Results

Introduction of Glycan Probes onto Epitopes on MERS-CoV RBD.

To evaluate the neutralizing immunogenicity of a specific epitope on viral RBD vaccines, we can either delete or mask the epitope and then measure the corresponding changes in the vaccine's capacity to elicit neutralizing immune responses. Alanine scanning of vaccine-surface residues likely leads to changes in the vaccine's overall immunogenicity that are too subtle to be measurable using currently available experimental methods, while deletion of a whole epitope may disturb the tertiary structure of the viral RBD. Instead, in this study we chose to mask the epitope of interest using a host-cell-derived glycan probe. This approach is effective and convenient because the glycan probe can impose steric interference for the access of antibodies and immune cells to the epitope, and also because the glycan probe is unlikely to interfere with the folding and solubility of the RBD. To place the glycan probe on an epitope, we introduced the N-linked glycosylation motif, asparagine-X-threonine (where X is any amino acid other than proline), onto different epitopes on viral RBD vaccines using site-directed mutagenesis.

As proof-of-concept, we chose to study several epitopes on the MERS-CoV RBD vaccine. The Fc-tagged RBD fragment containing residues from 377 to 588 was selected in this study because we previously showed that this fragment is a stable and effective vaccine candidate (see Example 1). Four distinct epitopes on this MERS-CoV RBD fragment were selected based on their location on the RBD surface and their possible functional role in receptor binding: (i) Arg511 (located on a protruding loop and in the receptor-binding motif (RBM) region); (ii) Ala562 (located on a β-strand and in the RBM region); (iii) Val403 (located on a β-strand and in the core region); (iv) Thr579 (located on a protruding loop and in the core region) (FIG. 19A-B). Based on the three-dimensional protrusion index map, the epitopes containing Arg511 and Thr579 both have a high protrusion index, whereas the epitopes containing Ala562 and Val403 both have a low protrusion index.

We introduced a glycan probe onto each of the above four epitopes on MERS-CoV RBD. To this end, we introduced single mutations V403N, T579N and A562N to pair with the already existent Thr405, Thr581 and Thr564, respectively, to generate three N-linked glycosylation sites. We also introduced double mutations R511N/E513T to generate the fourth N-linked glycosylation site. Each of these glycosylation sites was located in an individual MERS-CoV RBD fragment. We expressed and purified each of the four mutant RBDs in mammalian cells.

Characterization of RBDs Containing Engineered Glycan Probes.

To test whether each of the above four epitopes on MERS-CoV RBD was actually glycosylated, we performed both SDS gel electrophoresis and mass spectrometry. Compared with the wild type RBD, each of the mutant RBDs exhibited a slower electrophoretic mobility on the gel, consistent with additional glycosylation. Mass spectrometry revealed that the molecular weights of the mutant RBDs were ~1 to 2 kDa larger than that of the wild type RBD, which was also consistent with an introduced glycan probe in each of the mutant RBDs. For each of the purified mutant RBD samples, there was no visible presence of unglycosylated RBD on the SDS gel or the mass spectrometry spectrum. Thus, each of the four epitopes on MERS-CoV RBD had been successfully glycosylated.

To understand the correlation between the epitopes' role in receptor binding and their potential to be recognized by immune responses, we examined whether these engineered glycan probes on MERS-CoV RBD interfered with receptor binding. To this end, we used two alternative approaches. One approach was an AlphaScreen assay, which analyzed the interaction between recombinant RBDs and recombinant human DPP4 in solution (FIG. 19C), and the other approach was FACS, which examined the interaction between recombinant RBDs and human DPP4 expressed on the Huh-7 cell surface (FIG. 19D). The results from both assays revealed that the glycan probe located at residue 562 reduced the binding of the RBD to DPP4, the glycan probe located at residue 511 reduced the binding of the RBD to DPP4 even more, and the ones located at residues 403 and 579 had no impact on DPP4 binding. Structural analysis of the RBD/DPP4 interactions suggests that a glycan probe located at residue 511 would have serious steric clash with DPP4 binding, whereas a glycan probe located at residue 562 would have partial steric interference with DPP4 binding (FIG. 19B). Glycan probes located at residues 403 and 579 would be too far away from the receptor-binding region to have any impact on DPP4 binding. Hence, both the biochemical and structural analyses similarly elucidated the role of each of the glycan probes in the binding of the RBD to DPP4.

Figure 20A:
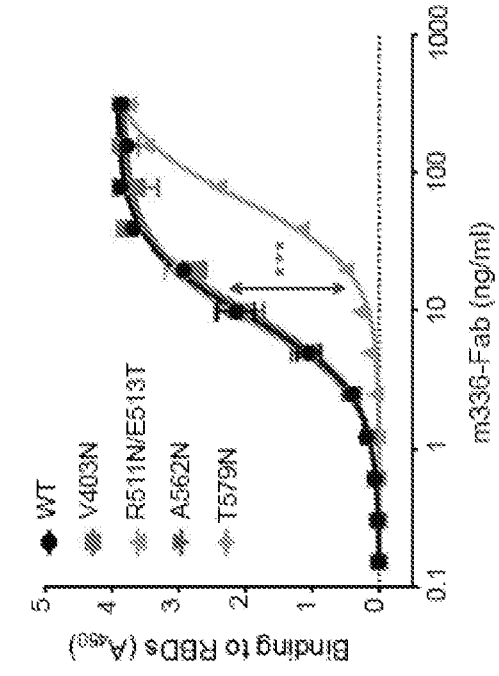
FIG. 20A-E. Role of engineered glycan probes in RBD binding to neutralizing mAbs.
Figure 20C:
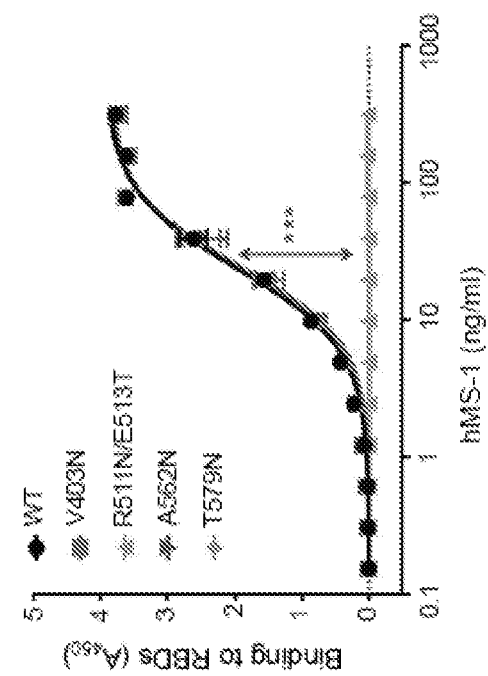
Figure 20B:
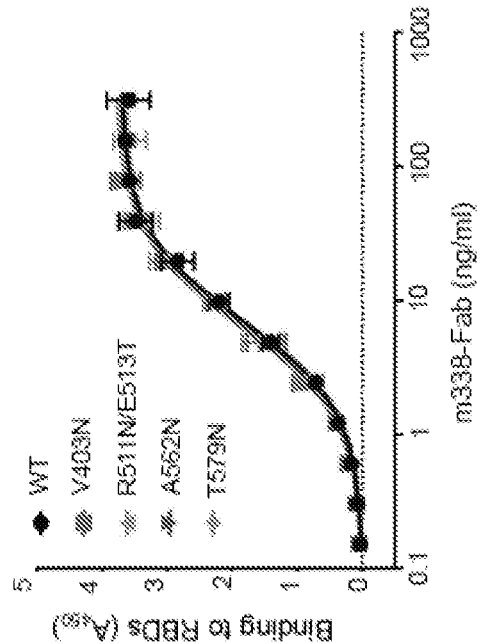
Figure 20D:
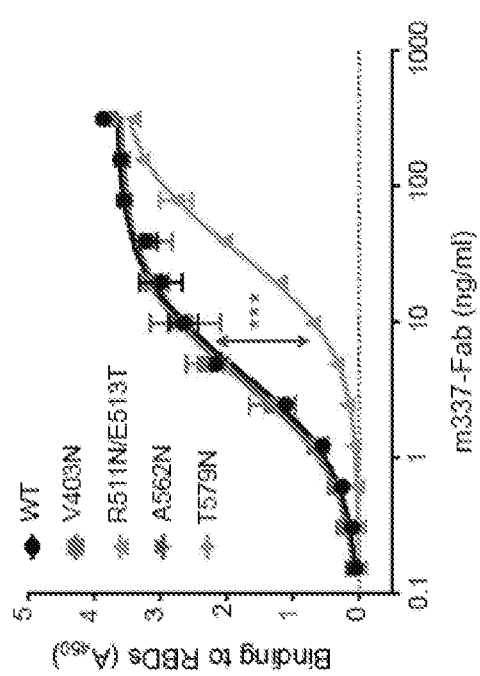
Figure 20E:
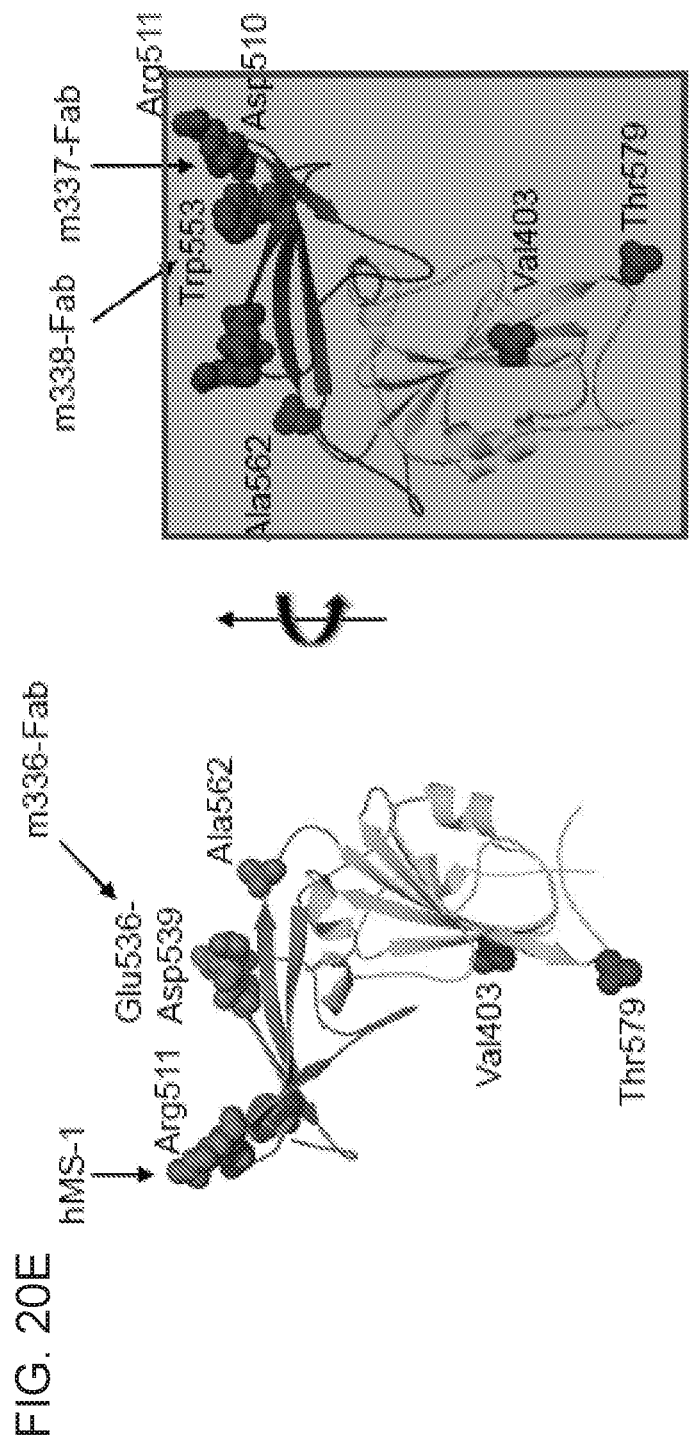

To understand the epitopes' potential to interact with neutralizing monoclonal antibodies (mAbs), we analyzed how the engineered glycan probes interfered with the binding of the RBD to different neutralizing mAbs. We used four humanized mAbs (hMS-1, m336-Fab, m337-Fab, and m338-Fab). All of these mAbs were previously shown to be highly potent in neutralizing MERS-CoV infection of human cells. ELISA between each of the RBDs and each of the mAbs demonstrated that the glycan probe located at residue 511 abolished the binding of the RBD to hMS-1 (FIG. 20A), reduced the binding of the RBD to m336-Fab and m337-Fab (FIG. 20B-C), and had no significant impact on the binding of the RBD to m338-Fab (FIG. 20D). In contrast, the glycan probes located at the other three residues, 403, 562 and 579, did not interfere with the binding of the RBD to any of the mAbs. The binding sites on the RBD for each of the mAbs were previously characterized through mutagenesis and/or structural studies. Three of the four mAbs, hMS-1, m336-Fab and m337-Fab, bind at or near the epitope containing Arg511, whereas all of the mAbs bind away from the epitopes containing Ala562, Val403, and Thr579 (FIG. 20E). Overall, among the four selected epitopes, the epitope containing Arg511 played the most important role in the binding of neutralizing mAbs, and consequently the glycan probe covering this epitope interfered most with the binding of neutralizing mAbs.

This study thus far has characterized the structural features, receptor binding, and neutralizing mAb binding for four selected RBD epitopes using a glycan probe strategy. Each of the glycan probes introduced to one of the RBD epitopes only interfered with the binding of DPP4 or mAbs that interact with this specific epitope, but had no impact on the binding of DPP4 or mAbs to distant epitopes. This observation suggests that each of the glycan probes only shielded the epitope where the glycan probe was attached to, but did not affect the structures of other antigenic sites. It is consistent with findings obtained in studies on another viral spike protein, respiratory syncytial (RSV) virus F protein.

Measurement of Neutralizing Immunogenicity of RBD Epitopes.

To evaluate how the glycan probes altered the neutralizing immunogenicity (that is, the capacity to induce neutralizing immune responses) of MERS-CoV RBDs, we immunized BALB/c mice with each of the four RBDs containing one of the glycan probes. Sera were collected from mice immunized with each of the RBDs, and tested for MERS-CoV-neutralizing antibodies. Compared to the wild type RBD vaccine, the RBDs containing a glycan probe at residues 579 and 511 induced significantly higher and lower neutralizing antibody titers, respectively, in mouse sera, whereas the RBDs containing a glycan probe at residues 403 and 562 failed to induce significant changes in neutralizing antibody titers in mouse sera (FIG. 21A). Thus, masking the epitope containing Arg511 led to reduced neutralizing antibody titers in the immunized mice, demonstrating that this epitope made a positive contribution to the vaccine's overall neutralizing immunogenicity. Based on the same rationale, the epitope containing Thr579 made a negative contribution and the epitopes containing Val403 and Ala562 made insignificant contributions to the vaccine's overall neutralizing immunogenicity. The experiments were further repeated twice and similar results were obtained. These results provided a qualitative evaluation of the neutralizing immunogenicity for each of these epitopes.

Here we introduce a novel concept "neutralizing immunogenicity index" (NII) to describe an epitope's neutralizing immunogenicity. NII is defined as the contribution of an epitope to the vaccine's overall neutralizing immunogenicity. It can be determined by masking the epitope with a glycan probe and then measuring the relative change of the vaccine's overall capacity to elicit neutralizing antibody titers (FIG. 21B). Based on this definition, we calculated the NII for each of the four epitopes on the RBD (FIG. 21C). The epitope containing Thr579 had an NII of −3.0. The negative sign of the NII suggests a negative contribution from this epitope to the vaccine's overall neutralizing immunogenicity, and the value of the NII implicates that masking this epitope using a glycan probe increased the vaccine's overall neutralizing immunogenicity by three-fold. Conversely, the epitope containing Arg511 had an NII of 0.6, suggesting that this epitope made a positive contribution to the vaccine's overall neutralizing immunogenicity and that masking this epitope using a glycan probe reduced the vaccine's overall neutralizing immunogenicity to 60% of that of the wild type vaccine. Therefore, the NII can serve as an effective tool to quantitatively evaluate the neutralizing immunogenicity of any epitope on the MERS-CoV RBD vaccine.

Figure 22A:
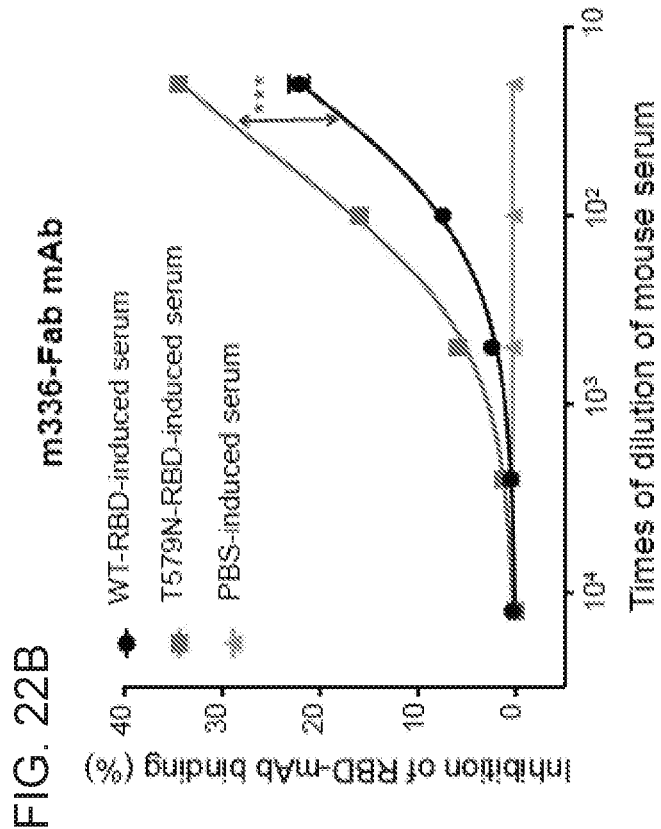
FIG. 22A-B. Masking negative epitope on the core led to immune refocusing on RBM. Competition assay was performed between neutralizing mAbs and glycosylation-mutant-RBD-induced mouse serum for the binding of wild type RBD. Specifically, ELISA was carried out between a neutralizing mAb, hMS-1 (FIG. 22A) or m336-Fab (FIG. 22B), and MERS-CoV RBD in the presence of mouse serum induced by the 579-glycosylated MERS-CoV RBD or mouse serum induced by the wild type MERS-CoV RBD. Mouse serum induced by PBS buffer was used as a negative control. Each of the sera was serially diluted before being used in the competition assay. For each serum dilution, the % reduction in mAb-RBD binding was computed for immune-sera present relative to immune-sera absent conditions. ***: P<0.001.
Figure 22B:
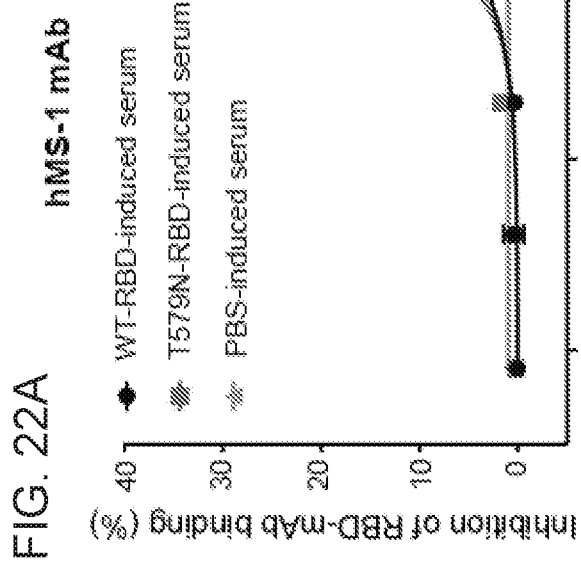

To investigate why masking a negative epitope led to enhanced neutralizing immunogenicity of the MERS-CoV RBD vaccine, we performed a competition assay between neutralizing mAbs and mutant-RBD-induced mouse serum for the binding of wild type MERS-CoV RBD. More specifically, ELISA was carried out between a neutralizing mAb and MERS-CoV RBD in the presence of mouse serum induced by the 579-glycosylated MERS-CoV RBD (FIG. 22A-B). As a comparison, the mouse serum induced by the wild type MERS-CoV RBD was also included. Two different mAbs were used in the competition binding assay: hMs-1, which binds to the RBM epitope containing Arg511, and m336-Fab, which binds to the RBM epitope surrounding Glu536-Asp539. The result showed that the serum induced by the 579-glycosylated RBD inhibited the mAb-RBD binding significantly better than the serum induced by the wild type RBD, revealing enhanced neutralizing capability of the mouse serum due to the glycosylation at the 579 position. Moreover, the mouse serum induced by the 579-glycosylated RBD demonstrated enhanced binding for at least two separate neutralizing epitopes on the RBM, one surrounding Arg511 and the other Glu536-Asp539. Thus, masking an epitope on the RBD core structure with a high negative NII refocuses the host immune response on neutralizing epitopes on the RBM, leading to enhanced neutralizing immunogenicity of the RBD vaccine.

Rational Design of RBD Vaccine with Enhanced Efficacy.

To prove that highly effective MERS-CoV RBD vaccines can be rationally designed based on epitopes' neutralizing immunogenicity, we investigated the efficacy of two engineered MERS-CoV RBD vaccines using virus challenge studies. These engineered RBD vaccines have a negative epitope (i.e., the epitope containing Thr579 and with an NII of −3.0) and a positive epitope (i.e., the epitope containing Arg511 and with an NII of 0.6) masked, respectively, by a glycan probe. We chose to mask the epitopes rather than deleting them or mutating all of their residues to alanines because introducing a glycan is more convenient in practice and less disruptive to the immunogen's tertiary structure. The wild type RBD vaccine was used as a control. The animal model for vaccine testing was the lethal transgenic mouse model expressing human DPP4 (hDPP4-Tg mice). These mice were chosen for analysis because they are very susceptible to MERS-CoV and also because preventing disease in these mice is a stringent test of efficacy. Briefly, hDPP4-Tg mice were immunized with each of the RBD vaccines and challenged with MERS-CoV, and the survival rate and weight changes of the mice were recorded.

Figure 23A:
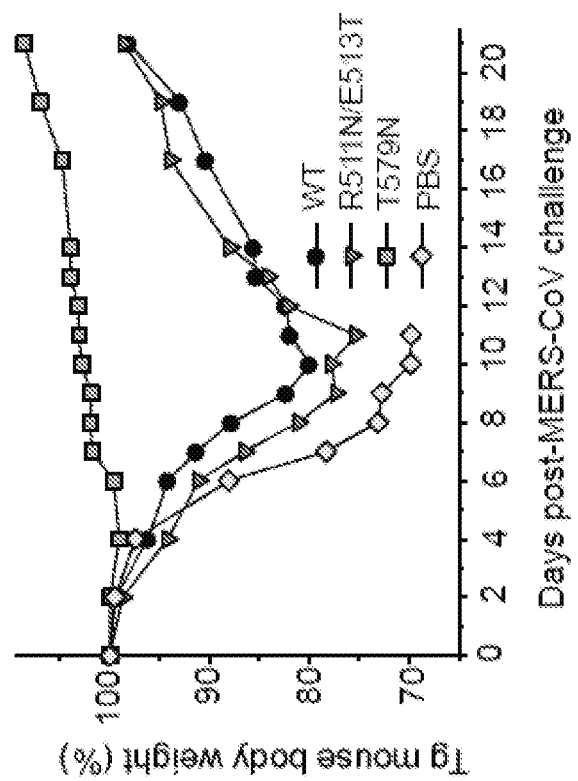
FIG. 23A-B. Rational design of MERS-CoV RBD vaccine with enhanced efficacy. Mice were immunized with two engineered RBD fragments containing a glycan probe at residue 511 (R511N/E513T) and residue 579 (T579N), respectively. Wild type RBD and PBS buffer were used as controls. Immunized mice were challenged with MERS-CoV (EMC-2012 strain), and observed for survival rate (FIG. 23A) and weight changes (FIG. 23B).
Figure 23B:
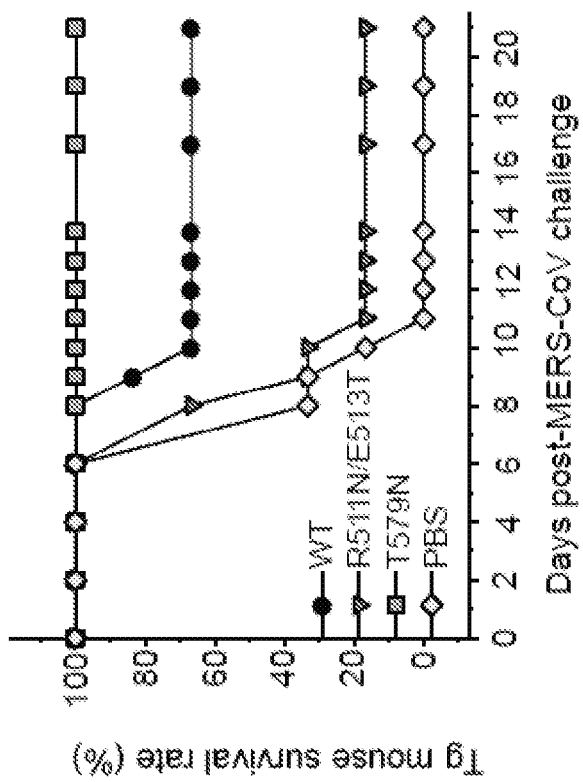

The efficacies of the RBD vaccines were evaluated based on the morbidity and mortality of the immunized and challenged mice. First, hDPP4-Tg mice immunized with the negative-epitope-masked RBD vaccine (i.e., RBD containing T579N mutation) all survived MERS-CoV challenge (100% survival rate), whereas hDPP4-Tg mice immunized with the wild type RBD vaccine and with the positive-epitope-masked RBD vaccine (i.e., RBD containing R511N/E513T mutations) demonstrated survival rates of 67% and 17%, respectively, after MERS-CoV challenge (FIG. 23A). Second, MERS-CoV challenge did not cause any weight loss in hDPP4-Tg mice immunized with the negative-epitope-masked RBD vaccine, but led to significant weight loss in hDPP4-Tg mice immunized with either the wild type RBD vaccine or the positive-epitope-masked RBD vaccine (FIG. 23B). The experiments were further repeated twice and similar results were obtained. These results revealed the enhanced efficacy of the negative-epitope-masked RBD vaccine and reduced efficacy of the positive-epitope-masked RBD vaccine, and demonstrated the utility of NII in developing a vaccine with increased immunogenicity in a stringent model of severe MERS.

Current vaccine design lacks an effective approach to evaluate the neutralizing immunogenicity of epitopes on viral subunit vaccines. In this study, we have developed a novel approach to measure vaccine epitopes' neutralizing immunogenicity. Using the MERS-CoV RBD as a model, we singly mask selected epitopes using host-derived glycan probes, and then measure the corresponding changes in the vaccine's overall neutralizing immunogenicity. We have also developed a method for calculating the NII for the selected epitopes. An epitope's neutralizing immunogenicity contains two parts: the neutralization capacity and immunogenicity. On the one hand, an epitope's neutralizing capacity is determined by the physical overlap of the epitope with the receptor-binding region and the potential role of the epitope in receptor binding. On the other hand, an epitope's immunogenicity is determined by its immune selfness (i.e., how similar or dissimilar the viral epitope is to a host-originated epitope), protrusion, and other physical and chemical properties of the epitope. Logically, an epitope's NII is correlated with a combination of factors such as immune selfness, protrusion, potential overlap with receptor-binding region, and more. Because of the complex nature of NII, it is unlikely that the NII can be reliably predicted by software; instead, this study demonstrates that NII can be experimentally measured using the glycan probe approach.

As proof-of-concept, we measured the Nil for four distinct epitopes on the MERS-CoV RBD vaccine, and also characterized the protrusion index, receptor binding, and monoclonal antibody binding of the RBDs each with an epitope masked by a glycan probe. The results revealed that the epitopes with a high and low protrusion index tend to have an NII with a high and low absolute value, respectively. In addition, epitopes within the receptor-binding region tend to have a positive NII, and the epitopes located outside the receptor-binding region tend to have a negative NII. We cannot correlate the immune selfness of epitopes with NII because there is no good method to evaluate the immune selfness of conformational epitopes. Overall, in rational design of viral subunit vaccines, the epitopes with a high positive NII should be preserved and exposed, while those with a high negative NII should be eliminated via deletion or masking. Indeed, our study has identified an epitope containing Thr579 as one with a high negative NII on MERS-CoV RBD. Thr579 is located on a protruding loop and away from the receptor-binding region, both of which contribute to its high negative NII. Importantly, Thr579 is buried inside the full-length coronavirus spike proteins, and only becomes exposed on the surface of the recombinant MERS-CoV RBD vaccine as an outcome of subunit vaccine design. To overcome this limitation of subunit vaccine design, the newly exposed epitopes with a high negative NII need to be masked or deleted.

To apply the NII strategy to vaccine design, we successfully enhanced the efficacy of the MERS-CoV RBD vaccine in virus challenge studies by masking its strong negative epitope (i.e., the epitope containing Thr579, with an NII of −3.0) with a glycan probe. This engineered vaccine effectively protected hDPP4-transgenic mice from a lethal MERS-CoV infection. Compared with the wild type RBD vaccine, mice immunized with the engineered RBD vaccine showed increased neutralizing antibody responses in their sera; when challenged by MERS-CoV, they also demonstrated higher survival rate and less weight loss. These results prove that negative epitopes should be eliminated in vaccine design. In contrast, another engineered vaccine with a positive epitope masked (i.e., the epitope containing Arg511, with an NII of 0.6) showed reduced efficacy in virus challenge studies, confirming that positive epitopes should be preserved and exposed in vaccine design. Taken together, we validated both the significance and feasibility of the NII strategy in vaccine design by successfully engineering a variant form of the MERS-CoV RBD vaccine with significantly enhanced efficacy.

Overall, our study contributes to viral subunit vaccine design in the following ways. First, our study introduces a new concept neutralizing immunogenicity index for the evaluation of how individual epitopes contribute to the overall neutralizing immunogenicity of subunit vaccines. Previous studies could not evaluate the neutralizing immunogenicity of conformational B-cell epitopes that dominate coronavirus RBD vaccines. Second, using the NII strategy our study identified an immunodominant non-neutralizing epitope on the surface of the MERS-CoV RBD core structure. This result shows that exposure of previously buried epitopes on viral subunit vaccines poses a challenge for subunit vaccine design. This concept may be critical for the development of many viral RBD-based vaccines. Third, our study demonstrates that masking an immunodominant non-neutralizing epitope with a negative NII value on the surface of the MERS-CoV RBD core structure can shift host immune responses towards the neutralizing epitopes in the RBM region, providing means to overcome the limitation of viral subunit vaccines from vaccine design. Previous studies showed that hypervariable regions on HIV gp120 divert host immune responses and that masking these regions can shift host immune responses towards conserved neutralizing epitopes, providing means to overcome the limitation of viral subunit vaccines from viral evolution. Fourth, although the NII strategy was used in the current study to improve the efficacy of viral subunit vaccines, it can also be potentially helpful in other epitope-based vaccine research. For example, previous studies masked or resurfaced non-neutralizing epitopes on viral immunogens, and used the engineered immunogens as baits to screen from neutralizing sera for monoclonal antibodies that bind to conserved neutralizing epitopes. It is conceivable that the NII strategy can help identify immunodominant non-neutralizing epitopes on immunogens, allowing more targeted epitope modifications for efficient antibody screening. Finally, our study suggests that a three-dimensional "neutralizing immunogenicity map" (NIM) can be drawn to describe the distribution of epitopes with different neutralizing immunogenicity on the surface of viral subunit vaccines. Such an NIM can guide targeted masking of multiple strong negative epitopes, further enhancing the efficacy of viral subunit vaccines.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

---

What is claimed is:

1. A protein comprising:
   a Middle East respiratory syndrome coronavirus (MERS-CoV) spike (S) protein sequence comprising amino acids 377-588 of the MERS-Co-V S protein with a T579N mutation (SEQ ID NO: 25); and an immunopotentiator.

2. The protein of claim 1, wherein the immunopotentiator sequence is an Fc fragment of human IgG (Fc), a C3d protein, an *Onchocerca volvulus* ASP-1, a cholera toxin, a muramyl peptide, or a cytokine.

3. The protein of claim 1, wherein the immunopotentiator is Fc.

4. The protein of claim 1, wherein the protein further comprises a stabilization sequence disposed between the MERS-CoV S protein sequence and the immunopotentiator sequence.

5. The protein of claim 4, wherein the stabilization sequence is a foldon (Fd) or GCN4.

6. The protein of claim 1, wherein the protein further comprises a linker sequence disposed between the MERS-CoV S protein sequence and the immunopotentiator sequence, and the linker is (GGGGS)$_n$ (SEQ ID NO:24), wherein n is an integer between 0 and 8.

7. The protein according to claim 6, wherein n is 1.

8. The protein of claim 1, wherein the protein comprises the sequence of S377-588-Fc T579N (SEQ ID NO:26).

9. An immunogenic composition comprising a protein, the protein comprising:
   an MERS-CoV S protein sequence comprising amino acids 377-588 of the MERS-Co-V S protein with a T579N mutation (SEQ ID NO: 25); and
   an immunopotentiator.

10. The immunogenic composition of claim 9, wherein the immunopotentiator sequence is an Fc fragment of human IgG (Fc), a C3d, an *Onchocerca volvulus* ASP-1, a cholera toxin, a muramyl peptide, or a cytokine.

11. The immunogenic composition of claim 9, wherein the immunopotentiator is Fc.

12. The immunogenic composition of claim 9, wherein the protein further comprises a stabilization sequence disposed between the MERS-CoV S protein sequence and the immunopotentiator sequence.

13. The immunogenic composition of claim 12, wherein the stabilization sequence is a foldon (Fd) or GCN4.

14. The immunogenic composition of claim 9, wherein the protein further comprises a linker sequence disposed between the MERS-CoV S protein sequence and the immunopotentiator sequence, and the linker is (GGGGS)$_n$ (SEQ ID NO:24), wherein n is an integer between 0 and 8.

15. The immunogenic composition of claim 9, wherein the protein comprises the sequence of S377-588-Fc T579N (SEQ ID NO:26).

16. A method of inhibiting MERS-CoV comprising:
   administering the immunogenic composition of claim 9 or the protein of claim 1 to a subject in need thereof;
   wherein the immunogenic composition induces an immune response that inhibits MERS-CoV infection in the subject.

17. The method according to claim 16, wherein the immunogenic composition further comprises an adjuvant.

18. The method according to claim 16, wherein the administering step comprises a prime immunization and at least one boost immunization.

19. The method according to claim 18, comprising more than one boost immunization, wherein the boost immunizations are administered weekly, every other week, monthly, or every other month.

20. The method according to claim 18, comprising more than one boost immunization, wherein the boost immunizations are administered weekly, every 2 weeks, every 3 weeks, every 4 weeks, every 5 weeks, every 6 weeks, every 7 weeks, every 8 weeks, every 9 weeks, every 10 weeks, every 11 weeks, or every 12 weeks.

* * * * *